(12) United States Patent
Neugebauer et al.

(10) Patent No.: US 12,018,072 B2
(45) Date of Patent: Jun. 25, 2024

(54) ANTIBODIES SPECIFIC FOR HUMAN COMPLEMENT C5A RECEPTOR (C5AR)

(71) Applicant: MORPHOSYS AG, Planegg (DE)

(72) Inventors: Julia Neugebauer, Munich (DE); Barbara Bachler-Konetzki, Hamburg (DE); Tanja Herrmann, Munich (DE); Winfried Elis, Wittnau (DE)

(73) Assignee: MORPHOSYS AG, Planegg (DE)

( * ) Notice: Subject to any disclaimer, the term of this patent is extended or adjusted under 35 U.S.C. 154(b) by 0 days.

(21) Appl. No.: 18/456,323

(22) Filed: Aug. 25, 2023

(65) Prior Publication Data

US 2024/0018225 A1 Jan. 18, 2024

Related U.S. Application Data

(63) Continuation of application No. 17/434,249, filed as application No. PCT/EP2020/056754 on Mar. 13, 2020, now abandoned.

(30) Foreign Application Priority Data

Mar. 14, 2019 (EP) .................................... 19162759

(51) Int. Cl.
  *C07K 16/18* (2006.01)
  *A61K 39/00* (2006.01)
(52) U.S. Cl.
  CPC ........ *C07K 16/18* (2013.01); *A61K 2039/505* (2013.01); *C07K 2317/14* (2013.01); *C07K 2317/21* (2013.01); *C07K 2317/33* (2013.01); *C07K 2317/35* (2013.01); *C07K 2317/72* (2013.01); *C07K 2317/732* (2013.01); *C07K 2317/76* (2013.01); *C07K 2317/92* (2013.01)
(58) Field of Classification Search
  CPC ................ C07K 16/18; C07K 2317/14; C07K 2317/21; C07K 2317/33; C07K 2317/35; C07K 2317/72; C07K 2317/732; C07K 2317/76; C07K 2317/92; A61K 2039/505
  See application file for complete search history.

(56) References Cited

FOREIGN PATENT DOCUMENTS

WO  2012/168199 A1  12/2012
WO  2018/234118 A1  12/2018

OTHER PUBLICATIONS

Anonymous, "C5ar, Human, Clone S5/1" XP055608334, Mar. 23, 2018.
Anonymous, "MorphoSys and I-Mab Sign Strategic Partnering Agreement for MorphSys's Novel Immuno-Oncology Agent MOR210" XP055608457 Nov. 15, 2018.
BioRad Datasheet: MCA1283F May 17, 2018.
Cho et al., "Autocrine Effects of Tumor-Derived Complement" Cell Reports 2014 6:1085-1095.
Corrales et al., "Anaphylatoxin C5a Creates a Favorable Microenvironment for Lung Cancer" J. Immunol. 2012 189:4674-4683.
Daniluk et al., "Safety and Tolerability of the Anti-C5AR Humanised Monoclonal Antibody NNC0151-000 in Patients with Rheumatoid Arthritis: A Phase 2, Randomised, Double-Blind, Placebo-Controlled, Multiple-Dose Trial" Ann. Rheum. Dis. 2014 73:684-685.
Darling et al., "Immunological Effects and Therapeutic Role of C5a in Cancer" Exp. Rev.Clin. Immunol. 2015 11:255-263.
Demaria et al., "Characterization of Anti-C5ar Antibodies for Specific Targeting of Myeloid Cells and Meutrophils in the TME" Innate Pharma 2017 Poster #B184, CRI-CIMT-EATI-AACR.
Hawksworth et al., "New Concepts on the Therapeutic Control of Complement Anaphylatoxin Receptors" Mol. Immunol. 2017, 89:36-43.
Markiewski et al., "Modulation of the Antitumor Immune Response by Complement" Nat. Immunol. 2008 9:1225-1235.
Markiewski, M.M. and Lambris J.D., "Unwelcome Complement" Cancer Res. 2009 69:2 pages.
Monk et al., "Function, Structure and Therapeutic Potential of Complement C5a Receptors" Br. J. Pharmacol. 2007 152:429-448.
Morgan B.P. and Harris, C.L, "Complement, a Target for Therapy in Inflammatory and Degenerative Diseases" Nat. Rev. Drug Discov. 2015 14:857-877.
Morgan et al., "Characterization of Neutralizing Antibodies Specific for a Peptide, C5aR-(9-29), Derived from the Predicted Amino-Terminal Sequence of the Human C5a Receptor" J. Immunol. 1993 151(1):377-388.
Nataf et al., "Human T Cells Express the C5a Receptor and are Chemoattracted to C5a" J. Immunol. 1999 162:4018-4023.
Oppermann et al., "Probing the Human Receptor for C5a Anaphylatoxin with Site-Directed Antibodies" 1993 J. Immunol. 151 7:3785-3794.
Sayegh et al., "Complement Anaphylatoxins as Immune Regulators in Cancer" Cancer Med. 2014 3:747-758.
Spaan et al., "Differential Interaction of the Staphylococcal Toxins Panton-Valentine Leukocidin and [gamma]-Hemolysin CB with Human C5a Receptors" J. Immun. 2015 195 1034-1043.
Wang et al., "Autocrine Complement Inhibits IL10-Dependent T-Cell-Mediated Antitumor Immunity to Promote Tumor Progression" Cancer Discov. 2016 6:1022-1035.
Werfel et al. "CD88 Antibodies Specifically Bind to C5aR on Dermal CD117+ and CD14+ Cells and React with a Desmosomal Antigen in Human Skin" J. Immun. 1996 157:1729-1735.
Extended European Search Report in EP19162759.5 dated Aug. 2, 2019.
International Search Report and Written Opinion in PCT/EP2020/056754 dated May 19, 2020.
International Preliminary Report on Patentability in PCT/EP2020/056754 dated Aug. 25, 2021.
Written Opinion of Intellectual Property Office of Singapore in 11202108761Y dated May 17, 2023.

*Primary Examiner* — Robert S Landsman
(74) *Attorney, Agent, or Firm* — Goodwin Procter LLP

(57) ABSTRACT

The present invention provides novel antibodies or antibody fragments specifically binding to human C5aR. In particular, it relates to antibodies or antibody fragments that have combined beneficial properties and are therefore useful for the treatment of inflammatory or autoimmune diseases or cancer.

30 Claims, 11 Drawing Sheets

Specification includes a Sequence Listing.

| Antigen | MAB#2 | | MAB#1 | |
|---|---|---|---|---|
| | 100 nM | 10 nM | 100 nM | 10 nM |
| Blank | 2 | 1 | 2 | 1 |
| huC5aR_NT_bio | 49 | 46 | 84 | 82 |
| Protein A | 1 | 1 | 1 | 1 |
| Serum albumin (h) | 2 | 1 | 2 | 2 |
| Fibrinogen (b) | 2 | 1 | 2 | 1 |
| Hemoglobin (h) | 2 | 1 | 2 | 1 |
| Transferrin (b) | 9 | 4 | 19 | 8 |
| Antitrypsin | 2 | 2 | 2 | 1 |
| Cell surface rec. 1_Lys (h) | 2 | 1 | 2 | 1 |
| Cell surface rec. 2_Fc (h) | 2 | 1 | 2 | 1 |
| Cell surface rec. 3_Fc (h) | 2 | 2 | 2 | 2 |
| GFP | 2 | 1 | 2 | 1 |
| Baculovirus particles | 3 | 1 | 3 | 1 |
| Fc (h) | 3 | 1 | 2 | 1 |
| HKB11 vesicle | 3 | 1 | 3 | 1 |
| Dextransulfate sodium salt | 2 | 1 | 2 | 1 |
| Pepsinogen | 5 | 1 | 4 | 1 |
| Amyloglycosidase | 2 | 1 | 3 | 1 |
| Trypsin inhibitor | 7 | 3 | 5 | 2 |
| Cytochrome C | 2 | 1 | 2 | 1 |
| Myoglobin | 2 | 1 | 2 | 1 |
| Lectin | 2 | 1 | 2 | 1 |
| Ovalbumin | 4 | 1 | 2 | 1 |
| Trypsinogen | 2 | 1 | 2 | 1 |
| Milk powder | 2 | 1 | 2 | 1 |
| RNase B | 2 | 1 | 2 | 1 |
| RNase A | 6 | 2 | 4 | 2 |
| Lysozyme | 2 | 1 | 2 | 1 |
| anti-human Fab (Dianova) | 1 | 1 | 1 | 1 |
| anti-human Fc | 1 | 1 | 1 | 1 |
| Blank | 2 | 1 | 2 | 1 |
| Blank | 2 | 1 | 2 | 1 |

Figure 10

ANTIBODIES SPECIFIC FOR HUMAN COMPLEMENT C5A RECEPTOR (C5AR)

CROSS REFERENCE TO RELATED APPLICATIONS

The present application is a continuation of U.S. application Ser. No. 17/434,249, filed Aug. 26, 2021, now abandoned, which was a 35 U.S.C. § 371 National Stage application of International Application Number PCT/EP2020/056754, filed Mar. 13, 2020, which claims priority to provisional application EP19162759.5 filed Mar. 14, 2019, each of which is hereby incorporated by reference in their entirety.

SEQUENCE LISTING

This application contains a Sequence Listing which has been submitted electronically in XML format and is hereby incorporated by reference in its entirety. Said XML copy, created on Aug. 24, 2023, is named "HBIO-294C1_SequenceListing.xml" and is 106,784 bytes in size.

FIELD OF THE INVENTION

The present disclosure relates to antibodies, which interact with C5aR, in particular with human C5aR. The present disclosure also relates to nucleic acid compositions, vector composition and host cells capable of expressing said antibodies, pharmaceutical compositions comprising said antibodies and uses of said antibodies for the treatment of specific diseases and/or for diagnostic purposes.

BACKGROUND

The C5a anaphylatoxin chemotactic receptor 1 (C5aR) (also known as CD88) is a G-protein-coupled receptor (GPCR) belonging to the rhodopsin family and is one of the two high-affinity receptors for the ligand, C5a, which is produced in serum as one of the core effector components of the complement response. Under physiological conditions, C5a acts as chemotactic agent for inflammatory cells, stimulates their respiratory burst as well as cytokine and chemokine release, and functions to increase vascular permeability.

C5aR appears widely expressed by various cell types. Highest C5aR expression levels are described for neutrophils. Low-to-moderate expression levels have been shown for macrophages/monocytes, dendritic cells, mast cells, eosinophils, lung vascular smooth muscle cells, astrocytes, microglia, osteoblasts, osteoclasts, epithelial and endothelial cells (Monk P N et al., Br J Pharmacol. 2007, 152: 429-448; Wetsel R A, Immunol Lett. 1995, 44: 183-187). For human T cells, low expression levels have been observed (Nataf S, J Immunol. 1999, 162: 4018-4023).

Cell responses to C5a are tightly controlled by ligand-induced receptor internalization. C5aR is described to rapidly and dose-dependently internalize upon C5a treatment and up to 90% of the receptor is recycled back to the cell surface. Thus, the high expression levels of C5aR in combination with its fast turn-over rate could be limiting in terms of efficacy due to target-mediated drug disposition (TMDD) effects.

The interaction of C5aR with C5a has been described in many different disease settings; most of them being involved in inflammatory and autoimmune diseases (Morgan B P et al., Nat Rev Drug Discov. 2015, 14: 857-877; Hawksworth O A et al., Mol Immunol. 2017, 89: 36-43). Some initial research has been performed to identify the underlying mechanisms by which C5a stimulates tumor growth (Markiewski M M et al., Nat Immunol. 2008, 9: 1225-1235; Corrales L. et al, J Immunol. 2012, 189: 4674-4683; Cho M S et al., Cell Rep. 2014, 6: 1085-1095). Most of the data implicates that C5a increases cancer cell proliferation, intratumor angiogenesis and enhances tumor invasiveness and metastasis. More recent data also implicate a role for C5a/C5aR in the generation of immunosuppressive environments in the context of solid tumors (Sayegh E T et al., Cancer Med. 2014, 3: 747-758; Darling V R et al., Expert Rev Clin Immunol. 2015, 11: 255-263; Markiewski M M et al., Cancer Res. 2009, 69: 6367-6370) resulting in enhanced primary tumor growth by inhibiting antitumor responses (e.g. increased recruitment of C5aR-expressing myeloid cells such as myeloid-derived suppressor cell (MDSC) or M2 macrophages). Based on these findings, combination strategies with already known anti-tumor agents, such as immune checkpoint protein inhibitors in order to boost a subject's immune response by reducing the immunosuppressive microenvironment are in focus of research and clinical development (Wang Y, et al.: Cancer Discov. 2016, 6: 1022-1035).

To date, only one specific complement therapeutic has been approved, which targets the upstream molecule of C5a, namely C5. The humanized anti-C5 mAb Eculizumab is capable of binding C5, preventing its cleavage and formation of C5a and C5b proteins, and subsequent MAC formation. Various other therapeutic monoclonal C5 specific antibodies, such as ALXN1210 or LFG316 are under clinical evaluation (Hawksworth O A et al., Mol Immunol. 2017, 89: 36-43). However, since increased infection risk is a major concern with chronic C5 treatment, specific targeting of downstream molecules whilst preventing the biological activities of other complement components is clearly advantageous. Accordingly, a number of antagonistic C5a specific monoclonal antibodies are under development.

Direct targeting of C5aR has a number of advantages over targeting C5 or C5a, respectively. First, the inhibition of the receptor alone would preserve MAC activity, thereby reducing the potential risk of infections. Second, C5aR blockade permits continued C5a interaction with its second receptor C5L2. Since C5L2 has been reported to have anti-inflammatory effects, maintaining an effective C5L2 signalling pathway may result in increased efficacy or reduced dosing requirements. Third, direct C5aR targeting may provide pharmacodynamic advantages over inhibition of soluble C5a, due to its small molecular weight and its high turnover rate. Overall, there is strong interest in developing C5aR inhibitors, such as aptamers, peptides, and non-peptide small molecules being tested in pre-clinical and clinical trials.

Neutralizing polyclonal antiserum or monoclonal antibodies directed against the N-terminal extracellular region of human C5aR and being able to interfere with C5aR-C5a interaction has been described in the art (see e.g. Morgan et al., The Journal of Immunology, Vol 151, 377-388. No. 1, Jul. 1, 1993; Oppermann et al., The Journal of Immunology, Vol 151, 3785-3794, No. 7, Oct. 1, 1993), However, these C5aR specific antibodies are not suited for the clinical development and therapeutic use in human, especially due to their animal origin (which makes them immunogenic in human patients), clonality, and/or lack of cross-reactivity to relevant animal species.

Therapeutic antibodies targeting C5aR has been considered for clinical development. However, the clinical development of the antagonistic C5aR specific antibody Neutrazumab, a humanized IgG4 mAb was stopped in Phase II clinical trials due to issues with immune cell depletion and immunogenicity (Daniluk S et al., Annals of the Rheumatic Diseases. 2014, 73: 684-685). Since C5aR appears constitutively expressed on a variety of cell types, it is important that an antagonistic antibody does not induce any depletion of the target cells.

To overcome the limitations of Neutrazumab, a second generation of a C5aR specific antibody has been generated, namely NNC0215-0384 (US2013/0295116 (NOVO NORDISK); clone 32F3A6GL). This antibody is a human IgG1 antibody derived from transgenic mice and is currently under clinical development as IPH5401 in the field of cancer (Olivier Demaria et al., Innate Pharma 2017. Poster #B184. CRI-CIMT-EATI-AACR Mainz). IPH5401 bears a silenced human IgG1 Fc region to eliminate the ability of the antibody to induce effector function. This antibody is herein referred to as RefMAB #1.

SUMMARY OF THE INVENTION

The present disclosure provides novel antibodies and antibody fragments.

The antibodies and antibody fragments disclosed herein can specifically bind to human C5aR and preferably cross-react with C5aR from cynomolgus monkey. Accordingly, in some embodiments, the disclosed antibodies are specific for human C5aR and cynomolgus C5aR. In some other embodiments, the disclosed antibodies or antibody fragments bind to the N-terminal extracellular region of human and cynomolgus C5aR.

This is in contrast to the above referenced prior art antibody IPH5401, which binds to the second extracellular loop of human C5aR resulting in the lack of binding to cynomolgus monkey C5aR, a commonly used relevant toxicology species.

In addition, the inventors of the present invention surprisingly found that the presently claimed C5aR specific antibodies are not only significantly more potent in neutralizing pathophysiological C5a concentrations when compared to IPH5401 but also revealed an increased potency over time in inhibiting C5 mediated activation of neutrophils in vitro.

Accordingly, in some embodiments, the disclosed antibodies can efficiently inhibit C5a induced C5aR activity in vitro, most notably at pathophysiological C5a concentration. The disclosed antibodies or antibody fragments may also inhibit C5a induced leucocyte activation in vitro as determined by their ability to inhibit C5a induced upregulation of CD11b in granulocytes and/or monocytes. In some embodiments, the disclosed antibodies or antibody fragments inhibit human C5a induced CD11b expression in human granulocytes with an $IC_{50}$ concentration of 42 nM in the presence of 150 nM human C5a in vitro. In some other embodiments, the disclosed antibodies may exhibit an increased potency to inhibit C5a induced upregulation of CD11b in granulocytes and/or monocytes after a prolonged period of incubation time. The disclosed antibodies may be also efficient in inhibiting C5a induced neutrophil migration.

In sum, the present disclosure provides novel antibodies, which are superior to the C5aR specific antibodies known from the art. In particular, the antibodies of the present disclosure are human antibodies with high affinity binding to human C5aR, which preferably cross-react with cynomolgus monkey C5aR and have favourable functional and safety properties never have been observed before. These features makes the antibodies of the present disclosure highly desirable for therapeutic use such as for preventing and/or treating inflammatory and autoimmune diseases as well as cancer.

The present disclosure provides isolated antibodies or antibody fragments that specifically bind to human C5aR having CDR regions according to Table 1 or Table 2 of the present specification. The present disclosure also provides isolated antibodies or antibody fragments specific for human C5aR having a variable heavy chain region (VH) and a variable light chain region (VL) comprising the amino acid sequences according to Table 1 or Table 2 of the present specification. The present disclosure also provides isolated antibodies or antibody fragments specific for C5aR having a heavy chain (HC) and a light chain (LC) comprising the amino acid sequences according to Table 1 or Table 2 of the present specification.

The isolated antibodies of the present disclosure do not substantially induce effector function in vitro. Such effector function may comprise ADCP, ADCC or CDC. Furthermore, the isolated antibody or antibody fragments of the present disclosure comprise one or more amino acid substitution selected from the group of: L234A, L235E, G237A, A330S and P331S, with numbering according to EU index. In particular, the isolated antibodies or antibody fragments of the present disclosure comprise a variant human IgG1 Fc region, which comprises the following amino acid substitutions: L234A, L235E, G237A, A330S and P331S with numbering according EU index.

The present disclosure also provides the isolated antibodies or antibody fragments of the present disclosure for use in medicine.

The present disclosure also provides methods for treating a subject suffering from a disease, such as an inflammatory or autoimmune disease or cancer, by administering to said subject an effective amount of the antibodies or antibody fragments of the present disclosure. Preferably, said subject is a human.

The present disclosure also provides pharmaceutical compositions comprising the isolated antibodies or antibody fragments of the present disclosure, and a pharmaceutically acceptable carrier.

The present disclosure also provides nucleic acid compositions encoding the isolated antibodies or antibody fragments of the present disclosure. The present disclosure also provides vector compositions comprising the nucleic acid compositions encoding the isolated antibodies or antibody fragments of the present disclosure. The present disclosure also provides host cells comprising the vector compositions or nucleic acids compositions encoding the isolated antibodies or antibody fragments of the present disclosure.

The present disclosure also provides methods for treating a subject suffering from a disease, such as an inflammatory disease, autoimmune disease or cancer by administering to said subject an effective amount of the isolated antibodies or antibody fragments of the present disclosure. Preferably, said subject is a human.

The present disclosure also provides pharmaceutical compositions comprising the isolated antibodies or antibody fragments of the present disclosure, and a pharmaceutically acceptable carrier.

There is utility in the claimed antibodies or antibody fragments. Furthermore, there is utility in the claimed method to identify such antibodies or antibody fragments.

Utilization of the claimed antibodies or antibody fragments is to alter the biological activity of human C5aR. In particular, the claimed antibodies or antibody fragments are for therapeutic use, such as the treatment of inflammatory or autoimmune disease or cancer

BRIEF DESCRIPTION OF THE DRAWINGS

FIG. 5: Inhibition of human C5a induced CD11b upregulation in human granulocytes at regular and pathophysiological C5a concentrations. A+B Comparison of MAB #1, MAB #2 and RefMAB #1 in a CD11b whole blood assay. Log dose-inhibition curves are shown. Human granulocytes were gated as target cells. As quantitative read-out, the IgG concentration needed to reach 50% inhibition of CD11b upregulation was calculated ($IC_{50}$ concentration). $IC_{50}$ concentrations for each IgG are depicted below the x-axis. A Log dose-response curves for increasing concentrations of IgG and 15 nM human C5a. B Log dose-response curves for increasing concentrations of IgG and 150 nM human C5a.

FIG. 10: Protein Panel Profiling (3P) results for MAB #1 and MAB #2. The numbers for each antibody represents the obtained binding signal for each antibody and tested protein compared to the binding of isotype negative control antibody MOR03207. Antibodies were tested at a concentration of 10 nM and 100 nM, respectively.

DETAILED DESCRIPTION OF THE INVENTION

Figure 1:
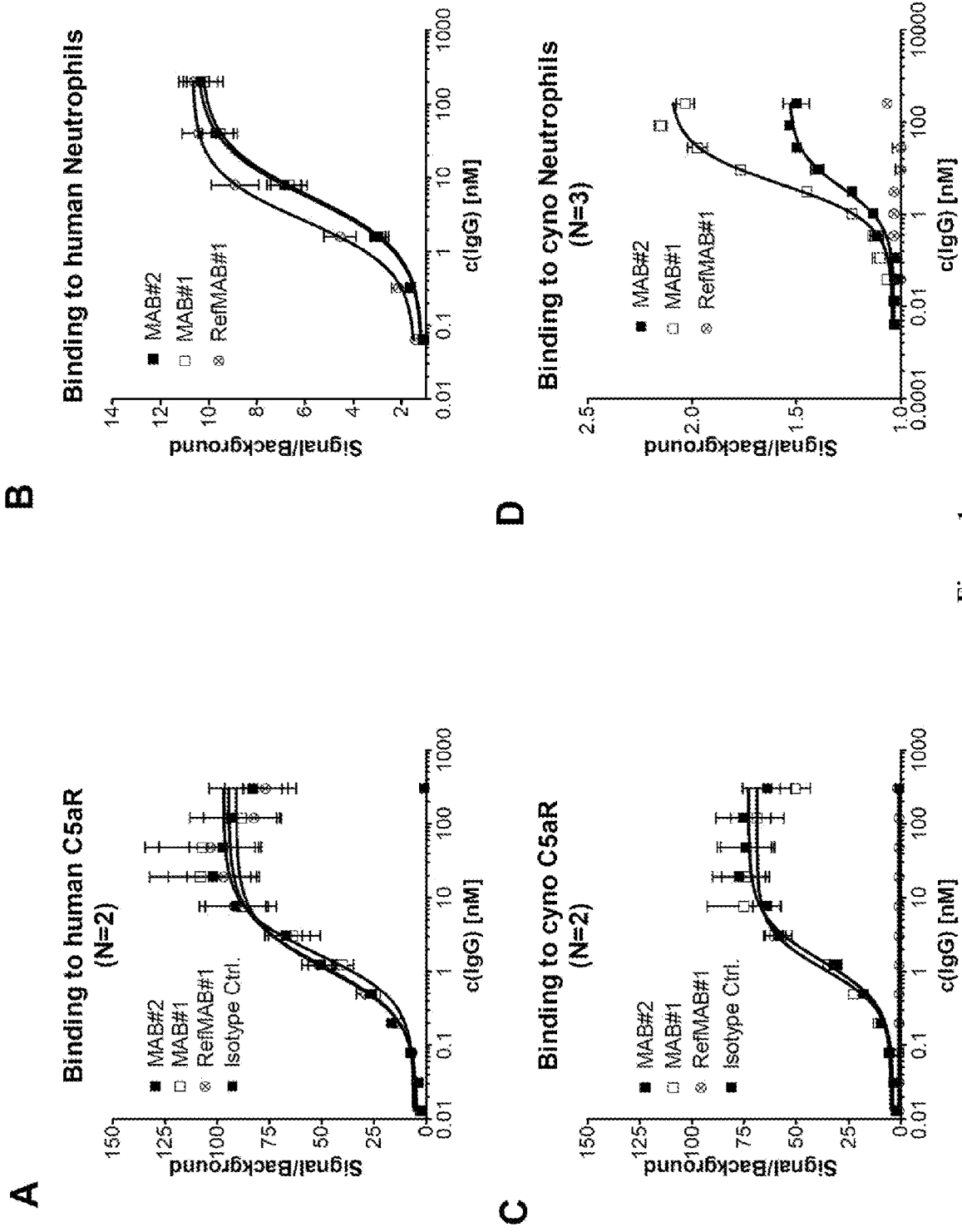
FIG. 1: Cell binding of MAB #1, MAB #2, RefMAB #1 and negative isotype control MOR03207 to human and cynomolgus monkey C5aR determined via FACS. A Dose response binding to human C5aR overexpressed on Flp-In™ CHO cells. B Dose response binding to cynomolgus monkey C5aR overexpressed on Flp-In™ CHO cells. C Average dose response binding to purified human neutrophils obtained from whole blood of three different donors. D Average dose response binding to purified cynomolgus monkey neutrophils obtained from whole blood from three different monkeys.

The disclosure pertains to a number of human antibodies, which recognize human C5aR.

Definitions

The term "C5aR" refers to a protein known as C5a anaphylatoxin chemotactic receptor 1 or CD88. Human C5aR (Uniprot: P21730|1-350) (referred to herein as the "D/K variant") has the amino acid sequence of:

(SEQ ID NO: 1)
MDSFNYTTPDYGHYDDKDTLDLNTPVDKTSNTLRVPDILALVIFAVVFLV

GVLGNALVVWVTAFEAKRTINAIWFLNLAVADFLSCLALPILFTSIVQHH

HWPFGGAACSILPSLILLNMYASILLLATISADRFLLVFKPIWCQNFRGA

GLAWIACAVAWGLALLLTIPSFLYRVVREEYFPPKVLCGVDYSHDKRRER

AVAIVRLVLGFLWPLLTLTICYTFILLRTWSRRATRSTKTLKVVVAVVAS

FFIFWLPYQVTGIMMSFLEPSSPTFLLLKKLDSLCVSFAYINCCINPIIY

VVAGQGFQGRLRKSLPSLLRNVLTEESVVRESKSFTRSTVDTMAQKTQAV

Two natural missense mutations of human C5aR are described ((http://www.uniprot.org/uniprot/P21730): Reference SNP (refSNP) Cluster Report: rs4467185 (MAF: 0.03) and Cluster Report: rs11880097 (MAF: 0.03). One mutation is located within the N-terminal extracellular region of human C5aR (Position 2 of SEQ ID NO: 1) resulting in a D to N substitution.

A human C5aR protein which comprises both natural missense mutations in its sequence (also referred to herein as the "N/N variant") has the amino acid sequence of:

(SEQ ID NO: 2)
MNSFNYTTPDYGHYDDKDTLDLNTPVDKTSNTLRVPDILALVIFAVVFLV

GVLGNALVVWVTAFEAKRTINAIWFLNLAVADFLSCLALPILFTSIVQHH

HWPFGGAACSILPSLILLNMYASILLLATISADRFLLVFKPIWCQNFRGA

GLAWIACAVAWGLALLLTIPSFLYRVVREEYFPPKVLCGVDYSHDKRRER

AVAIVRLVLGFLWPLLTLTICYTFILLRTWSRRATRSTKTLKVVVAVVAS

FFIFWLPYQVTGIMMSFLEPSSPTFLLLNKLDSLCVSFAYINCCINPIIY

VVAGQGFQGRLRKSLPSLLRNVLTEESVVRESKSFTRSTVDTMAQKTQAV

Cynomolgus monkey (*Macaca fascicularis*) C5aR has the amino acid sequence of:

(SEQ ID NO: 3)
MDPFSSTTLDYEHYDGKNVLDSDTPVDKTSNTLRVPDILALVVFAVVFLV

GVLGNALVVWVTAFEVKRTINAIWFLNLAVADFLSCLALPILFTSIVQHH

HWPFGGTACRILPSLILLNMYASILLLATISADRFLLVFNPIWCQNFRGA

GLAWIACAVAWGLALLLTIPSFLYRAVRQEEYSPKVLCGVDYNNDTRRER

AVAIVRLVLGFLWPLLTLMICYTFLLLRTWSRRATRSTKTLKVVVAVVAS

FFIFWLPYQVTGTMMSFLRPSSPTYLQLKKLDSLSISFAYINCCINPVIY

VVAGQGFQGRLRKSLPSLLRNVLTEESVVRESKSFTRSTVDTMTEKTQAV

Mouse (*Mus musculus*) C5aR has the amino acid sequence of (SEQ ID NO: 4)
MDPIDNSSFEINYDHYGTMAPNIPADGIHLPKRQPGDVAALIIYSVVFLV

GVPGNALVVWVTAFEARRAVNAIWFLNLAVADLLSCLALPVLFTTVLNHN

YWYFDATACIVLPSLILLNMYASILLLATISADRFLLVFKPIWCQKVRGT

GLAWMACGVAWVLALLLTIPSFVYREAYKDFYSEHTVCGINYGGGSFPKE

KAVAILRLMVGFVLPLLTLNICYTFLLLRTWSRKATRSTKTLKVVMAVVI

CFFIFWLPYQVTGVMIAWLPPSSPTLKRVEKLNSLCVSLAYINCCVNPII

YVMAGQGFHGRLLRSLPSIIRNALSEDSVGRDSKTFTPSTTDTSTRKSQA

V

Rat (*Rattus norvegicus*) C5aR has the amino acid sequence of (SEQ ID NO: 5)
MDPISNDSSEITYDYSDGTPNPDMPADGVYIPKMEPGDIAALIIYLAVFL

VGVTGNALVVWVTAFEAKRTVNAIWFLNLAVADLLSCLALPILFTSIVKH

NHWPFGDQACIVLPSLILLNMYSSILLLATISADRFLLVFKPIWCQKFRR

PGLAWMACGVTWVLALLLTIPSFVFRRIHKDPYSDSILCNIDYSKGPFFI

EKAIAILRLMVGFVLPLLTLNICYTFLLIRTWSRKATRSTKTLKVVMAVV

TCFFVFWLPYQVTGVILAWLPRSSSTFQSVERLNSLCVSLAYINCCVNPI

IYVMAGQGFHGRLRRSLPSIIRNVLSEDSLGRDSKSFTRSTMDTSTQKSQ

AV

The term "C5a" refers to a protein known as Human Complement Component C5a

Human C5a (Uniprot: P01031|678-751) has the amino acid sequence of:

(SEQ ID NO: 6)
TLQKKIEEIAAKYKHSVVKKCCYDGACVNNDETCEQRAARISLGPRCIKA

FTECCVVASQLRANISHKDMQLGR

The term "C5L2" refers to a protein known as C5a anaphylatoxin chemotactic receptor 2.

Human C5L2 has the amino acid sequence of:

(SEQ ID NO: 7)
MGNDSVSYEYGDYSDLSDRPVDCLDGACLAIDPLRVAPLPLYAAIFLVGV

PGNAMVAWVAGKVARRRVGATWLLHLAVADLLCCLSLPILAVPIARGGHW

PYGAVGCRALPSIILLTMYASVLLLAALSADLCFLALGPAWWSTVQRACG

VQVACGAAWTLALLLTVPSAIYRRLHQEHFPARLQCVVDYGGSSSTENAV

TAIRFLFGFLGPLVAVASCHSALLCWAARRCRPLGTAIVVGFFVCWAPYH

LLGLVLTVAAPNSALLARALRAEPLIVGLALAHSCLNPMLFLYFGRAQLR

RSLPAACHWALRESQGQDESVDSKKSTSHDLVSEMEV.

The term "C3aR" refers to a protein known as C3a anaphylatoxin chemotactic receptor.

Human C3aR has the amino acid sequence of:

(SEQ ID NO: 8)
MASFSAETNSTDLLSQPWNEPPVILSMVILSLTFLLGLPGNGLVLWVAGL

KMQRTVNTIWFLHLTLADLLCCLSLPFSLAHLALQGQWPYGRFLCKLIPS

IIVLNMFASVFLLTAISLDRCLVVFKPIWCQNHRNVGMACSICGCIWVVA

CVMCIPVFVYREIFTTDNHNRCGYKFGLSSSLDYPDFYGDPLENRSLENI

VQPPGEMNDRLDPSSFQTNDHPWTVPTVFQPQTFQRPSADSLPRGSARLT

SQNLYSNVFKPADVVSPKIPSGFPIEDHETSPLDNSDAFLSTHLKLFPSA

SSNSFYESELPQGFQDYYNLGQFTDDDQVPTPLVAITITRLVVGFLLPSV

IMIACYSFIVFRMQRGRFAKSQSKTFRVAVVVVAVFLVCWTPYHIFGVLS

LLTDPETPLGKTLMSWDHVCIALASANSCFNPPFLYALLGKDFRKKARQSI

QGILEAAFSEELTRSTHCPSNNVISERNSTTV

The term "FPR1" refers to a protein known as fMet-Leu-Phe receptor

Human FPR1 has the amino acid sequence of:

(SEQ ID NO: 9)
METNSSLPTNISGGTPAVSAGYLFLDIITYLVFAVTFVLGVLGNGLVIWV

AGFRMTHTVTTISYLNLAVADFCFTSTLPFFMVRKAMGGHWPFGWFLCKF

LFTIVDINLFGSVFLIALIALDRCVCVLHPVWTQNHRTVSLAKKVIIGPW

VMALLLTLPVIIRVTTVPGKTGTVACTFNFSPWTNDPKERINVAVAMLTV

RGIIRFIIGFSAPMSIVAVSYGLIATKIHKQGLIKSSPPLRVLSFVAAAF

FLCWSPYQVVALIATVRIRELLQGMYKEIGIAVDVTSALAFFNSCLNPML

YVFMGQDFRERLIHALPASLERALTEDSTQTSDTATNSTLPSAEVALQAK

The term "ChemR23" refers to a protein known as Chemokine-like receptor 1.
Human ChemR23 has the amino acid sequence of:

(SEQ ID NO: 10)
MRMEDEDYNTSISYGDEYPDYLDSIVVLEDLSPLEARVTRIFLVVVYSIV

CFLGILGNGLVIIATFKMKKTVNMVWFLNLAVADFLFNVFLPIHITYAA

MDYHWVFGTAMCKISNFLLIHNMFTSVFLLTIISSDRCISVLLPVWSQNH

RSVRLAYMACMVIWVLAFFLSSPSLVFRDTANLHGKISCFNNFSLSTPGS

SSWPTHSQMDPVGYSRHMVVTVTRFLCGFLVPVLIITACYLTIVCKLHRN

RLAKTKKPFKIIVTIIITFFLCWCPYHTLNLLELHHTAMPGSVFSLGLPL

ATALAIANSCMNPILYVFMGQDFKKFKVALFSRLVNALSEDTGHSSYPSH

RSFTKMSSMNERTSMNERETGML

The term "antibody" as used herein refers to a protein comprising at least two heavy (H) chains and two light (L) chains inter-connected by disulfide bonds, which interacts with an antigen. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology.

The phrase "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8:1057-1062; and U.S. Pat. No. 5,641,870).

A "human antibody" or "human antibody fragment", as used herein, is an antibody and antibody fragment having variable regions in which both the framework and CDR regions are from sequences of human origin. Human antibodies can also be isolated from synthetic libraries or from transgenic mice (e.g. Xenomouse) provided the respective system yield in antibodies having variable regions in which both the framework and CDR regions are derived from sequences of human origin. Furthermore, if the antibody contains a constant region, the constant region also is derived from such sequences. Human origin includes, e.g., human germline sequences, or mutated versions of human germline sequences or antibody containing consensus framework sequences derived from human framework sequences analysis, for example, as described in Knappik et al., (2000) J Mol Biol 296:57-86).

The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g. Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948.

A "humanized antibody" or "humanized antibody fragment" is defined herein as an antibody molecule, which has constant antibody regions derived from sequences of human origin and the variable antibody regions or parts thereof or only the CDRs are derived from another species. For example, a humanized antibody can be CDR-grafted, wherein the CDRs of the variable domain are from a non-human origin, while one or more frameworks of the variable domain are of human origin and the constant domain (if any) is of human origin.

The term "chimeric antibody" or "chimeric antibody fragment" is defined herein as an antibody molecule, which has constant antibody regions derived from, or corresponding to, sequences found in one species and variable antibody regions derived from another species. Preferably, the constant antibody regions are derived from, or corresponding to, sequences found in humans, and the variable antibody regions (e.g. VH, VL, CDR or FR regions) are derived from sequences found in a non-human animal, e.g. a mouse, rat, rabbit or hamster.

The term "isolated antibody" refers to an antibody or antibody fragment that is substantially free of other antibodies or antibody fragments having different antigenic specificities. Moreover, an isolated antibody or antibody fragment may be substantially free of other cellular material and/or chemicals. Thus, in some aspects, antibodies provided are isolated antibodies, which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "recombinant antibody", as used herein, includes all antibodies that are prepared, expressed, created or segregated by means not existing in nature. For example, antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences or antibodies isolated from an animal (e.g., a mouse) that is transgenic or transchromosomal for human immunoglobulin genes or a hybridoma prepared therefrom. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody. In an embodiment, the antibodies and antibody fragment disclosed herein are isolated from the HuCAL® library (Rothe et al, J. Mol. Biol. (2008) 376, 1182-1200).

As used herein, an antibody "binds specifically to", "specifically binds to", is "specific to/for" or "specifically recognizes" an antigen, such as human C5aR, if such antibody is able to discriminate between such antigen and one or more reference antigen(s), since binding specificity is not an absolute, but a relative property. For example, a standard ELISA assay can be carried out. The scoring may be carried out by standard color development (e.g. secondary antibody with horseradish peroxide and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like.

As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity.

The term "$K_D$", as used herein, refers to the dissociation constant, which is obtained from the ratio of $k_{off}$ to $K_{on}$ (i.e. $k_{off}/k_{on}$) and is expressed as a molar concentration (M). $K_D$ values for antigen binding moieties like e.g. monoclonal antibodies can be determined using methods well established in the art. Methods for determining the $K_D$ of an antigen binding moiety like e.g. a monoclonal antibody are SET (solution equilibrium titration) or surface plasmon resonance using a biosensor system such as a Biacore® system. In the present disclosure an antibody specific for C5aR typically has a dissociation rate constant ($K_D$) ($k_{off}/k_{on}$) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than $10^{-10}$M, less than $5\times10^{-11}$M, less than $10^{-11}$M, less than $5\times10^{-12}$M, less than $10^{-12}$M, less than $5\times10^{-13}$M, less than $10^{-3}$M, less than $5\times10^{-14}$M, less than $10^{-14}$M, less than $5\times10^{-15}$M, or less than $10$-$^{15}$M or lower.

The term "epitope" includes any proteinaceous region which is specifically recognized by an antibody or antibody fragment thereof or otherwise interacts with a molecule. Generally, epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

"Compositions" of the present disclosure may be used for therapeutic or prophylactic applications. The present disclosure, therefore, includes a pharmaceutical composition containing an antibody or antibody fragment as disclosed herein and a pharmaceutically acceptable carrier or excipient therefor. In a related aspect, the present disclosure provides a method for treating cancer. Such method contains the steps of administering to a subject in need thereof an effective amount of the pharmaceutical composition that contains an antibody or antibody fragment as described herein.

The present disclosure provides therapeutic methods comprising the administration of a therapeutically effective amount of an antibody or antibody fragment as disclosed herein to a subject in need of such treatment. A "therapeutically effective amount" or "effective amount", as used herein, refers to the amount of a C5aR antibody necessary to elicit the desired biological response. In accordance with the subject disclosure, the therapeutic effective amount is the amount of a C5aR antibody necessary to treat and/or prevent a disease.

"Administered" or "administration" includes but is not limited to delivery of a drug by an injectable form, such as, for example, an intravenous, intramuscular, intradermal or subcutaneous route or mucosal route, for example, as a nasal spray or aerosol for inhalation or as an ingestible solution, capsule or tablet. Preferably, the administration is by an injectable form.

As used herein, "treatment", "treat" or "treating" and the like refers to clinical intervention in an attempt to alter the natural course of a disease in the subject being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or antibody fragments according to the preset disclosure are used to delay development of a disease or to slow the progression of a disease.

The term "effector function" refers to those biological activities attributable to the Fc region of an antibody, which vary with the antibody isotype. Non-limiting examples of antibody effector functions include C1q binding and complement dependent cytotoxicity (CDC); Fc receptor binding and antibody-dependent cell-mediated cytotoxicity (ADCC) and/or antibody-dependent cellular phagocytosis (ADCP); down regulation of cell surface receptors (e.g. B cell receptor); and B cell activation.

"Antibody-dependent cell-mediated cytotoxicity" or "ADCC" refers to a form of cytotoxicity in which antibodies bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII.

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass) of the present disclosure, which are bound to their cognate antigen.

"Antibody-dependent cellular phagocytosis" or "ADCP" refers to a mechanism of elimination of antibody-coated target cells by internalization by phagocytic cells, such as macrophages or dendritic cells.

'Preventing' or 'prevention' refers to a reduction in risk of acquiring or developing a disease (i.e. causing at least one of the clinical symptoms of the disease not to develop in a subject that may be exposed to a disease-causing agent, or predisposed to the disease in advance of disease onset). "Prevention" also refers to methods which aim to prevent the onset of a disease or its symptoms or which delay the onset of a disease or its symptoms.

"Subject" or "species" or as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably, the subject is a primate, most preferably a human.

Throughout this specification, unless the context requires otherwise, the words "comprise", "have" and "include" and their respective variations such as "comprises", "comprising", "has", "having", "includes" and "including" will be understood to imply the inclusion of a stated element or integer or group of elements or integers but not the exclusion of any other element or integer or group of elements or integers.

The terms "engineered" or "modified" as used herein includes manipulation of nucleic acids or polypeptides by synthetic means (e.g. by recombinant techniques, in vitro peptide synthesis, by enzymatic or chemical coupling of peptides or some combination of these techniques). Preferably, the antibodies or antibody fragments according to the present disclosure are engineered or modified to improve one or more properties, such as antigen binding, stability, half-life, effector function, immunogenicity, safety and the like.

"Variant" as used herein refers to a polypeptide that differs from a reference polypeptide by one or more modifications for example amino acid substitutions, insertions or deletions.

The term "amino acid mutation" as used herein is meant to encompass amino acid substitutions, deletions, insertions, and modifications. Any combination of substitution, deletion, insertion, and modification can be made as long as the final construct possesses the desired characteristics, e.g., reduced binding to an Fc receptor. Amino acid sequence deletions and insertions include N- and/or C-terminal deletions and insertions of amino acid residues. Particular amino acid mutations are amino acid substitutions. Amino acid substitutions include replacement by non-naturally occurring amino acids or by naturally occurring amino acid derivatives of the twenty standard amino acids. Amino acid mutations can be generated using genetic or chemical methods well known in the art. Genetic methods may include site-directed mutagenesis, PCR, gene synthesis and the like. It is contemplated that methods of altering the side chain group of an amino acid residue by methods other than genetic engineering, such as chemical modification, may also be useful. Various designations may be used herein to indicate the same amino acid mutation. For example, a substitution from glycine at position 327 of the Fc region to alanine can be indicated as 237A, G337, G337A, or Gly329Ala.

The term "$EC_{50}$" as used herein, refers to the concentration of an antibody or antibody fragment or ligand, which induces a response in an assay half way between the baseline and maximum. It therefore represents the antibody or ligand concentration at which 50% of the maximal effect is observed The term "$IC_{50}$" as used herein, refers to the concentration of an antibody or antibody fragment that inhibits a response in an assay half way between the maximal response and the baseline. It represents the antibody concentration that reduces a given response by 50%.

The terms "inhibition" or "inhibit" or "reduction" or "reduce" or "neutralization" or "neutralize" refer to a decrease or cessation of any phenotypic characteristic (such as binding or a biological activity or function) or to the decrease or cessation in the incidence, degree, or likelihood of that characteristic. The "inhibition", "reduction" or "neutralization" needs not to be complete as long as it is detectable using an appropriate assay. In some embodiments, by "reduce" or "inhibit" or "neutralize" is meant the ability to cause a decrease of 20% or greater. In another embodiment, by "reduce" or "inhibit" or "neutralize" is meant the ability to cause a decrease of 50% or greater. In yet another embodiment, by "reduce" or "inhibit" or "neutralize" is meant the ability to cause an overall decrease of 75%, 85%, 90%, 95%, or greater.

The term "antagonistic" antibody as used herein refers to an antibody or antibody fragment that interacts with an antigen and partially or fully inhibits or neutralizes a biological activity or function or any other phenotypic characteristic of a target antigen.

A "wild-type" protein is a version or variant of the protein as it is found in nature. An amino acid sequence of a wildtype protein, e.g., a Fc region of an human IgG1 antibody, is the amino acid sequence of the protein as it occurs in nature. Due to allotypic differences, there can be more than one amino acid sequence for a wildtype protein. For example, there are several allotypes of naturally occurring human IgG1 heavy chain constant regions (see, e.g., Jeffries et al. (2009) mAbs 1:1).

The "Fc region" is used to define the C-terminal region of an immunoglobulin heavy chain. The Fc region of an immunoglobulin generally comprises two constant domains, a CH2 domain and a CH3 domain. Although the boundaries of the Fc region of an IgG heavy chain might vary slightly, the human IgG heavy chain Fc region is usually defined to extend from Cys226, or from Pro230, to the C-terminus of the heavy chain. However, the C-terminal lysine (Lys447) of the Fc region may or may not be present. Unless otherwise specified herein, numbering of amino acid residues in the Fc region is according to the EU numbering system, also called the EU index, as described in Kabat et al., Sequences of Proteins of Immunological Interest, 5th Ed. Public Health Service, National Institutes of Health, Bethesda, MD, 1991.

Embodiments

In an embodiment, the present disclosure refers to an isolated antibody or antibody fragment specific for human C5aR, wherein said antibody or antibody fragment comprises
- a) the HCDR1 region comprising the amino acid sequence of SEQ ID NO: 27, the HCDR2 region comprising the amino acid sequence of SEQ ID NO: 28, the HCDR3 region comprising the amino acid sequence of SEQ ID NO: 29, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34, or
- b) the HCDR1 region comprising the amino acid sequence of SEQ ID NO: 27, the HCDR2 region comprising the amino acid sequence of SEQ ID NO: 39, the HCDR3 region comprising the amino acid sequence of SEQ ID NO: 40, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34.

In an embodiment, the present disclosure refers to an isolated antibody or antibody fragment specific for human C5aR, wherein said antibody or antibody fragment comprises
- a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
- b) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, the present disclosure refers to an isolated antibody or antibody fragment specific for human C5aR, wherein said antibody or antibody fragment comprises
- a) the HCDR1 region comprising the amino acid sequence of SEQ ID NO: 30, the HCDR2 region comprising the amino acid sequence of SEQ ID NO: 31, the HCDR3 region comprising the amino acid sequence of SEQ ID NO: 29, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34, or
- b) the HCDR1 region comprising the amino acid sequence of SEQ ID NO: 30, the HCDR2 region comprising the amino acid sequence of SEQ ID NO: 41, the HCDR3 region comprising the amino acid sequence of SEQ ID NO: 40, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34.

In an embodiment, the present disclosure refers to an isolated antibody or antibody fragment specific for human C5aR, wherein said antibody or antibody fragment comprises
- a) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
- b) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, the present disclosure refers to an isolated antibody or antibody fragment specific for human C5aR, wherein said antibody or antibody fragment comprises
- a) the HCDR1 region comprising the amino acid sequence of SEQ ID NO: 27, the HCDR2 region comprising the amino acid sequence of SEQ ID NO: 28, the HCDR3 region comprising the amino acid sequence of SEQ ID NO: 29, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34, or
- b) the HCDR1 region comprising the amino acid sequence of SEQ ID NO: 30, the HCDR2 region comprising the amino acid sequence of SEQ ID NO: 31, the HCDR3 region comprising the amino acid sequence of SEQ ID NO: 29, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34, or
- c) the HCDR1 region comprising the amino acid sequence of SEQ ID NO: 27, the HCDR2 region comprising the amino acid sequence of SEQ ID NO: 39, the HCDR3 region comprising the amino acid sequence of SEQ ID NO: 40, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34, or
- d) the HCDR1 region comprising the amino acid sequence of SEQ ID NO: 30, the HCDR2 region comprising the amino acid sequence of SEQ ID NO: 41, the HCDR3 region comprising the amino acid sequence of SEQ ID NO: 40, the LCDR1 region comprising the amino acid sequence of SEQ ID NO: 32, the LCDR2 region comprising the amino acid sequence of SEQ ID NO: 33 and the LCDR3 region comprising the amino acid sequence of SEQ ID NO: 34.

In an embodiment, the present disclosure refers to an isolated antibody or antibody fragment specific for human C5aR, wherein said antibody or antibody fragment comprises
  a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
  b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
  c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
  d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, the present disclosure refers to an isolated antibody or antibody fragment specific for human C5aR, wherein said antibody or antibody fragment comprises the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34.

In an embodiment, the present disclosure refers to an isolated antibody or antibody fragment specific for human C5aR, wherein said antibody or antibody fragment comprises the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, the present disclosure refers to an isolated antibody or antibody fragment specific for human C5aR, wherein said antibody or antibody fragment comprises the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34.

In an embodiment, the present disclosure refers to an isolated antibody or antibody fragment specific for human C5aR, wherein said antibody or antibody fragment comprises the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, the present disclosure refers to an isolated antibody or antibody fragment specific for human C5aR comprising 6 CDRs defined by Kabat of any one of the antibodies disclosed in Table 1 or Table 2.

In an embodiment, the present disclosure refers to an isolated antibody or antibody fragment specific for human C5aR comprising 6 CDRs defined by Chothia of any one of the antibodies disclosed in Table 1 or Table 2.

In an embodiment of the present disclosure, the isolated antibody or antibody fragment is a monoclonal antibody or antibody fragment. In an embodiment of the present disclosure, the isolated antibody or antibody fragment is a human, humanized or chimeric antibody or antibody fragment. In another embodiment of the present disclosure, the isolated antibody or antibody fragment is recombinant antibody or antibody fragment. In an embodiment of the present disclosure, the isolated antibody or antibody fragment is of the IgG isotype. In an embodiment of the present disclosure, the isolated antibody or antibody fragment is of the IgG1 class. In another embodiment of the present disclosure, the isolated antibody or antibody fragment does not substantially induce effector function in vitro.

In an embodiment, the present disclosure refers to an isolated antibody or antibody fragment specific for human C5aR, wherein said antibody or antibody fragment comprises
  a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34 and further comprises the VH of SEQ ID NO: 35 or the VL of SEQ ID NO: 36, or
  b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34 and further comprises the VH of SEQ ID NO: 35 or the VL of SEQ ID NO: 36, or
  c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34 and further comprises the VH of SEQ ID NO: 42 or the VL of SEQ ID NO: 43, or
  d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34 and further comprises the VH of SEQ ID NO: 42 or the VL of SEQ ID NO: 43.

In an embodiment, the present disclosure refers to an isolated antibody or antibody fragment specific for human C5aR, wherein said antibody or antibody fragment comprises
  a) the VH of SEQ ID NO: 35 and the VL of SEQ ID NO: 36 or
  b) the VH of SEQ ID NO: 42 and the VL of SEQ ID NO: 43.

In an embodiment, the present disclosure refers to an isolated antibody or antibody fragment specific for human C5aR, wherein said antibody or antibody fragment comprises the VH of SEQ ID NO: 35 and the VL of SEQ ID NO: 36.

In an embodiment, the present disclosure refers to an isolated antibody or antibody fragment specific for human C5aR, wherein said antibody or antibody fragment comprises the VH of SEQ ID NO: 42 and the VL of SEQ ID NO: 43.

In an embodiment, the present disclosure refers to an isolated antibody or antibody fragment specific for human C5aR, wherein said antibody or antibody fragment comprises the HC of SEQ ID NO: 37 and the LC of SEQ ID NO: 38.

In an embodiment, the present disclosure refers to an isolated antibody or antibody fragment specific for human C5aR, wherein said antibody or antibody fragment comprises the HC of SEQ ID NO: 44 and the LC of SEQ ID NO: 45.

In an embodiment, the present disclosure refers to an isolated_antibody or antibody fragment specific for human C5aR comprising the variable heavy chain (VH) and the variable light chain (VL) of any one of the antibodies disclosed in Table 1 or Table 2.

In an embodiment, the present disclosure refers to an isolated antibody or antibody fragment specific for human C5aR comprising the heavy chain (HC) and the light chain (LC) of any one of the antibodies disclosed in Table 1 or Table 2.

In an embodiment, the present disclosure refers to an isolated antibody or antibody fragment specific for human C5aR, wherein said antibody or antibody fragment comprises the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34 and further comprises the VH of SEQ ID NO: 35 or the VL of SEQ ID NO: 36

In an embodiment, the present disclosure refers to an isolated antibody or antibody fragment specific for human C5aR, wherein said antibody or antibody fragment comprises the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34 and further comprises the VH of SEQ ID NO: 42 or the VL of SEQ ID NO: 43

In an embodiment, the present disclosure refers to an isolated antibody or antibody fragment specific for human C5aR, wherein said antibody or antibody fragment comprises the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34 and further comprises the VH of SEQ ID NO: 35 or the VL of SEQ ID NO: 36

In an embodiment, the present disclosure refers to an isolated antibody or antibody fragment specific for human C5aR, wherein said antibody or antibody fragment comprises the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34 and further comprises the VH of SEQ ID NO: 42 or the VL of SEQ ID NO: 43.

In an embodiment of the present disclosure, the isolated antibody or antibody fragment is a monoclonal antibody or antibody fragment. In an embodiment of the present disclosure, the isolated antibody or antibody fragment is a human, humanized or chimeric antibody or antibody fragment. In another embodiment of the present disclosure, the isolated antibody or antibody fragment is recombinant antibody or antibody fragment.

In an embodiment, the present disclosure refers to an isolated antibody or antibody fragment specific for human C5aR, wherein said antibody or antibody fragment comprises
  a) the VH of SEQ ID NO: 35 and the VL of SEQ ID NO: 36 or
  b) the VH of SEQ ID NO: 42 and the VL of SEQ ID NO: 43 or
  a VH and a VL that has at least at 80%, at least 85%, at least 90% or at least 95% identity to the VH of SEQ ID NO: 35 or SEQ ID NO: 42 and to the VL of SEQ ID NO: 36 or SEQ ID NO: 43.

In an embodiment, the present disclosure refers to an isolated antibody or antibody fragment specific for human C5aR, wherein said antibody or antibody fragment comprises the VH of SEQ ID NO: 35 and the VL of SEQ ID NO: 36, or a VH and a VL that has at least at 80%, at least 85%, at least 90% or at least 95% identity to the VH of SEQ ID NO: 35 and to the VL of SEQ ID NO: 36.

In an embodiment, the present disclosure refers to an isolated antibody or antibody fragment specific for human C5aR, wherein said antibody or antibody fragment comprises the VH of SEQ ID NO: 42 and the VL of SEQ ID NO: 43, or a VH and a VL that has at least at 80%, at least 85%, at least 90% or at least 95% identity to the VH of SEQ ID NO: 42 and to the VL of SEQ ID NO: 43.

In an embodiment, the present disclosure refers to an isolated antibody or antibody fragment specific for human C5aR, wherein said antibody or antibody fragment comprises
  a) the HC of SEQ ID NO: 37 and the LC of SEQ ID NO: 38 or
  b) the HC of SEQ ID NO: 44 and the LC of SEQ ID NO: 45 or
  a HC and a LC that has at least at 80%, at least 85%, at least 90% or at least 95% identity to the HC of SEQ ID NO: 37 or SEQ ID NO: 44 and to the LC of SEQ ID NO:38 or SEQ ID NO: 45.

In an embodiment, the present disclosure refers to an isolated antibody or antibody fragment specific for human C5aR, wherein said antibody or antibody fragment comprises the HC of SEQ ID NO: 37 and the LC of SEQ ID NO: 38 or a HC and a LC that has at least at 80%, at least 85%, at least 90% or at least 95% identity to the HC of SEQ ID NO: 37 and to the LC of SEQ ID NO: 38.

In an embodiment, the present disclosure refers to an isolated antibody or antibody fragment specific for human C5aR, wherein said antibody or antibody fragment comprises the HC of SEQ ID NO: 44 and the LC of SEQ ID NO: 45 or a HC and a LC that has at least at 80%, at least 85%, at least 90% or at least 95% identity to the HC of SEQ ID NO: 44 and to the LC of SEQ ID NO: 45.

In an embodiment of the present disclosure, the isolated antibody or antibody fragment is a monoclonal antibody or antibody fragment. In an embodiment of the present disclosure, the isolated antibody or antibody fragment is a human, humanized or chimeric antibody or antibody fragment. In another embodiment of the present disclosure, the isolated antibody or antibody fragment is recombinant antibody or antibody fragment. In an embodiment, said isolated antibody or an antibody fragment is a human or humanized antibody or antibody fragment. In one embodiment, said isolated antibody or an antibody fragment is a human antibody or antibody fragment.

In an embodiment, the isolated antibody or antibody fragment specific for human C5aR of the present disclosure is a recombinant or synthetic antibody or antibody fragment. In a further embodiment, the isolated antibody or antibody fragment specific for C5aR according to the present disclosure is an isolated recombinant monoclonal antibody or antibody fragment. In a further embodiment, the isolated antibody or antibody fragment specific for C5aR according to the present disclosure is an isolated recombinant monoclonal human antibody or antibody fragment.

In an embodiment, the isolated antibody or antibody fragment specific for C5aR according to the present disclosure is of the IgG isotype. In another embodiment, said isolated antibody or antibody fragment is of the IgG1 class. In another embodiment, said isolated antibody or antibody fragment is of the human IgG1 class.

Nucleic Acids

In an embodiment, the present disclosure refers to a nucleic acid composition comprising a nucleic acid sequence or a plurality of nucleic acid sequences encoding an isolated antibody or antibody fragment specific for human C5aR, wherein said isolated said antibody or antibody fragment comprise
- a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
- b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
- c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
- d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In another embodiment, the present disclosure refers to a nucleic acid composition comprising a nucleic acid sequence or a plurality of nucleic acid sequences encoding the heavy chain sequence and light chain sequence of an isolated antibody or antibody fragment specific for human C5aR, wherein the nucleic acid sequence or a plurality of nucleic acid sequences comprises
- a) the HCDR1 region of SEQ ID NO: 46, the HCDR2 region of SEQ ID NO: 47, the HCDR3 region of SEQ ID NO: 48, the LCDR1 region of SEQ ID NO: 51, the LCDR2 region of SEQ ID NO: 52 and the LCDR3 region of SEQ ID NO: 53, or
- b) the HCDR1 region of SEQ ID NO: 49, the HCDR2 region of SEQ ID NO: 50, the HCDR3 region of SEQ ID NO: 48, the LCDR1 region of SEQ ID NO: 51, the LCDR2 region of SEQ ID NO: 52 and the LCDR3 region of SEQ ID NO: 53, or
- c) the HCDR1 region of SEQ ID NO: 58, the HCDR2 region of SEQ ID NO: 59, the HCDR3 region of SEQ ID NO: 60, the LCDR1 region of SEQ ID NO: 63, the LCDR2 region of SEQ ID NO: 64 and the LCDR3 region of SEQ ID NO: 65, or
- d) the HCDR1 region of SEQ ID NO: 61, the HCDR2 region of SEQ ID NO: 62, the HCDR3 region of SEQ ID NO: 60, the LCDR1 region of SEQ ID NO: 63, the LCDR2 region of SEQ ID NO: 64 and the LCDR3 region of SEQ ID NO: 65.

In another embodiment, the present disclosure refers to a nucleic acid composition comprising a nucleic acid sequence or a plurality of nucleic acid sequences encoding the heavy chain sequence and light chain sequence of an isolated antibody or antibody fragment specific for human C5aR, wherein the nucleic acid sequence or a plurality of nucleic acid sequences comprise
- a) the HCDR1 region of SEQ ID NO: 70, the HCDR2 region of SEQ ID NO: 71, the HCDR3 region of SEQ ID NO: 72, the LCDR1 region of SEQ ID NO: 75, the LCDR2 region of SEQ ID NO: 76 and the LCDR3 region of SEQ ID NO: 77, or
- b) the HCDR1 region of SEQ ID NO: 73, the HCDR2 region of SEQ ID NO: 74, the HCDR3 region of SEQ ID NO: 72, the LCDR1 region of SEQ ID NO: 75, the LCDR2 region of SEQ ID NO: 76 and the LCDR3 region of SEQ ID NO: 77, or
- c) the HCDR1 region of SEQ ID NO: 82, the HCDR2 region of SEQ ID NO: 83, the HCDR3 region of SEQ ID NO: 84, the LCDR1 region of SEQ ID NO: 87, the LCDR2 region of SEQ ID NO: 88 and the LCDR3 region of SEQ ID NO: 89, or
- d) the HCDR1 region of SEQ ID NO: 85, the HCDR2 region of SEQ ID NO: 86, the HCDR3 region of SEQ ID NO: 84, the LCDR1 region of SEQ ID NO: 87, the LCDR2 region of SEQ ID NO: 88 and the LCDR3 region of SEQ ID NO: 89.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the VH of SEQ ID NO: 54 and the VL of SEQ ID NO: 55, or a VH and a VL that has at least 60%, at least 70%, at least 80%, at least 85%, at least 90% or at least 95% identity to the VH of SEQ ID NO: 54 and/or the VL of SEQ ID NO: 55.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the VH of SEQ ID NO: 66 and the VL of SEQ ID NO: 67, or a VH and a VL that has at least 60%, at least 70%, at least 80%, at least 85%, at least 90% or at least 95% identity to the VH of SEQ ID NO: 66 and/or the VL of SEQ ID NO: 67.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the VH of SEQ ID NO: 78 and the VL of SEQ ID NO: 79, or a VH and a VL that has at least 60%, at least 70%, at least 80%, at least 85%, at least 90% or at least 95% identity to the VH of SEQ ID NO: 78 and/or the VL of SEQ ID NO: 79.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the VH of SEQ ID NO: 90 and the VL of SEQ ID NO: 91, or a VH and a VL that has at least 60%, at least 70%, at least 80%, at least 85%, at least 90% or at least 95% identity to the VH of SEQ ID NO: 90 and/or the VL of SEQ ID NO: 91.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the HC of SEQ ID NO: 56 and the LC of SEQ ID NO: 57, or a HC and a LC that has at least 60%, at least 70%, at least 80%, at least 85%, at least 90% or at least 95% identity to the HC of SEQ ID NO: 56 and/or the LC of SEQ ID NO: 57.

In an embodiment, the present disclosure refers to an nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the HC of SEQ ID NO: 68 and the LC of SEQ ID NO: 69, or a HC and a LC that has at least 60%, at least 70%, at least 80%, at least 85%, at least 90% or at least 95% identity to the HC of SEQ ID NO: 68 and/or the LC of SEQ ID NO: 69.

In an embodiment, the present disclosure refers to an nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the HC of SEQ ID NO: 80 and the LC of SEQ ID NO: 81, or a HC and a LC that has at least 60%, at least 70%, at least 80%, at least 85%, at least 90% or at least 95% identity to the HC of SEQ ID NO: 80 and/or the LC of SEQ ID NO: 81.

In an embodiment, the present disclosure refers to an nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the HC of SEQ ID NO: 92 and the LC of SEQ ID NO: 93, or a HC and a LC that has at least 60%, at least 70%, at least 80%, at least 85%, at least 90% or at least 95% identity to the HC of SEQ ID NO: 92 and/or the LC of SEQ ID NO: 93.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the HC of SEQ ID NO: 56 and the LC of SEQ ID NO: 57.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the HC of SEQ ID NO: 68 and the LC of SEQ ID NO: 69.

In an embodiment, the present disclosure refers to a nucleic acid composition comprising a nucleic acid sequence or a plurality of nucleic acid sequences encoding an isolated antibody or antibody fragment specific for human C5aR, wherein said nucleic acid sequence or plurality of nucleic acid sequences comprise the HC of SEQ ID NO: 80 and the LC of SEQ ID NO: 81.

In an embodiment, the present disclosure refers to an nucleic acid composition comprising a nucleic acid sequence or a plurality of nucleic acid sequences encoding an antibody or antibody fragment specific for human C5aR disclosed herein, wherein said nucleic acid sequence or plurality of nucleic acid sequences comprise the HC of SEQ ID NO: 92 and the LC of SEQ ID NO: 93.

In another embodiment, the present disclosure refers to a nucleic acid composition comprising a nucleic acid sequence or a plurality of nucleic acid sequences encoding an isolated antibody or fragment specific for human C5aR, wherein the nucleic acid sequence or the plurality of nucleic acid sequences comprise the VH and VL of any one of the antibodies disclosed in Table 1 or Table 2.

In an embodiment, the present disclosure provides an isolated antibody or antibody fragment specific for human C5aR, encoded by any one of the nucleic acid sequences or plurality of nucleic acid sequences disclosed in Table 1 or Table 2.

In an embodiment, the present disclosure provides a nucleic acid composition comprising a nucleic acid sequence or a plurality of nucleic acid sequences encoding any one of the isolated antibodies or antibody fragments disclosed in Table 1 or Table 2.

In an embodiment, the present disclosure provides a nucleic acid composition comprising a nucleic acid sequence or a plurality of nucleic acid sequences encoding any one of the isolated antibodies or antibody fragments specific for human C5aR according to the present disclosure.

In another embodiment, the present disclosure refers to a nucleic acid composition comprising a nucleic acid sequence or a plurality of nucleic acid sequences encoding an isolated antibody or antibody fragment specific for human C5aR, wherein the nucleic acid sequence or the plurality of nucleic acid sequences comprises a HC and a LC of any one of the antibodies or antibody fragments disclosed in Table 1 or Table 2.

In an embodiment, said nucleic acid composition and/or said_nucleic acid sequence and/or plurality of nucleic acid sequences are isolated.

Vectors

In an embodiment, the present disclosure provides a vector composition comprising a vector or a plurality of vectors comprising a nucleic acid composition comprising a nucleic acid sequence or a plurality of nucleic acid sequences encoding an isolated antibody or antibody fragment specific for human C5aR according to the present disclosure.

In an embodiment, the present disclosure provides a vector composition comprising a vector or a plurality of vectors comprising a nucleic acid composition comprising a nucleic acid sequence or a plurality of nucleic acid sequences encoding any one of the isolated antibodies or antibody fragments specific for human C5aR disclosed in Tables 1 or Table 2.

In an embodiment, the present disclosure provides a vector composition comprising a vector or a plurality of vectors comprising a nucleic acid sequence or a plurality of nucleic acid sequences disclosed in Table 1 or Table 2.

In an embodiment, said vector composition and/or vector and/or plurality of vectors are isolated.

Host Cells

In an embodiment, the present disclosure provides a host cell comprising a vector composition comprising a vector or a plurality of vectors comprising a nucleic acid composition comprising a nucleic acid sequence or a plurality of nucleic acid sequences encoding an isolated antibody or antibody fragment specific for human C5aR according to the present disclosure.

In an embodiment, the present disclosure refers to a host cell comprising a vector composition comprising a vector or a plurality of vectors comprising a nucleic acid composition comprising a nucleic acid sequence or a plurality of nucleic acid sequences encoding an isolated antibody or antibody fragment specific for C5aR disclosed in Table 1 or Table 2.

In an embodiment, the host cell according to the present disclosure is able to express the isolated antibody or antibody fragment specific for human C5aR encoded by the vector composition or the nucleic acid composition.

In a further embodiment, the host cell is an isolated host cell. In a further embodiment, said host cell is a mammalian cell. In an embodiment, said mammalian cell is a human cell. In another embodiment, said mammalian cell is a CHO cell. In an embodiment, said cell is a HEK cell. In another embodiment, said cell is a PERC.6 cell. In an embodiment, said cell is a HKB11 cell.

The skilled man will realize that the nucleic acid sequence or the plurality of nucleic acid sequences encoding the heavy and/or light chain of an antibody or antibody fragment of the present disclosure can be cloned into different vectors or into the same vector.

The vectors can be introduced into the appropriate host cells such as prokaryotic (e.g., bacterial) or eukaryotic (e.g., yeast or mammalian) cells by methods well known in the art (see e.g., "Current Protocol in Molecular Biology", Ausubel et al. (eds.), Greene Publishing Assoc. and John Wiley Interscience, New York, 1989 and 1992). Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the nucleic acid sequence encoding the desired protein is transcribed into RNA in the host cell transformed by a vector containing this expression construction. The coding sequence may or may not contain a signal peptide or leader sequence. Upon expression in host cells, the antibodies or antibody fragments of the present disclosure are obtained. These steps can be achieved in different ways, as will be known by the person skilled in the art. In general, such steps typically include transforming or transfecting a suitable host cell with a nucleic acid composition or vector composition or an infectious particle, which encodes the antibody, or antibody fragments. Further, such steps typically include culturing said host cells under conditions suitable for the proliferation (multiplication, growth) of said host cells and a culturing step under conditions suitable for the production (expression, synthesis) of the encoded antibody or antibody fragment. The culturing of host cells under conditions suitable for proliferation or expression is typically accomplished in the presence of media comprising components suitable for cell growth or induction of expression. In particular, embodiments, the methods for the production of the antibodies or antibody fragments of the present disclosure further comprise the step of isolating and purifying the produced antibody or antibody fragment from the host cells or medium. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art. The antibody or antibody fragment of the present disclosure can then be purified by a number of techniques as known to the person skilled in the art.

In an embodiment, the present disclosure refers to a method of producing an isolated antibody or antibody fragment specific for human C5aR of any of the antibodies disclosed in Table 1 or Table 2. In an embodiment, a method of producing an isolated antibody or antibody fragment according to the present disclosure is provided, wherein the method comprises culturing a host cell comprising a vector composition comprising a vector or a plurality of vectors comprising a nucleic acid composition comprising a nucleic acid sequence or a plurality of nucleic acid sequences encoding an antibody or antibody fragment according to the present disclosure, under conditions suitable for expression of the antibody or antibody fragment, and isolating the antibody or antibody fragment from the host cell or host cell culture medium. An antibody or antibody fragment isolated as described herein may be purified techniques know in the art, such as high performance liquid chromatography (HPLC), ion exchange chromatography, gel electrophoresis, affinity chromatography, size exclusion chromatography, and the like. The conditions used to purify a particular antibody or antibody fragment will depend, in part, on factors such as net charge, hydrophobicity, hydrophilicity etc., and will be apparent to those having skill in the art. For affinity chromatography purification an antibody, ligand, receptor or antigen can be used to which the antibody or antibody fragment binds. For example, for affinity chromatography purification of antibody or antibody fragment according to the present disclosure, a matrix with protein A or protein G may be used. The purity of an antibody or antibody fragment can be determined by any of a variety of well-known analytical methods including gel electrophoresis, high-pressure liquid chromatography, and the like.

Specificity

In an embodiment, the present disclosure pertains to an isolated antibody or antibody fragment specific for human C5aR disclosed in Table 1 or Table 2. In an embodiment, the isolated antibody or antibody fragment according to the present disclosure is specific for human C5aR.

In an embodiment, the isolated antibody or antibody fragment according to the present disclosure is specific for human C5aR encoded by the amino acid sequence of SEQ ID NO: 1 and/or SEQ ID NO: 2. In an embodiment, the isolated antibody or antibody fragment according to the present disclosure is specific for a polypeptide_comprising_the amino acid sequence of SEQ ID NO: 1 and/or SEQ ID NO: 2. In an embodiment, the isolated antibody or antibody fragment according to the present disclosure is specific for a polypeptide consisting of_the amino acid sequence of SEQ ID NO: 1 and/or SEQ ID NO: 2.

In an embodiment, the isolated antibody or antibody fragment according to the present disclosure specifically binds to the extracellular region human C5aR. In an embodiment, the isolated antibody or antibody fragment according to the present disclosure specifically binds to the N-terminal extracellular region of human C5aR. In an embodiment, the isolated antibody or antibody fragment according to the present disclosure specifically binds to the N-terminal extracellular region of human C5aR, wherein the N-terminal extracellular region comprises the amino acid sequence of SEQ ID NO: 13. In an embodiment, the isolated antibody or antibody fragment according to the present disclosure specifically binds to the N-terminus of human C5aR comprising the amino acid sequence of SEQ ID NO: 13. In an embodiment, the isolated antibody or antibody fragment according to the present disclosure specifically binds to a peptide comprising the amino acid sequence of SEQ ID NO: 13. In an embodiment, the isolated antibody or antibody fragment according to the present disclosure specifically binds to a peptide consisting of the amino acid sequence of SEQ ID NO: 13.

In an embodiment, the said isolated antibody or antibody fragment specific for human C5aR, comprises
 a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR comprises
a) the VH of SEQ ID NO: 35 and the VL of SEQ ID NO: 36 or
b) the VH of SEQ ID NO: 42 and the VL of SEQ ID NO: 43 or
a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises
a) the HC of SEQ ID NO: 37 and the LC of SEQ ID NO: 38 or
b) the HC of SEQ ID NO: 44 and the LC of SEQ ID NO: 45 or
a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment specific for human C5aR is a human, humanized or chimeric antibody or antibody fragment. In an embodiment, said isolated antibody or antibody fragment specific for human C5aR is a recombinant antibody or antibody fragment. In an embodiment, said isolated antibody or antibody fragment specific for human C5aR is an isolated recombinant human monoclonal antibody or antibody fragment.

Species Cross-Reactivity

In further embodiments, the isolated antibody or antibody fragment according to the present disclosure is cross-reactive to cynomolgus monkey (cynomolgus) C5aR. In another embodiment, the isolated antibody or antibody fragment according to the present disclosure is specific for human C5aR and cynomolgus C5aR.

In an embodiment, the present disclosure refers to an isolated antibody or antibody fragment specific for human C5aR, wherein said antibody or antibody fragment cross-reactively binds to cynomolgus C5aR. In an embodiment, the isolated antibody or antibody fragment according to the present disclosure specifically binds to the extracellular region of human C5aR and cynomolgus C5aR. In an embodiment, the isolated antibody or antibody fragment according to the present disclosure binds to the N-terminal extracellular region of human C5aR and cynomolgus C5aR. In an embodiment, the isolated antibody or antibody fragment according to the present disclosure binds to the N-terminal extracellular region of human C5aR and cynomolgus C5aR, wherein the N-terminal extracellular region of C5aR comprises the amino acid sequence of SEQ ID NO: 13 or SEQ ID NO: 14.

In yet another embodiment, the isolated antibody or antibody fragment according to the present disclosure does not bind to rodent C5aR, such as mouse or rat C5aR.

In an embodiment, the antibody or antibody fragment according to the present disclosure binds to a peptide comprising the amino acid sequence of SEQ ID NO: 13 and/or SEQ ID NO: 14.

In an embodiment, the antibody or antibody fragment according to the present disclosure binds to a peptide consisting of the amino acid sequence of SEQ ID NO: 13 and/or SEQ ID NO: 14.

In an embodiment, said isolated antibody or antibody fragment specific for human C5aR and cynomolgus C5aR, comprises
a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR comprises
a) the VH of SEQ ID NO: 35 and the VL of SEQ ID NO: 36 or
b) the VH of SEQ ID NO: 42 and the VL of SEQ ID NO: 43 or
a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises
a) the HC of SEQ ID NO: 37 and the LC of SEQ ID NO: 38 or
b) the HC of SEQ ID NO: 44 and the LC of SEQ ID NO: 45 or
a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Monovalent Affinity for C5aR Peptides

In further embodiments, the present disclosure refers to an isolated antibody or antibody fragment specific for human C5aR, wherein said antibody or antibody fragment has a monovalent affinity for a human C5aR peptide comprising SEQ ID NO: 13 with a $K_D$ of 100 nM or less, such as 90 nM or less, 80 nM or less, 70 nM or less, 60 nM or less, 50 nM or less, 40 nM or less, 30 nM or less, 20 nM or less, 10 nM or less, 5 nM or 1 nM less.

In an embodiment, said monovalent affinity is determined in IgG format. In certain embodiments, said monovalent affinity is determined by surface plasmon resonance (SPR) as described herein in Example 4.

In an embodiment, said isolated antibody or antibody fragment specific for human C5aR, comprises
  a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
  b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
  c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
  d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR comprises
  a) the VH of SEQ ID NO: 35 and the VL of SEQ ID NO: 36 or
  b) the VH of SEQ ID NO: 42 and the VL of SEQ ID NO: 43 or
    a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises
  a) the HC of SEQ ID NO: 37 and the LC of SEQ ID NO: 38 or
  b) the HC of SEQ ID NO: 44 and the LC of SEQ ID NO: 45 or
    a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Apparent Affinity (Bivalent) for C5aR Peptides

In an embodiment, the present disclosure refers to an isolated antibody or antibody fragment specific for human C5aR, wherein said isolated antibody has an apparent affinity for a human C5aR peptide comprising SEQ ID NO: 13 with a $K_D$ of 1 nM or less, such as 0.5 nM or less, 0.4 nM or less, 0.3 nM or less, 0.2 nM or less, 0.1 nM or less, 90 pM or less, 80 pM or less, 70 pM or less, 60 pM or less, 50 pM or less, 40 pM or less, 30 pM or less, 20 pM or less, 10 pM or less, 5 pM or less or 1 pM or less.

In an embodiment, the present disclosure refers to an isolated antibody or antibody fragment specific for human C5aR, wherein said isolated antibody has an apparent affinity for a cynomolgus C5aR peptide comprising SEQ ID NO: 14 with a $K_D$ of 300 nM or less, such as 250 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 10 nM or 1 nM or less.

In an embodiment, the present disclosure refers to an isolated antibody or antibody fragment specific for human C5aR, wherein said isolated antibody has an apparent affinity to a human C5aR peptide comprising SEQ ID NO: 13 with a $K_D$ of 0.3 nM or less and to a cynomolgus C5aR peptide comprising SEQ ID NO: 14 with a $K_D$ of 150 nM or less.

In an embodiment, the present disclosure refers to an isolated antibody or antibody fragment specific for human C5aR, wherein said isolated antibody has an apparent_affinity for a human C5aR peptide comprising SEQ ID NO: 13 with a $K_D$ of 0.05 nM or less and for a cynomolgus C5aR peptide comprising SEQ ID NO: 14 with a $K_D$ of 80 nM or less.

In certain embodiments, said apparent affinity is determined in IgG format. In an embodiment, said apparent affinity is determined by biolayer interferometry (BLI) as described herein in Example 5.

In an embodiment, said isolated antibody or antibody fragment specific for human C5aR, comprises
  a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
  b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
  c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
  d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR comprises
  a) the VH of SEQ ID NO: 35 and the VL of SEQ ID NO: 36 or
  b) the VH of SEQ ID NO: 42 and the VL of SEQ ID NO: 43 or
    a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises
  a) the HC of SEQ ID NO: 37 and the LC of SEQ ID NO: 38 or
  b) the HC of SEQ ID NO: 44 and the LC of SEQ ID NO: 45 or a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Apparent Affinity (Bivalent) for Full-Length C5aR

In further embodiments, the present disclosure refers to an isolated antibody or antibody fragment specific for human C5aR, wherein said isolated antibody has an apparent affinity for human C5aR with a $K_D$ of 10 nM or less, such as 5 nM or less, 4 nM or less, 3 nM or less, 2 nM or less, 1 nM or less, 0.5 nM or less, 0.4 nM or less, 0.3 nM or less, 0.2 nM or less or 0.1 nM or less.

In embodiments, the present disclosure refers to an isolated antibody or antibody fragment specific for human C5aR, wherein said isolated antibody has an apparent_affinity for cynomolgus C5aR with a $K_D$ of 10 nM or less, such as 9 nM or less, 8 nM or less, 7 nM or less, 6 nM or less, 5 nM or less, 4 nM or less, 3 nM or less, or 1 nM or less.

In an embodiment, the present disclosure refers to an isolated antibody or antibody fragment specific for human C5aR, wherein said isolated antibody has an apparent affinity to human C5aR with a $K_D$ of 0.5 nM or less and to cynomolgus C5aR with a $K_D$ of 5 nM or less.

In an embodiment, said human C5aR comprises the amino acid sequence of SEQ ID NO: 1. In an embodiment, said human C5aR comprises the amino acid sequence of SEQ ID NO: 2. In an embodiment, said cynomolgus C5aR comprises the amino acid sequence of SEQ ID NO: 3.

In certain embodiments, said apparent affinity is determined in IgG format. In embodiments, said human C5aR or cynomolgus C5aR is expressed on cells. In embodiments, said human C5aR or cynomolgus C5aR is expressed on engineered CHO cells expressing full-length human. In embodiments, said CHO cells are Flp-In™ CHO cells.

In certain embodiments, said apparent affinity is determined as described herein in Example 6.

In an embodiment, said isolated antibody or antibody fragment specific for human C5aR, comprises
  a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
  b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region comprising the amino acid sequence of SEQ ID NO: 34, or
  c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region comprising the amino acid sequence of SEQ ID NO: 34, or
  d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region comprising the amino acid sequence of SEQ ID NO: 34.

In an embodiment, said isolated antibody or antibody fragment specific for human C5aR comprises
  a) the VH of SEQ ID NO: 35 and the VL of SEQ ID NO: 36 or
  b) the VH of SEQ ID NO: 42 and the VL of SEQ ID NO: 43 or
  a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises
  a) the HC of SEQ ID NO: 37 and the LC of SEQ ID NO: 38 or
  b) the HC of SEQ ID NO: 44 and the LC of SEQ ID NO: 45 or
  a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Apparent $EC_{50}$ for Full-Length C5aR

In further embodiments, the present disclosure refers to an isolated antibody or antibody fragment specific for human C5aR, wherein said isolated antibody binds to human C5aR with an $EC_{50}$ concentration of 20 nM or less, 15 nM or less, 10 nM or less, 5 nM or less, 4 nM or less, 3 nM or less, 2 nM or less, 1 nM or less, 0.5 nM or less, 0.4 nM or less, 0.3 nM or less, 0.2 nM or less or 0.1 nM or less.

In embodiments, the present disclosure refers to an isolated antibody or antibody fragment specific for human C5aR, wherein said isolated antibody binds to cynomolgus C5aR with an $EC_{50}$ concentration of 20 nM or less, 10 nM or less, 9 nM or less, 8 nM or less, 7 nM or less, 6 nM or less, 5 nM or less, 4 nM or less, 3 nM or less, or 1 nM or less.

In an embodiment, the present disclosure refers to an isolated antibody or antibody fragment specific for human C5aR, wherein said isolated antibody binds to human C5aR and cynomolgus C5aR with an $EC_{50}$ concentration of $K_D$ of 10 nM or less.

In an embodiment, said human C5aR comprises the amino acid sequence of SEQ ID NO: 1. In an embodiment, said human C5aR comprises the amino acid sequence of SEQ ID NO: 2. In an embodiment, said cynomolgus C5aR comprises the amino acid sequence of SEQ ID NO: 3.

In certain embodiments, said $EC_{50}$ concentration is determined in IgG format. In embodiments, said human C5aR or cynomolgus C5aR is expressed on cells. In embodiments, said human C5aR or cynomolgus C5aR is expressed on engineered CHO cells expressing full-length human. In embodiments, said CHO cells are Flp-In™ CHO cells. In certain embodiments, said human C5aR or cynomolgus C5aR is expressed on neutrophils. In embodiments, said human C5aR is expressed on human neutrophils. In embodiments, said cynomolgus C5aR is expressed on cynomolgus neutrophils. In certain embodiments, said neutrophils are derived from whole-blood. In certain embodiments, said EC$_{50}$ concentration is determined as described herein in Example 7.

In further embodiments, said isolated antibody or antibody fragment specific for human C5aR does substantially not bind to a C5aR related antigen selected from the group consisting of human C5L2, human ChemR23, human FPR1 and C3aR. In certain embodiments, said isolated antibody or antibody fragment specific for human C5aR does not substantially bind to a C5aR related antigen selected from the group consisting of human C5L2, human ChemR23, human FPR1 and C3aR at an IgG concentration of 300 nM. In an embodiment, said binding is determined as described in Example 7.

In an embodiment, said isolated antibody or antibody fragment specific for human C5aR, comprises
a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region comprising the amino acid sequence of SEQ ID NO: 34, or
c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region comprising the amino acid sequence of SEQ ID NO: 34, or
d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region comprising the amino acid sequence of SEQ ID NO: 34.

In an embodiment, said isolated antibody or antibody fragment specific for human C5aR comprises
a) the VH of SEQ ID NO: 35 and the VL of SEQ ID NO: 36 or
b) the VH of SEQ ID NO: 42 and the VL of SEQ ID NO: 43 or
a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises
a) the HC of SEQ ID NO: 37 and the LC of SEQ ID NO: 38 or
b) the HC of SEQ ID NO: 44 and the LC of SEQ ID NO: 45 or
a HC and a LC that has at least at least 80%, at least 85%, at least 90% or at least 95% identity to the VH of SEQ ID NO: 37 or 44 and to the VL of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

In an embodiment, the present disclosure refers to an isolated antibody or antibody fragment specific for human C5aR, wherein said antibody or antibody fragment binds to human C5aR comprising SEQ ID NO: 1 and/or SEQ ID NO: 2 with an EC$_{50}$ concentration of 5 nM or less, such as 4 nM or less, 3 nM or less, 2 nM or less, 1 nM or less or 0.5 nM or less.

In certain embodiments, said human C5aR is presented on virus-like-particles. In certain embodiments, said human C5aR is expressed as a fusion protein. In certain embodiments, said human C5aR is fused to a GAG protein. In embodiments, said fusion protein comprises an amino acid sequence disclosed in Table 8. In certain embodiments, said binding is determined by ELISA as described in Example 8.

In an embodiment, said isolated antibody or antibody fragment specific for human C5aR, comprises
a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR
a) the VH of SEQ ID NO: 35 and the VL of SEQ ID NO: 36 or
b) the VH of SEQ ID NO: 42 and the VL of SEQ ID NO: 43 or
a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR
a) the HC of SEQ ID NO: 37 and the LC of SEQ ID NO: 38 or
b) the HC of SEQ ID NO: 44 and the LC of SEQ ID NO: 45 or
a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Functionality—C5A-Induced Activation of C5aR

In general, the isolated antibody or antibody fragment specific for human C5aR according to the present disclosure can be used to prevent or to inhibit the interaction between human C5aR and human C5a, thereby preventing, inhibiting, neutralizing or reducing the signaling pathways that are mediated by C5aR and/or modulating the biological pathways and mechanisms in which C5aR is involved.

In an embodiment, the present disclosure pertains to an isolated antibody or antibody fragment specific for human C5aR, wherein said isolated antibody or antibody fragment specifically interferes with C5aR-mediated signal transduction.

In a further embodiment of the present disclosure, the isolated antibody or antibody fragment specific for human C5aR specifically interferes with the interaction of C5a with C5aR expressed on cells. In yet a further embodiment, said isolated antibody or antibody fragment is capable of specifically interfering with C5a induced signal transduction mediated by C5aR.

Methods for assaying for functional activity of a C5aR specific antibody may utilize binding assays, such as the enzyme-linked immunosorbent assay (ELISA), radioimmunoassay (RIA), fluorescence activated cell sorting (FACS) and other methods that are well known in the art (see Hampton, R. et al. (1990; Serological Methods a Laboratory Manual, APS Press, St Paul, MN) and Maddox, D. E. et al. (1983; J. Exp. Med. 158:1211-1216)). Alternatively, assays may test the ability of the isolated antibody or antibody fragment of the present disclosure in eliciting a biological response as a result of binding to C5aR, either in vivo or in vitro. Such assays are described in the Examples disclosed herein. Other suitable assays will be known to those of skill in the art.

In certain embodiments, the isolated antibody or antibody fragment of the present disclosure antagonizes human C5aR activity. In an embodiment, the isolated antibody or antibody fragment neutralizes human C5aR activity. In an embodiment, the isolated antibody or antibody fragment of the present disclosure inhibits human C5aR activity. In an embodiment, the isolated antibody or antibody fragment of the present disclosure inhibits human C5aR signaling. In an embodiment, said human C5aR activity or human C5aR signaling is induced by C5a. In an embodiment, said human C5aR activity or human C5aR signaling is induced by the interaction of human C5a with human C5aR. In an embodiment, said C5aR activity or C5aR signaling is induced by the binding of human C5a to human C5aR. In an embodiment, said C5aR is expressed on cells. In an embodiment, said human C5aR activity or human C5aR signaling is inhibited in vitro and/or ex vivo and/or in vivo.

C5A-Induced β-Arrestin Recruitment

The ability of the isolated antibody or antibody fragment specific for human C5aR according to the present disclosure to inhibit C5a induced C5aR activation was tested in a β-arrestin recruitment assay as described in Example 14 and revealed that both antibodies are even more potent antagonists of C5aR activity when compared to the prior art antibody RefMAB #1, in particular at high pathophysiological C5a concentrations.

Accordingly, in an embodiment of the present disclosure, the isolated antibody or antibody fragment specific for human C5aR inhibits the ability of C5a to induce C5aR activity. In an embodiment, said C5a induced C5aR activity is determined in a β-arrestin recruitment assay as described in Example 14. In an embodiment, said C5a induced C5aR activity is determined in vitro.

In one such embodiment, the present disclosure provides an isolated antibody or antibody fragment specific for human C5aR, wherein said isolated antibody or antibody fragment inhibits the ability of human C5a to induce human C5aR-mediated β-arrestin recruitment. In an embodiment, said isolated antibody or antibody fragment inhibits human C5a induced β-arrestin recruitment. In an embodiment, said isolated antibody or antibody fragment inhibits human C5aR mediated β-arrestin recruitment.

In a further embodiment of the present disclosure, the isolated antibody or antibody fragment specific for human C5aR inhibits human C5a induced human C5aR interaction with β-arrestin. In one such embodiment, said human C5a induced human C5aR interaction with β-arrestin and/or that human C5a induced beta-arrestin recruitment is measured using beta-galactosidase enzyme fragment complementation. In an embodiment, said human C5a induced human C5aR interaction with β-arrestin and/or that human C5a induced β-arrestin recruitment is determined as described in Example 14. In one such embodiment, said human C5a induced human C5aR interaction with β-arrestin and/or that human C5a induced β-arrestin recruitment is tested at an IgG concentration of 50 nM.

The ability of an isolated antibody or antibody fragment according to the present disclosure to inhibit human C5a induced human C5aR activity, such as to inhibit human C5a induced human C5aR interaction with β-arrestin and/or human C5a induced human C5aR mediated b-b-recruitment can be determined by generating dose-response curves for increasing concentrations of human C5a and a fixed concentration of IgG and by calculating respective EC50 concentrations.

In an embodiment, the present disclosure provides an isolated antibody or antibody fragment specific for human C5aR, wherein said isolated antibody or antibody fragment increases the $EC_{50}$ concentration determined for human C5a in a β-arrestin recruitment assay by at least 5-fold or more, such as at least 6-fold, at least 7-fold, at least 8-fold, at least 9-fold, at least 10-fold, at least 11-fold, at least 12-fold or at least 13-fold at an IgG concentration of 50 nM when compared to the $EC_{50}$ concentration determined in the absence of said isolated antibody or antibody fragment.

In an embodiment, the present disclosure provides an isolated antibody or antibody fragment specific for human C5aR, wherein said isolated antibody or antibody fragment increases the $EC_{50}$ concentration determined for human C5a in a β-arrestin recruitment assay at an IgG concentration of 50 nM of about 5-fold, of about 6-fold, of about 7-fold, of about 8-fold, of about 9-fold, of about 10-fold, of about 11-fold, of about 12-fold or of about 13-fold when compared to the $EC_{50}$ concentration determined in the absence of said isolated antibody or antibody fragment.

In an embodiment, the present disclosure provides an antibody or antibody fragment specific for human C5aR, wherein said human C5a needs to be present in an at least 5-fold or higher, such as at least 6-fold or higher, at least 7-fold or higher, at least 8-fold or higher, at least 9-fold or higher, at least 10-fold or higher, at least 11-fold or higher, at least 12-fold or higher, or at least 13-fold or higher concentration in order to induce the same human C5aR activity in a β-arrestin recruitment assay at an IgG concentration of 50 nM when compared to the concentration of human C5a in the absence of said antibody or antibody fragment.

In an embodiment, said β-arrestin recruitment assay is performed as described in Example 14. In an embodiment, said β-arrestin recruitment assay is performed in vitro.

Alternatively, the ability of the isolated antibody or antibody fragment specific for C5aR according to the present disclosure to inhibit C5a induced C5aR mediated β-arrestin recruitment can be determined by calculating the % inhibition for different human C5a concentrations.

In one such embodiment, the isolated antibody or antibody fragment specific for C5aR according to the present disclosure inhibits human C5a induced human C5aR mediated β-arrestin recruitment by at least 50%, by at least 55%, by at least 60%, by at least 70%, by at least 80% or by at least 90% at an IgG concentration of 50 nM and in the presence of 1.2 nM or 11 nM human C5a compared to the level of human C5a induced human C5aR mediated β-arrestin recruitment in the presence of 1.2 nM or 11 nM human C5a and absence of said antibody or antibody fragment.

In one such embodiment, the isolated antibody or antibody fragments specific for C5aR according to the present disclosure inhibits human C5a induced human C5aR mediated beta-arrestin recruitment by at least 25%, such as by at least 30%, by at least 35%, by at least 40%, by at least 45% or by at least 50% at an IgG concentration of 50 nM and in the presence of 1.2 nM or 11 nM human C5a compared to the level of human C5a induced human C5aR mediated β-arrestin recruitment in the presence of 100 nM human C5a and absence of said antibody or antibody fragment.

In an embodiment, said β-arrestin recruitment assay is performed as described in Example 14. In an embodiment, said β-arrestin recruitment assay is performed in vitro.

In an embodiment, said isolated antibody or antibody fragment specific for human C5aR comprises
 a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
 b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
 c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
 d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region comprising the amino acid sequence of SEQ ID NO: 34.

In an embodiment, said isolated antibody or antibody fragment specific for human C5aR for comprises
 a) the VH of SEQ ID NO: 35 and the VL of SEQ ID NO: 36 or
 b) the VH of SEQ ID NO: 42 and the VL of SEQ ID NO: 43 or
  a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR for comprises
 a) the HC of SEQ ID NO: 37 and the LC of SEQ ID NO: 38 or
 b) the HC of SEQ ID NO: 44 and the LC of SEQ ID NO: 45 or
  a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

C5A-Induced Upregulation of CD11b Expression

C5a, as a potent activator of human neutrophils and monocytes, induces up-regulation of the cell surface antigen CD11b in such cells. Thus, the ability of an isolated antibody or antibody fragment specific for human C5aR according to the present disclosure to inhibit C5a induced activation of granulocytes and/or monocytes can be assessed by determine CD11b expression levels in such cells.

The ability of the isolated antibody or antibody fragments according to the present disclosure to inhibit CD11b expression in granulocytes and/or monocytes can be determined by generating dose-response curves for increasing concentrations of IgG and fixed concentration of human C5a and calculating the respective $IC_{50}$ concentrations. Alternatively, the ability of an isolated antibody or antibody fragments according to the present disclosure to inhibit CD11b expression in granulocytes and/or monocytes C5a can be determined by calculating the % inhibition of CD11b expression for different IgG concentrations.

In one such embodiment, the isolated antibody or antibody fragment specific for human C5aR according to the present disclosure inhibits human C5a induced CD11b expression in human granulocytes and/or human monocytes with an $IC_{50}$ concentration of 30 nM or less, 25 nM or less, 20 nM or less, 15 nM or less, 10 nM or less or 5 nM or less, in the presence of 15 nM human C5a.

In another embodiment, the isolated antibody or antibody fragment specific for human C5aR according to the present disclosure inhibits human C5a induced CD11b expression in human granulocytes and/or human monocytes by at least 70%, by at least 75%, by at 80%, by at least 85% or by at least 90% in the presence of 15 nM human C5a and an IgG concentration of 600 nM compared to the level of CD11b expression in the presence of 15 nM human C5a and absence of said antibody or antibody fragment.

In a further embodiment, the isolated antibody or antibody fragment specific for human C5aR according to the present disclosure inhibits human C5a induced CD11b expression in human granulocytes with an $IC_{50}$ concentration of 150 nM or less, 125 nM or less, 100 nM or less, 90 nM or less, 80 nM or less, 70 nM or less, 60 nM or less, 50 nM or less, or 40 nM or less in the presence of 150 nM human C5a.

In an embodiment, the isolated antibody or antibody fragment specific for human C5aR according to the present disclosure inhibits human C5a induced CD11b expression in human granulocytes with an $IC_{50}$ concentration of 42 nM in the presence of 150 nM human C5a.

In a further embodiment, the isolated antibody or antibody fragment specific for human C5aR according to the present disclosure inhibits human C5a induced CD11b expression in human granulocytes by at least by at least 65%, at least 70%, at least 75%, at least 80% or at least 90% in the presence of 150 nM human C5a and an IgG concentration of 600 nM compared to the level of CD11b expression in the presence of 150 nM human C5a and absence of said antibody or antibody fragment.

In an embodiment, the isolated antibody or antibody fragments specific for human C5aR according to the present disclosure inhibits C5a induced CD11b expression in human granulocytes by at least 45%, at least 50%, at least 55%, at least 60% or at least 65% in the presence of 150 nM human C5a and an IgG concentration of 100 nM compared to the level of CD11b expression in the presence of 150 nM human C5a and absence of said antibody or antibody fragment.

In an embodiment, said determination of CD11b expression is performed as described in Example 15. In an embodiment, said determination of CD11b expression in performed in vitro and/or ex vivo.

In an embodiment, said isolated antibody or antibody fragment specific for human C5aR comprises
- a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
- b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
- c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
- d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR for comprises
- a) the VH of SEQ ID NO: 35 and the VL of SEQ ID NO: 36 or
- b) the VH of SEQ ID NO: 42 and the VL of SEQ ID NO: 43 or
- a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR for comprises
- a) the HC of SEQ ID NO: 37 and the LC of SEQ ID NO: 38 or
- b) the HC of SEQ ID NO: 44 and the LC of SEQ ID NO: 45 or
- a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Furthermore, the inhibitory activity of the isolated antibody or antibody fragment according to the present disclosure on human C5a induced CD11b expression was further analyzed over a prolonged period of time meaning that the antibodies were pre-incubated with granulocytes and/or monocytes present in whole-blood over time of varying length (e.g. 300 minutes vs. 20 minutes) before human C5a was added. Surprisingly, the experiment revealed that the isolated antibodies according to the present disclosure are even more potent antagonists of C5aR activity over a longer period of time, e.g. a prolonged period of incubation time, in particular when compared to the prior art antibody RefMAB #1.

Accordingly, the ability of the isolated antibody or antibody fragment according to the present disclosure to inhibit human C5a induced CD11b expression in granulocytes and/or monocytes over a prolonged period of time can be determined by generating dose-response curves for increasing concentrations of IgG and a fixed concentration of human C5a and by calculating respective $EC_{50}$ values after incubating said isolated antibodies with said granulocytes and/or monocytes for different incubation times.

Figure 6:
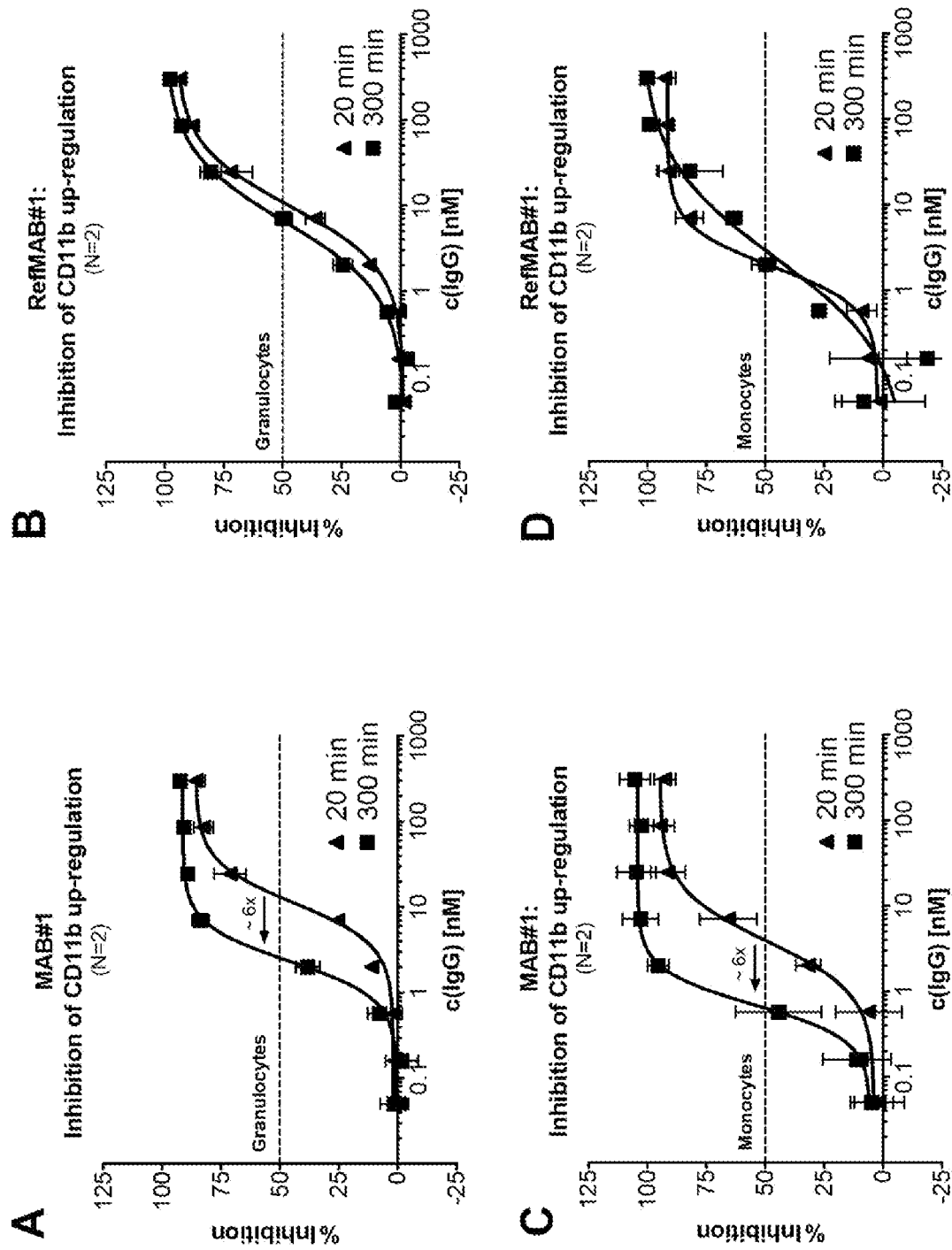
FIG. 6: Inhibition of human C5a induced CD11b upregulation in human granulocytes and monocytes determined over a prolonged period of time of incubation. Comparison of MAB #1and RefMAB #1 in a CD11b whole blood assay after incubation of IgGs with target cells for either 20 minutes or 300 minutes. IgGs were added in serial dilutions and incubated for either 20 minutes or 300 minutes with subsequent stimulation with 15 nM human C5a. Either granulocytes (FIGS. 6A and B) or monocytes (FIGS. 6C and D) were gated as target cells. CD11b levels were determined. Log dose-inhibition curves are shown. Data are expressed as % inhibition of CD11b upregulation at 15 nM human C5a. Results for MAB #1 are shown in FIGS. 6A and C and results for RefMAB #1 are provided in FIGS. 6B and D.

As shown in FIGS. 6A and C, the isolated antibodies or antibody fragments of the present disclosure exhibited a clear shift of the determined dose-response curve to lower IgG concentrations determined after 300 minutes of incubation when compared to the dose-response curve determined after 20 minutes of incubation. Interestingly, RefMAB #1 revealed no increased potency over time (see FIGS. 6B and D).

Thus, in an embodiment, the isolated antibody or antibody fragment according to the present disclosure is more potent in inhibiting C5a induced CD11b expression in human granulocytes and/or human monocytes after a prolonged period of incubation time with said cells.

In one such embodiment, the isolated antibody or antibody fragment according to the present disclosure inhibits human C5a induced CD11b expression in human granulocytes and/or human monocytes with an at least 2-fold, at least 4-fold, at least 5-fold or at least 6-fold lower $IC_{50}$ concentration determined after a prolonged period of incubation time of 50 minutes, of 100 minutes, of 150 minutes, of 200 minutes, of 250 minutes, or of 300 minutes when compared to the $IC_{50}$ concentration determined after a period of incubation time of 20 minutes.

In an embodiment, the isolated antibody or antibody fragment according to the present disclosure inhibits human C5a induced CD11b expression in human granulocytes and/or human monocytes with an about 5-fold lower $IC_{50}$ concentration determined after a prolonged period of incubation time of 300 minutes when compared to the $IC_{50}$ concentration determined after a period of incubation time of 20 minutes.

In an embodiment, the isolated antibody or antibody fragment according to the present disclosure inhibits human C5a induced CD11b expression in human granulocytes and/or human monocytes with an at least 3-fold, at least 4-fold, at least 5-fold, at least 10-fold, at least 15-fold or at least 19-fold lower $IC_{50}$ concentration determined after a prolonged period of incubation time of 300 minutes when compared to the corresponding $IC_{50}$ concentration of RefMAB #1.

In an embodiment, the isolated antibody or antibody fragment according to the present disclosure inhibits human C5a induced CD11b expression in human granulocytes and/or human monocytes with an $IC_{50}$ concentration of 3 nM or less, 2.5 nM or less, 2 nM or less, 1.5 nM or less or 1 nM or less, after a prolonged period of incubation time of 300 minutes with said cells.

In an embodiment, said isolated antibody or antibody fragment specific for human C5aR comprises a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR comprises a) the VH of SEQ ID NO: 35 and the VL of SEQ ID NO: 36 or b) the VH of SEQ ID NO: 42 and the VL of SEQ ID NO: 43 or a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises a) the HC of SEQ ID NO: 37 and the LC of SEQ ID NO: 38 or b) the HC of SEQ ID NO: 44 and the LC of SEQ ID NO: 45 or a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

C5A-Induced Migration of Neutrophils

In further assays, the ability of the isolated antibody or antibody fragment specific for human C5aR according to the present disclosure to inhibit human C5a induced migration of human neutrophils was evaluated and revealed that MAB #1 efficiently inhibited C5 induced neutrophil migration in vitro.

Thus, in an embodiment of the present disclosure, said isolated antibody or antibody fragment specific for human C5aR of the present disclosure inhibits human C5a induced migration of human neutrophils in vitro.

In a further embodiment, said isolated antibody or antibody fragment inhibits human C5a induced migration of human neutrophils by at least 25%, at least 30%, at least 40%, at least 50%, at least 60%, at least 70%, at least 75 or at least 80% compared to the level of migration in the presence of 10 nM human C5a and absence of said isolated antibody or antibody fragment in vitro.

In an embodiment, said migration of human neutrophils is determined after 15 minutes, after 25 minutes and/or after 35 minutes. In certain embodiments, said isolated antibody or antibody fragment according to the present disclosure is tested at an IgG concentration of 100 nM and/or 600 nM.

In an embodiment, said isolated antibody or antibody fragment of the present disclosure inhibits human C5a induced migration of human neutrophils by at least 25% after 35 minutes and at an IgG concentration of 100 nM compared to the level of migration after 35 minutes in the presence of 10 nM human C5a and absence of said antibody or antibody fragment.

In an embodiment, said isolated antibody or antibody fragment of the present disclosure inhibits human C5a induced migration of human neutrophils by at least 60% after 25 minutes and at an IgG concentration of 100 nM and/or 600 nM compared to the level of migration after 25 minutes in the presence of 10 nM human C5a and absence of said antibody or antibody fragment.

In an embodiment, said isolated antibody or antibody fragment of the present disclosure inhibits human C5a induced migration of human neutrophils by at least 40% after 35 minutes at an IgG concentration of 600 nM compared to the level of migration after 35 minutes in the presence of 10 nM human C5a and absence of said antibody.

In an embodiment, said isolated antibody or antibody fragment specific for human C5aR comprises a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR comprises a) the VH of SEQ ID NO: 35 and the VL of SEQ ID NO: 36 or b) the VH of SEQ ID NO: 42 and the VL of SEQ ID NO: 43 or a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises a) the HC of SEQ ID NO: 37 and the LC of SEQ ID NO: 38 or b) the HC of SEQ ID NO: 44 and the LC of SEQ ID NO: 45 or a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Effector Function

The Fc region of an immunoglobulin generally confers to the favorable pharmacokinetic properties of antibodies, such as prolonged half-life in serum and to the ability to induce effector function via binding to Fc receptors expressed on cells. On the other hand, binding to Fc receptors might also results in an undesirable activation of certain cell surface receptors leading to unwanted cytokine release and severe side effects upon systemic administration.

Accordingly, for certain therapeutic situations, it is desirable to reduce or abolish the normal binding of the wild-type Fc region of an antibody, such as of an wild-type IgG Fc region to one or more or all of Fc receptors and/or binding to a complement component, such as C1q in order to reduce or abolish the ability of the antibody to induce effector function. For instance, it may be desirable to reduce or abolish the binding of the Fc region of an antibody to one or more or all of the Fcγ receptors, such as: FcγRI, FcγRIIa, FcγRIIb, FcγRIIIa.

Effector function can include, but is not limited to, one or more of the following: complement dependent cytotoxicity (CDC), antibody-dependent cell-mediated cytotoxicity (ADCC), antibody-dependent cellular phagocytosis (ADCP), cytokine secretion, immune complex-mediated antigen uptake by antigen-presenting cells, binding to NK cells, binding to macrophages, binding to monocytes, binding to polymorphonuclear cells, direct signaling inducing apoptosis, crosslinking of target-bound antibodies, dendritic cell maturation, or T cell priming.

A reduced or abolished binding of an Fc region to an Fc receptor and/or to C1q is typically achieved by mutating a wild-type Fc region, such as of an IgG1 Fc region, more particular a human IgG1 Fc region, resulting in a variant or engineered Fc region of said wild-type Fc region, e.g. a variant human IgG1 Fc region. Substitutions that result in reduced binding can be useful. For reducing or abolishing the binding properties of an Fc region to an Fc receptor, non-conservative amino acid substitutions, i.e. replacing one amino acid with another amino acid having different structural and/or chemical properties, are preferred.

Accordingly, in an embodiment, the isolated antibody or antibody fragment specific for human C5aR according to the present disclosure comprises a variant Fc region having a reduced or abolished binding to an Fc receptor and/or to C1q when compared to the wild-type Fc region. In one such embodiment, the isolated antibody or antibody fragment according to the present disclosure comprises a variant Fc region that reduces or abolishes the ability of the antibody to induce effector function. In a further embodiment, the isolated antibody or antibody fragment according to the present disclosure does not substantially induce effector function.

In certain embodiments, the effector function is one or more selected from the group consisting of CDC, ADCC and ADCP. In an embodiment, the effector function is ADCC. In an embodiment, the effector function is CDC. In an embodiment, the effector function is ADCP. In an embodiment, the isolated antibody or antibody fragment according to the present disclosure does not substantially induce ADCC and/or CDC and/or ADCP. In an embodiment, the isolated antibody or antibody fragment according to the present disclosure does not induce ADCC or ADCP in vitro.

In an embodiment, the variant Fc region of the isolated antibody or antibody fragment according to the present disclosure comprises one or more amino acid substitutions that reduce or abolish the binding of the variant Fc region to one or more Fc receptors and/or to C1q when compared to the wild-type Fc region. In an embodiment, the variant Fc region of the isolated antibody or antibody fragment according to the present disclosure comprises one or more amino acid substitutions that reduce or abolish the ability of the antibody to induce effector function when compared to the wild-type Fc region.

In a particular embodiment, the one or more amino acid substitutions may reduce the binding affinity of the variant Fc region for one or more Fc receptors and/or to C1q by at least 2-fold, at least 5-fold, at least 10-fold, at least 20-fold or even at least 50-fold when compared to the wild-type Fc region. In alternative embodiments, the one or more amino acid substitutions may reduce the ability of the isolated antibody or antibody fragment according to the present disclosure to induce effector function by at least 2-fold, at least 5-fold, at least 10-fold, at least 20-fold or even at least 50-fold when compared to the wild-type Fc region.

In an embodiment, the variant Fc region of the isolated antibody or antibody fragment according to the present disclosure does not substantially bind to one or more Fc receptors and/or C1q. In an embodiment, the variant Fc region of the antibody according to the present disclosure does substantially abolish the ability of said antibody to induce effector function. In an embodiment, the antibody or antibody fragment according to the present disclosure does not substantially induce effector function. In an embodiment, said effect function is ADCC and/or ADCP and/or CDC. In an embodiment, the antibody or antibody fragment according to the present disclosure does not substantially induce effector function meaning that the level of induced effector function is not significantly above the background as measured in the absence of said antibody.

In an embodiment, the Fc receptor is a human Fc receptor. In an embodiment, the Fc receptor is an Fcγ receptor. In an embodiment, the Fc receptor is a human FcγRIIIa, FcγRI, FcγRIIa and/or FcγRIIb.

In an embodiment, the effector function is one or more selected from the group of CDC, ADCC and ADCP. In a particular embodiment, the effector function is ADCC, CDC and ADCP. In a more particular embodiment, the effector function is ADCC and ADCP.

In an embodiment, the wild-type Fc region is an IgG1 Fc region. In an embodiment, the wild-type Fc region is a human IgG1 Fc region. In an embodiment, the wild-type Fc region is a human IgG1 Fc region. In an embodiment, the wild-type Fc region is a human IgG1 Fc region comprising the amino acid sequence of:

(SEQ ID NO: 11)
PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK.

In an embodiment, the isolated antibody or antibody fragment according to the present disclosure comprises a variant human IgG1 Fc region, which comprises one or more amino acid substitutions compared to the wild-type human IgG1 Fc region. In an embodiment, that one or more amino acid substitutions reduce or abolish the binding of the variant Fc region to an Fc receptor and/or to C1q and/or reduces the ability of said antibody to induce effector function when compared to the wild-type Fc region.

In an embodiment, the variant human IgG1 Fc region of the antibody or antibody fragment according to the present disclosure comprises an amino acid substitution at one or more positions selected from the group of 234, 235, 237, 330 and 331 with numbering according EU index compared to the wild type IgG1 Fc region comprising the amino acid sequence of SEQ ID NO: 11.

In an embodiment, said variant human IgG1 Fc region comprises an amino acid substitution at one or more positions selected from the group of L234, L235 and G237 with numbering according EU index compared to the wild-type IgG1 Fc region comprising the amino acid sequence of SEQ ID NO: 11.

In an embodiment, the variant human IgG1 Fc region comprises the amino acid substitutions at one or more positions selected from the group of L234A, L235E G237A with numbering according EU index compared to the wild-type IgG1 Fc region comprising the amino acid sequence of SEQ ID NO: 11.

In an embodiment, the variant human IgG1 Fc region comprises the amino acid substitutions L234A and L235E with numbering according EU index compared to the wild-type IgG1 Fc region comprising the amino acid sequence of SEQ ID NO: 11.

In an embodiment, the variant human IgG1 Fc region comprises the amino acid substitutions L234A, L235E and G237A with numbering according EU index compared to the wild-type IgG1 Fc region comprising the amino acid sequence of SEQ ID NO: 11.

In an embodiment, the variant human IgG1 Fc region comprises an amino acid substitution at one or more position selected from the group of A330 and P331 with numbering according EU index compared to the wild-type IgG1 Fc region comprising the amino acid sequence of SEQ ID NO: 11.

In an embodiment, the variant human IgG1 Fc region comprises the amino acid substitutions at one or more positions selected from the group of A330S and P331S with numbering according EU index compared to the wild-type IgG1 Fc region comprising the amino acid sequence of SEQ ID NO: 11.

In an embodiment, the variant human IgG1 Fc region comprises the amino acid substitutions A330S and P331S with numbering according EU index compared to the wild-type IgG1 Fc region comprising the amino acid sequence of SEQ ID NO: 11.

In an embodiment, the variant human IgG1 Fc region comprises the amino acid substitutions L234A, L235E, G237A, A330S and P331S with numbering according EU index compared to the wild type IgG1 Fc region comprising the amino acid sequence of SEQ ID NO: 11.

In an embodiment, the antibody or antibody fragment according to the present disclosure comprises a variant human IgG1 Fc region, which comprises one or more amino acid substitutions compared to the wild-type human IgG1 Fc region comprising the sequence of SEQ ID NO: 11, that reduce or abolish the binding affinity of the variant Fc region to one or more Fc receptors and/or to C1q and/or reduces the ability of said antibody to induce effector function, wherein the one or more amino acid substitutions are L234A, L235E, G237A, A330S and P331S with numbering according EU index.

In an embodiment, the isolated antibody or antibody fragment according to the present disclosure is of the human IgG1 class. In an embodiment, the isolated antibody or antibody fragment according to the present disclosure is of a variant human IgG1 class. In an embodiment, the isolated antibody or antibody fragment according to the present disclosure does not substantially induce effector function in vitro. In an embodiment, the variant human IgG1 Fc region does not substantially bind to one or more Fc receptors and/or C1q. In one such embodiment, the isolated antibody or antibody fragment according to the present disclosure comprises the amino acid substitution selected from the group of: L234A, L235E, G237A, A330S and P331S, with numbering according to EU index compared to the wild type IgG1 Fc region comprising the amino acid sequence of SEQ ID NO: 11.

In an embodiment, the isolated antibody or antibody fragment according to the present disclosure is of the human IgG1 class comprising the amino acid substitution L234A, L235E, G237A, A330S and P331S, with numbering according to EU index.

In an embodiment, the isolated antibody or antibody fragment according to the present disclosure comprises the amino acid substitution L234A, L235E, G237A, A330S and P331S, with numbering according to EU index.

In an embodiment, the isolated antibody or antibody fragment according to the present disclosure comprises the amino acid substitution L234A, L235E, G237A, A330S and P331S, with numbering according to EU index compared to the wild type IgG1 Fc region comprising the amino acid sequence of SEQ ID NO: 11.

In one such embodiment, the isolated antibody or antibody fragment according to the present disclosure comprises the amino acid substitution L234A, L235E, G237A, A330S and P331S, with numbering according to EU index and does not substantially induce effector function in vitro. In an embodiment, the effector function is one or more selected from the group of CDC, ADCC and ADCP.

In one such embodiment, the isolated antibody or antibody fragment according to the present disclosure comprises the amino acid substitution L234A, L235E, G237A, A330S and P331S, with numbering according to EU index compared to the wild-type human IgG1 Fc region comprising the amino acid sequence of SEQ ID NO: 11 and does not substantially bind to one or more Fc receptors and/or C1q in vitro.

In an embodiment, the isolated antibody or antibody fragment according to the preset disclosure is of the human IgG1 class. In an embodiment, the isolated antibody or antibody fragment to the preset disclosure does not substantially induce effector function in vitro. In an embodiment, the isolated antibody or antibody fragment according to the present disclosure comprises one or more amino acid substitution selected from the group of: L234A, L235E, G237A, A330S and P331S, with numbering according to EU index.

In an embodiment, said isolated antibody or antibody fragment specific for human C5aR comprises
  a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
  b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR for comprises a) the VH of SEQ ID NO: 35 and the VL of SEQ ID NO: 36 or b) the VH of SEQ ID NO: 42 and the VL of SEQ ID NO: 43 or a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR for comprises a) the HC of SEQ ID NO: 37 and the LC of SEQ ID NO: 38 or b) the HC of SEQ ID NO: 44 and the LC of SEQ ID NO: 45 or a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Binding of an antibody to Fc receptors via its Fc region can be easily determined e.g. by ELISA, or by Surface Plasmon Resonance (SPR) using standard instrumentation such as a Biacore® instrument (GE Healthcare), and Fc receptors may be obtained by recombinant expression. Alternatively, the binding affinity of Fc regions may be evaluated using cell lines known to express particular Fc receptors, such as NK cells expressing FcγIIIa receptor. Effector function of an antibody can be measured by methods known in the art. Suitable in vitro assays to assess ADCC activity of a molecule of interest are for instance described in WO2012130831. Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998). To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)). C1q binding assays (such as ELISA) may be carried out to determine whether an antibody is able to bind C1q and hence has CDC activity (see, for example WO 2006/029879). In vitro methods to asses binding to Fc receptors or to asses immune effector function are described herein in Examples 10-13.

Fusion Proteins

The isolated antibody or antibody fragment according to the present disclosure may or may not be fused to one or more other amino acid residues, polypeptides or moieties. Such a fusion protein may be prepared in any suitable manner, including genetically or chemically approaches. Said linked moieties may contain secretory or leader sequences, sequences that aid detection, expression, separation or purification, or sequences that confer to increased protein stability, for example, during recombinant production. Non-limiting examples of potential moieties include beta-galactosidase, glutathione-S-transferase, luciferase, a T7 polymerase fragment, a secretion signal peptide, an antibody or antibody fragment, a toxin, a reporter enzyme, a moiety being capable of binding a metal ion like a poly-histidine tag, a tag suitable for detection and/or purification, a homo- or hetero-association domain, a moiety which increases solubility of a protein, or a moiety which comprises an enzymatic cleavage site.

Accordingly, the isolated antibody or antibody fragment according to the present disclosure may optionally contain one or more moieties for binding to other targets or target proteins of interest. It should be clear that such further moieties may or may not provide further functionality to the antibody and may or may not modify the properties of the isolated antibody or antibody fragment according to the present disclosure.

Diagnostic Use

In an embodiment, the present disclosure provides the use of an isolated antibody or antibody fragment specific for human C5aR according to the present disclosure for the diagnosis of a disease. In an embodiment, the present disclosure provides the use of an antibody or antibody fragment according to the present disclosure for the detection of C5aR, in particular human C5aR and/or cynomolgus C5aR. In an embodiment, the present disclosure provides a method for detecting C5aR in a subject or a sample, comprising the step of contacting said subject or sample with an isolated antibody or antibody fragment specific for human C5aR of the present disclosure. In an embodiment, the present disclosure provides a method for diagnosing a disease in a subject, comprising the step of contacting said subject or sample with an isolated antibody or antibody fragment according to the present disclosure.

In an embodiment, said isolated antibody or antibody fragment specific for human C5aR comprises a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR for comprises a) the VH of SEQ ID NO: 35 and the VL of SEQ ID NO: 36 or b) the VH of SEQ ID NO: 42 and the VL of SEQ ID NO: 43 or
   a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR for comprises
a) the HC of SEQ ID NO: 37 and the LC of SEQ ID NO: 38 or
b) the HC of SEQ ID NO: 44 and the LC of SEQ ID NO: 45 or
   a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Therapeutic Methods

The isolated antibody or antibody fragment according to the present disclosure may be used in therapeutic methods. The antibody or antibody fragment according to the present disclosure may be used for the treatment of a disease, such as cancer, an autoimmune disease or inflammatory disease.

In an embodiment, the present disclosure provides a method for the treatment of a disease.

In an embodiment, the present disclosure provides an isolated antibody or antibody fragment according to the present disclosure for the treatment of a disease. In an embodiment, the present disclosure provides an isolated antibody or antibody fragment according to the present disclosure for use in the treatment of a disease. In an embodiment, the present disclosure provides an isolated antibody or antibody fragment according to the present disclosure for use in the treatment of a disease in a subject in need thereof.

In an embodiment, the present disclosure provides the use of an isolated antibody or antibody fragment according to the present disclosure for the manufacture of a medicament. In an embodiment, the present disclosure provides an isolated antibody or antibody fragment according to the present disclosure for use as a medicament. In an embodiment, the present disclosure provides an isolated antibody or antibody fragment according to the present disclosure for use in medicine. In an embodiment, the present disclosure provides an isolated antibody or antibody fragment according to the present disclosure for use as a medicament for the treatment of a subject in need thereof.

In an embodiment, the disease is associated with the undesired presence of C5aR, in particular human C5aR. In an embodiment, the disease is associated with the undesired presence of C5a, in particular human C5a.

In an embodiment, the disease to be treated is a proliferative disease. In a particular embodiment, the disease is cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, sarcoma, skin cancer, squamous cell carcinoma, bone cancer, melanoma, renal cell carcinoma, and kidney cancer.

In an embodiment, the disease to be treated is an autoimmune or inflammatory disease. Non-limiting examples an autoimmune or inflammatory disease include rheumatoid arthritis (RA), psoriasis, psoriatic arthritis, systemic lupus erythematosus (SLE), lupus nephritis, type I diabetes, Grave's disease, Inflammatory bowel disease (IBD), Crohn's disease (CD), ulcerative colitis (UC), irritable bowel syndrome, multiple sclerosis (MS), autoimmune myocarditis, Kawasaki disease, coronary artery disease, chronic obstructive pulmonary disease (COPD), interstitial lung disease, autoimmune thyroiditis, scleroderma, systemic sclerosis, osteoarthritis, atoptic dermatitis, vitiligo, graft vs. host disease, Sjogren's syndrome, autoimmune nephritis, Goodpasture's syndrome, chronic inflammatory demyelinating polyneuropathy, ANCA-associated vasculitis, uveitis, scleroderma, bullous pemphigoid, Alzheimer's Disease, amyotrophic lateral sclerosis, Huntington's Chorea, cystic fibrosis, gout, age-related macular degeneration, allergy, asthma, antiphospholipid syndrome (APS), atherosclerosis, C3 glomerulopathy and IgA nephropathy, ischemia/reperfusion injury, peritonitis, sepsis and other autoimmune diseases that are a result of either acute or chronic inflammation.

In an embodiment, the present disclosure provides an isolated antibody or antibody fragment specific for human C5aR according to the present disclosure for use in a method of treating a subject having a disease comprising administering to the subject a therapeutically effective amount of an antibody or antibody fragment according to the present disclosure.

In an embodiment, the method further comprises administering to the subject a therapeutically effective amount of at least one additional therapeutic agent. The subject in need of treatment is typically a mammal, more specifically a human. For use in therapeutic methods, an isolated antibody or antibody fragment according to the present disclosure would be formulated, dosed, and administered in a way consistent with good medical practice.

In an embodiment, said isolated antibody or antibody fragment specific for human C5aR comprises
a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 of SEQ ID NO: 34.

In an embodiment, said isolated antibody or antibody fragment specific for human C5aR comprises
a) the VH of SEQ ID NO: 35 and the VL of SEQ ID NO: 36 or
b) the VH of SEQ ID NO: 42 and the VL of SEQ ID NO: 43 or
   a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR comprises
   a) the HC of SEQ ID NO: 37 and the LC of SEQ ID NO: 38 or
   b) the HC of SEQ ID NO: 44 and the LC of SEQ ID NO: 45 or
     a HC and a LC that has at least at least 80%, at least 85%, at least 90% or at least 95% identity to the HC of SEQ ID NO: 37 or 44 and to the LC of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Pharmaceutical Compositions

In an embodiment, the present disclosure provides a pharmaceutical composition comprising an isolated antibody or antibody fragment according to the present disclosure and a pharmaceutically acceptable carrier or excipient.

The pharmaceutical compositions may further comprise at least one other pharmaceutically active compound. The pharmaceutical composition according to the present disclosure can be used in the diagnosis, prevention and/or treatment of diseases associated with the undesired presence of C5aR, in particular human C5aR. In particular, the present disclosure provides a pharmaceutical compositions comprising an antibody or antibody fragment according to the present disclosure that is suitable for prophylactic, therapeutic and/or diagnostic use in a mammal, more particular in a human.

In general, an antibody or antibody fragment according to the present disclosure may be formulated as a pharmaceutical composition comprising at least one antibody or antibody fragment according to the present disclosure and at least one pharmaceutically acceptable carrier or excipient, and optionally one or more further pharmaceutically active compounds. Such a formulation may be suitable for oral, parenteral, topical administration or for administration by inhalation. Accordingly, a pharmaceutical composition comprising at least one antibody or antibody fragment according to the present disclosure may be administered parenterally, such as intravenously, or intramuscularly, or subcutaneously. Alternatively, an antibody of the invention may be administered via a non-parenteral route, such as per-orally or topically. In a preferred embodiment, a pharmaceutical composition comprising an antibody or antibody fragment according to the present disclosure is administered intravenously or subcutaneously.

In particular, an antibody or antibody fragment according to the present disclosure may be used in combination with one or more pharmaceutically active compounds that are or can be used for the prevention and/or treatment of the diseases in which a target antigen of interest is involved, as a result of which a synergistic effect may or may not be obtained. Examples of such compounds, as well as routes, methods and pharmaceutical formulations or compositions for administering them will be clear to the clinician.

In an embodiment, the present disclosure provides a pharmaceutical composition comprising an antibody or antibody fragment according to the present disclosure for use in the prevention and/or treatment of a disease associated with the undesired presence of C5aR. In an embodiment, the present disclosure provides a pharmaceutical composition comprising an antibody or antibody fragment according to the present disclosure for the use as a medicament. In an embodiment, the present disclosure provides a pharmaceutical composition comprising an antibody or antibody fragment according to the present disclosure for use in the prevention and/or treatment of an autoimmune disease and/or or inflammatory disease and/or cancer.

In an embodiment, the present disclosure provides a method for the treatment of an autoimmune disease and/or inflammatory disease and/or cancer in a subject in need thereof using a pharmaceutical composition comprising an antibody or antibody fragment according to the present disclosure.

Further provided is a method of producing an antibody or antibody fragment according to the present disclosure in a form suitable for administration in vivo, the method comprising (a) obtaining an antibody or antibody fragment by a method according to the present disclosure, and (b) formulating said antibody or antibody fragment with at least one pharmaceutically acceptable carrier or excipient, whereby a preparation of antibody or antibody fragment is formulated for administration in vivo. Pharmaceutical compositions according to the present disclosure comprise a therapeutically effective amount of one or more antibodies or antibody fragments according to the present disclosure dissolved in a pharmaceutically acceptable carrier or excipient.

In an embodiment, said isolated antibody or antibody fragment specific for human C5aR according to the present disclosure comprises
   a) the HCDR1 region of SEQ ID NO: 27, the HCDR2 region of SEQ ID NO: 28, the HCDR3 region of SEQ ID NO: 29, the LCDR1 region of SEQ ID NO: 32, the LCDR2 region of SEQ ID NO: 33 and the LCDR3 region of SEQ ID NO: 34, or
   b) the HCDR1 region of SEQ ID NO: 30, the HCDR2 region of SEQ ID NO: 31, the HCDR3 region of SEQ ID NO: 29, the LCDR1 region of SEQ ID NO: 32, the LCDR2 region of SEQ ID NO: 33 and the LCDR3 region of SEQ ID NO: 34, or
   c) the HCDR1 region of SEQ ID NO: 27, the HCDR2 region of SEQ ID NO: 39, the HCDR3 region of SEQ ID NO: 40, the LCDR1 region of SEQ ID NO: 32, the LCDR2 region of SEQ ID NO: 33 and the LCDR3 region of SEQ ID NO: 34, or
   d) the HCDR1 region of SEQ ID NO: 30, the HCDR2 region of SEQ ID NO: 41, the HCDR3 region of SEQ ID NO: 40, the LCDR1 region of SEQ ID NO: 32, the LCDR2 region of SEQ ID NO: 33 and the LCDR3 region of SEQ ID NO: 34.

In an embodiment, said isolated antibody or antibody fragment specific for human C5aR for comprises
   a) the VH of SEQ ID NO: 35 and the VL of SEQ ID NO: 36 or
   b) the VH of SEQ ID NO: 42 and the VL of SEQ ID NO: 43 or
   a VH and a VL that has at least at least 80%, at least 85%, at least 90% or at least 95% identity to the VH of SEQ ID NO: 35 or 42 and to the VL of SEQ ID NO: 36 or 43.

In an embodiment, said isolated antibody or antibody fragment specific for human C5aR for comprises
   a) the HC of SEQ ID NO: 37 and the LC of SEQ ID NO: 38 or
   b) the HC of SEQ ID NO: 44 and the LC of SEQ ID NO: 45 or
   a HC and a LC that has at least at least 80%, at least 85%, at least 90% or at least 95% identity to the VH of SEQ ID NO: 37 or 44 and to the VL of SEQ ID NO: 38 or 45.

In an embodiment, said isolated antibody or antibody fragment specific for human C5aR is a monoclonal antibody or antibody fragment. In an embodiment, said isolated antibody or antibody fragment is a recombinant antibody or antibody fragment. In an embodiment, said isolated antibody or antibody fragment is a human, humanized or chimeric antibody or antibody fragment.

Antibody Sequences

TABLE 1

Antibody sequences of MAB#1

| MAB#1 | SEQ ID NO: | [aa]/DNA |
|---|---|---|
| *MAB#1 Protein* | | |
| HCDR1 (Kabat) | SEQ ID NO: 27 | SYAMH |
| HCDR2 (Kabat) | SEQ ID NO: 28 | RIKSKAQGGTTDYAAHVKG |
| HCDR3 (Kabat) | SEQ ID NO: 29 | VSFSTFDV |
| HCDR1 (Chothia) | SEQ ID NO: 30 | GFTFSSY |
| HCDR2 (Chothia) | SEQ ID NO: 31 | KSKAQGGT |
| HCDR3 (Chothia) | SEQ ID NO: 29 | VSFSTFDV |
| LCDR1 (Kabat) | SEQ ID NO: 32 | SGSSSNIGSYYVS |
| LCDR2 (Kabat) | SEQ ID NO: 33 | RNNQRPS |
| LCDR3 (Kabat) | SEQ ID NO: 34 | DSWDHSSMNV |
| LCDR1 (Chothia) | SEQ ID NO: 32 | SGSSSNIGSYYVS |
| LCDR2 (Chothia) | SEQ ID NO: 33 | RNNQRPS |
| LCDR3 (Chothia) | SEQ ID NO: 34 | DSWDHSSMNV |
| VH | SEQ ID NO: 35 | EVQLVESGGGLVKPGGSLRLSCAASG FTFSSYAMHWVRQAPGKGLEWVGRI KSKAQGGTTDYAAHVKGRFTISRDDS KNTLYLQMNSLKTEDTAVYYCARVS FSTFDVWGQGTLVTVSS |
| VL | SEQ ID NO: 36 | QSVLTQPPSVSGAPGQRVTISCSGSSS NIGSYYVSWYQQLPGTAPKVLIYRNN QRPSGVPDRFSGSKSGTSASLAITGLQ AEDEADYYCDSWDHSSMNVFGGGT KLTVLGQ |
| Heavy chain IgG1_AEASS | SEQ ID NO: 37 | EVQLVESGGGLVKPGGSLRLSCAASG FTFSSYAMHWVRQAPGKGLEWVGRI KSKAQGGTTDYAAHVKGRFTISRDDS KNTLYLQMNSLKTEDTAVYYCARVS FSTFDVWGQGTLVTVSSASTKGPSVF PLAPSSKSTSGGTAALGCLVKDYFPEP VTVSWNSGALTSGVHTFPAVLQSSGL YSLSSVVTVPSSSLGTQTYICNVNHKP SNTKVDKRVEPKSCDKTHTCPPCPAP EAEGAPSVFLFPPKPKDTLMISRTPEV TCVVVDVSHEDPEVKFNWYVDGVEV HNAKTKPREEQYNSTYRVVSVLTVL HQDWLNGKEYKCKVSNKALPSSIEKT ISKAKGQPREPQVYTLPPSREEMTKN QVSLTCLVKGFYPSDIAVEWESNGQP ENNYKTTPPVLDSDGSFFLYSKLTVD KSRWQQGNVFSCSVMHEALHNHYTQ KSLSLSPGK |
| Light chain | SEQ ID NO: 38 | QSVLTQPPSVSGAPGQRVTISCSGSSS NIGSYYVSWYQQLPGTAPKVLIYRNN QRPSGVPDRFSGSKSGTSASLAITGLQ AEDEADYYCDSWDHSSMNVFGGGT KLTVLGQPKAAPSVTLFPPSSEELQAN KATLVCLISDFYPGAVTVAWKADSSP VKAGVETTTPSKQSNNKYAASSYLSL TPEQWKSHRSYSCQVTHEGSTVEKTV APTECS |
| *MAB#1 DNA* | | |
| HCDR1 (Kabat) | SEQ ID NO: 46 | AGCTATGCGATGCAC |
| HCDR2 (Kabat) | SEQ ID NO: 47 | CGTATCAAATCCAAAGCCCAGGGCG GTACGACCGACTACGCGGCGCACGT GAAAGGC |
| HCDR3 (Kabat) | SEQ ID NO: 48 | GTTTCTTTCTCCACTTTCGATGTT |
| HCDR1 (Chothia) | SEQ ID NO: 49 | GGATTTACCTTCAGCAGCTAT |
| HCDR2 (Chothia) | SEQ ID NO: 50 | AAATCCAAAGCCCAGGGCGGTACG |
| HCDR3 (Chothia) | SEQ ID NO: 48 | GTTTCTTTCTCCACTTTCGATGTT |
| LCDR1 (Kabat) | SEQ ID NO: 51 | AGCGGCAGCTCCTCCAATATTGGTA GCTATTACGTGAGC |
| LCDR2 (Kabat) | SEQ ID NO: 52 | CGTAATAATCAACGTCCTAGC |
| LCDR3 (Kabat) | SEQ ID NO: 53 | GACAGCTGGGATCACAGCTCCATGA ATGTT |
| LCDR1 (Chothia) | SEQ ID NO: 51 | AGCGGCAGCTCCTCCAATATTGGTA GCTATTACGTGAGC |
| LCDR2 (Chothia) | SEQ ID NO: 52 | CGTAATAATCAACGTCCTAGC |
| LCDR3 (Chothia) | SEQ ID NO: 53 | GACAGCTGGGATCACAGCTCCATGA ATGTT |
| VH | SEQ ID NO: 54 | GAGGTGCAATTGGTGGAAAGCGGC GGTGGCCTGGTGAAACCAGGCGGC |

TABLE 1-continued

Antibody sequences of MAB#1

| MAB#1 | SEQ ID NO: | [aa]/DNA |
|---|---|---|
| | | AGCCTGCGCCTGAGCTGCGCCGCCT CCGGATTTACCTTCAGCAGCTATGC GATGCACTGGGTGCGCCAGGCCCCG GGCAAAGGTCTCGAATGGGTGGGTC GTATCAAATCCAAAGCCCAGGGCGG TACGACCGACTACGCGGCGCACGTG AAAGGCCGCTTTACCATTAGCCGCG ATGATTCGAAAAACACCCTGTATCT GCAAATGAACAGCCTGAAAACCGA AGATACGGCCGTGTATTATTGCGCG CGTGTTTCTTTCTCCACTTTCGATGT TTGGGGCCAAGGCACCCTGGTGACT GTCTCGAGC |
| VL | SEQ ID NO: 55 | CAGAGCGTGCTGACCCAGCCTCCTA GCGTGAGCGGTGCACCGGGCCAGC GCGTGACCATTAGCTGTAGCGGCAG CTCCTCCAATATTGGTAGCTATTAC GTGAGCTGGTATCAGCAGCTGCCGG GCACGGCGCCGAAAGTTCTGATCTA TCGTAATAATCAACGTCCTAGCGGC GTGCCGGATCGCTTTAGCGGATCCA AAAGCGGCACCAGCGCCAGCCTGG CGATTACCGGCCTGCAAGCAGAAGA TGAAGCGGATTATTACTGCGACAGC TGGGATCACAGCTCCATGAATGTTT TTGGCGGCGGTACCAAGCTGACCGT GCTGGGCCAG |
| Heavy chain (IgG1) IgG1 AEASS | SEQ ID NO: 56 | GAGGTGCAATTGGTGGAAAGCGGC GGTGGCCTGGTGAAACCAGGCGGC AGCCTGCGCCTGAGCTGCGCCGCCT CCGGATTTACCTTCAGCAGCTATGC GATGCACTGGGTGCGCCAGGCCCCG GGCAAAGGTCTCGAATGGGTGGGTC GTATCAAATCCAAAGCCCAGGGCGG TACGACCGACTACGCGGCGCACGTG AAAGGCCGCTTTACCATTAGCCGCG ATGATTCGAAAAACACCCTGTATCT GCAAATGAACAGCCTGAAAACCGA AGATACGGCCGTGTATTATTGCGCG CGTGTTTCTTTCTCCACTTTCGATGT TTGGGGCCAAGGCACCCTGGTGACT GTCTCGAGCGCGTCGACCAAAGGCC CCAGCGTGTTCCCTCTGGCCCCCAG CAGCAAGAGCACCTCTGGCGGAAC AGCCGCCCTGGGCTGCCTGGTCAAG GACTACTTCCCCGAGCCCGTGACCG TGTCCTGGAACTCTGGCGCCCTGAC CAGCGGCGTGCACACCTTTCCAGCC GTGCTCCAGAGCAGCGGCCTGTACA GCCTGAGCAGCGTCGTGACCGTGCC CAGCAGCAGCCTGGGCACCCAGACC CCAGCAACACAAAGGTGGACAAGC TACATCTGCAACGTGAACCACAAGC GGGTGGAACCCAAGAGCTGCGACA AGACCCACACCTGTCCCCCCTGCCC TGCCCCTGAAGCGGAGGGAGCCCCC TCCGTGTTCCTGTTCCCCCCAAAGCC TAAGGACACCCTGATGATCAGCCGG ACCCCCGAAGTGACCTGCGTGGTGG TGGACGTGTCCCACGAGGACCCTGA AGTGAAGTTTAATTGGTACGTGGAC GGCGTGGAAGTGCACAACGCCAAG ACCAAGCCCAGAGAGGAACAGTAC AACAGCACCTACCGGGTGGTGTCCG TGCTGACCGTGCTGCACCAGGACTG GCTGAACGGCAAAGAGTACAAGTG CAAGGTGTCCAACAAGGCCCTGCCT TCCTCCATCGAGAAAACCATCAGCA AGGCCAAAGGCCAGCCCCGCGAGC CCCAGGTGTACACACTGCCCCCTAG CCGGGAAGAGATGACCAAGAACCA GGTGTCCCTGACCTGCCTCGTGAAG GGCTTCTACCCCAGCGACATTGCCG TGGAATGGGAGAGCAACGGCCAGC CCGAGAACAACTACAAGACCACCCC CCCTGTGCTGGACAGCGACGGCTCA |

TABLE 1-continued

Antibody sequences of MAB#1

| MAB#1 | | SEQ ID NO: | [aa]/DNA |
|---|---|---|---|
| Light chain (DNA) | | SEQ ID NO: 57 | TTCTTCCTGTACAGCAAGCTGACCG<br>TGGACAAGAGCCGGTGGCAGCAGG<br>GCAACGTGTTCAGCTGCTCCGTGAT<br>GCACGAGGCCCTGCACAACCACTAC<br>ACCCAGAAGTCCCTGAGCCTGAGCC<br>CCGGCAAG<br>CAGAGCGTGCTGACCCAGCCTCCTA<br>GCGTGAGCGGTGCACCGGGCCAGC<br>GCGTGACCATTAGCTGTAGCGGCAG<br>CTCCTCCAATATTGGTAGCTATTAC<br>GTGAGCTGGTATCAGCAGCTGCCGG<br>GCACGGCGCCGAAAGTTCTGATCTA<br>TCGTAATAATCAACGTCCTAGCGGC<br>GTGCCGGATCGCTTTAGCGGATCCA<br>AAAGCGGCACCAGCGCCAGCCTGG<br>CGATTACCGGCCTGCAAGCAGAAGA<br>TGAAGCGGATTATTACTGCGACAGC<br>TGGGATCACAGCTCCATGAATGTTT<br>TTGGCGGCGGTACCAAGCTGACCGT<br>GCTGGGCCAGCCCAAAGCCGCCCCT<br>AGCGTGACCCTGTTCCCCCCCTCGA<br>GTGAGGAACTCCAGGCCAACAAGG<br>CCACCCTCGTGTGCCTGATCAGCGA<br>CTTCTACCCTGGCGCCGTGACCGTG<br>GCCTGGAAGGCCGATAGCAGCCCTG<br>TGAAGGCCGGCGTGGAAACCACCA<br>CCCCCAGCAAGCAGAGCAACAACA<br>AATACGCCGCCAGCAGCTACCTGAG<br>CCTGACCCCCGAGCAGTGGAAGTCC<br>CACAGATCCTACAGCTGCCAGGTCA<br>CACACGAGGGCAGCACCGTGGAAA<br>AGACCGTGGCCCCCACCGAGTGCAG<br>C |

MAB#1 DNA (optimized)

| | | SEQ ID NO: | |
|---|---|---|---|
| HCDR1 (Kabat) | | SEQ ID NO: 70 | AGCTACGCTATGCAC |
| HCDR2 (Kabat) | | SEQ ID NO: 71 | CGGATCAAGAGCAAGGCTCAAGGC<br>GGCACCACCGATTACGCCGCTCATG<br>TGAAGGGC |
| HCDR3 (Kabat) | | SEQ ID NO: 72 | GTGTCCTTCTCCACCTTCGATGTG |
| HCDR1 (Chothia) | | SEQ ID NO: 73 | GGCTTCACCTTCTCCAGCTAC |
| HCDR2 (Chothia) | | SEQ ID NO: 74 | AAGAGCAAGGCTCAAGGCGGCACC |
| HCDR3 (Chothia) | | SEQ ID NO: 72 | GTGTCCTTCTCCACCTTCGATGTG |
| LCDR1 (Kabat) | | SEQ ID NO: 75 | TCCGGCTCCTCCTCCAACATCGGCT<br>CCTACTACGTGTCC |
| LCDR2 (Kabat) | | SEQ ID NO: 76 | CGGAACAACCAGCGGCCTTCT |
| LCDR3 (Kabat) | | SEQ ID NO: 77 | GACTCTTGGGACCACTCCTCCATGA<br>ACGTG |
| LCDR1 (Chothia) | | SEQ ID NO: 75 | TCCGGCTCCTCCTCCAACATCGGCT<br>CCTACTACGTGTCC |
| LCDR2 (Chothia) | | SEQ ID NO: 76 | CGGAACAACCAGCGGCCTTCT |
| LCDR3 (Chothia) | | SEQ ID NO: 77 | GACTCTTGGGACCACTCCTCCATGA<br>ACGTG |
| VH | | SEQ ID NO: 78 | GAAGTGCAGCTGGTGGAATCTGGCG<br>GCGGACTTGTGAAACCTGGCGGCTC<br>TCTGAGACTGTCTTGTGCCGCTTCCG<br>GCTTCACCTTCTCCAGCTACGCTATG<br>CACTGGGTCCGACAGGCCCCTGGCA<br>AAGGATTGGAGTGGGTCGGACGGA<br>TCAAGAGCAAGGCTCAAGGCGGCA<br>CCACCGATTACGCCGCTCATGTGAA<br>GGGCAGATTCACCATCTCTCGGGAC<br>GACTCCAAGAACACCCTGTACCTGC<br>AGATGAACTCCCTGAAAACCGAGG<br>ACACCGCCGTGTACTACTGCGCCAG<br>AGTGTCCTTCTCCACCTTCGATGTGT<br>GGGGCCAGGGCACACTGGTTACAGT<br>CTCGAGC |
| VL | | SEQ ID NO: 79 | CAGTCCGTGCTGACCCAGCCTCCTT<br>CTGTTTCTGGTGCTCCTGGCCAGAG<br>AGTGACCATCTCTTGCTCCGGCTCCT<br>CCTCCAACATCGGCTCCTACTACGT<br>GTCCTGGTATCAGCAGCTGCCTGGC<br>ACCGCTCCTAAGGTGCTGATCTACC<br>GGAACAACCAGCGGCCTTCTGGCGT |

TABLE 1-continued

Antibody sequences of MAB#1

| MAB#1 | SEQ ID NO: | [aa]/DNA |
|---|---|---|
| | | GCCCGATAGATTCTCCGGCTCTAAG<br>TCTGGCACCTCTGCCAGCCTGGCTA<br>TCACTGGACTGCAGGCTGAGGACGA<br>GGCCGACTACTACTGCGACTCTTGG<br>GACCACTCCTCCATGAACGTGTTCG<br>GCGGAGGTACCAAGCTGACCGTGCT<br>GGGACAG |
| Heavy chain (IgG1)<br>IgG1 AEASS | SEQ ID NO: 80 | GAAGTGCAGCTGGTGGAATCTGGCG<br>GCGGACTTGTGAAACCTGGCGGCTC<br>TCTGAGACTGTCTTGTGCCGCTTCCG<br>GCTTCACCTTCTCCAGCTACGCTATG<br>CACTGGGTCCGACAGGCCCCTGGCA<br>AAGGATTGGAGTGGGTCGGACGGA<br>TCAAGAGCAAGGCTCAAGGCGGCA<br>CCACCGATTACGCCGCTCATGTGAA<br>GGGCAGATTCACCATCTCTCGGGAC<br>GACTCCAAGAACACCCTGTACCTGC<br>AGATGAACTCCCTGAAAACCGAGG<br>ACACCGCCGTGTACTACTGCGCCAG<br>AGTGTCCTTCTCCACCTTCGATGTGT<br>GGGGCCAGGGCACACTGGTTACAGT<br>CTCGAGCGCCTCCACCAAAGGACCC<br>TCTGTGTTTCCTCTGGCTCCCTCCAG<br>CAAGTCTACCTCTGGTGGAACAGCT<br>GCCCTGGGCTGCCTGGTCAAGGATT<br>ACTTTCCTGAGCCTGTGACCGTGTC<br>CTGGAACTCTGGCGCTCTGACATCT<br>GGCGTGCACACCTTTCCAGCTGTGC<br>TGCAGTCCTCTGGCCTGTACAGCCT<br>GTCCTCTGTCGTGACCGTGCCTTCTA<br>GCTCTCTGGGCACCCAGACCTACAT<br>CTGCAATGTGAACCACAAGCCTTCC<br>AACACCAAGGTGGACAAGAGAGTG<br>GAACCCAAGTCCTGCGACAAGACCC<br>ACACCTGTCCTCCATGTCCTGCTCCA<br>GAAGCTGAGGGCGCTCCTTCCGTGT<br>TCCTGTTTCCTCCAAAGCCTAAGGA<br>CACCCTGATGATCTCTCGGACCCCT<br>GAAGTGACCTGCGTGGTGGTGGATG<br>TGTCTCACGAGGACCCAGAAGTGAA<br>GTTCAATTGGTACGTGGACGGCGTG<br>GAAGTGCACAACGCCAAGACCAAG<br>CCTAGAGAGGAACAGTACAACTCCA<br>CCTACAGAGTGGTGTCCGTGCTGAC<br>CGTGCTGCACCAGGATTGGCTGAAC<br>GGCAAAGAGTACAAGTGCAAGGTG<br>TCCAACAAGGCCCTGCCTTCCAGCA<br>TCGAAAAGACCATCTCCAAGGCCAA<br>GGGCCAGCCTAGGGAACCCCAGGTT<br>TACACCCTGCCTCCAAGCCGGGAAG<br>AGATGACCAAGAACCAGGTGTCCCT<br>GACCTGCCTCGTGAAGGGCTTCTAC<br>CCTTCCGATATCGCCGTGGAATGGG<br>AGAGCAATGGCCAGCCTGAGAACA<br>ACTACAAGACAACCCCTCCTGTGCT<br>GGACTCCGACGGCTCATTCTTCCTG<br>TACTCCAAGCTGACAGTGGACAAGT<br>CCAGATGGCAGCAGGGCAACGTGTT<br>CTCCTGCTCCGTGATGCACGAGGCC<br>CTGCACAATCACTACACACAGAAGT<br>CCCTGTCTCTGTCCCCTGGCAAG |
| Light chain (DNA) | SEQ ID NO: 81 | CAGTCCGTGCTGACCCAGCCTCCTT<br>CTGTTTCTGGTGCTCCTGGCCAGAG<br>AGTGACCATCTCTTGCTCCGGCTCCT<br>CCTCCAACATCGGCTCCTACTACGT<br>GTCCTGGTATCAGCAGCTGCCTGGC<br>ACCGCTCCTAAGGTGCTGATCTACC<br>GGAACAACCAGCGGCCTTCTGGCGT<br>GCCCGATAGATTCTCCGGCTCTAAG<br>TCTGGCACCTCTGCCAGCCTGGCTA<br>TCACTGGACTGCAGGCTGAGGACGA<br>GGCCGACTACTACTGCGACTCTTGG<br>GACCACTCCTCCATGAACGTGTTCG<br>GCGGAGGTACCAAGCTGACCGTGCT<br>GGGACAGCCTAAGGCTGCCCCTTCC<br>GTGACACTGTTCCCTCCATCCTCTGA |

TABLE 1-continued

Antibody sequences of MAB#1

| MAB#1 | SEQ ID NO: | [aa]/DNA |
|---|---|---|
| | | GGAACTGCAGGCCAACAAGGCTAC |
| | | CCTCGTGTGCCTGATCTCCGACTTTT |
| | | ACCCTGGCGCTGTGACCGTGGCCTG |
| | | GAAGGCTGATAGTTCTCCTGTGAAG |
| | | GCCGGCGTGGAAACCACCACACCTT |
| | | CCAAGCAGTCCAACAACAAATACGC |
| | | CGCCTCCTCCTACCTGTCTCTGACCC |
| | | CTGAACAGTGGAAGTCCCACCGGTC |
| | | CTACAGCTGCCAAGTGACCCATGAG |
| | | GGCTCCACCGTGGAAAAGACCGTGG |
| | | CTCCTACCGAGTGCTCT |

TABLE 2

Antibody sequences of MAB#2

| MAB#2 | SEQ ID NO: | [aa]/DNA |
|---|---|---|
| | MAB#2 Protein | |
| HCDR1 (Kabat) | SEQ ID NO: 27 | SYAMH |
| HCDR2 (Kabat) | SEQ ID NO: 39 | RIKSVAQGGTTDYAAHVKG |
| HCDR3 (Kabat) | SEQ ID NO: 40 | VSHSTFDV |
| HCDR1 (Chothia) | SEQ ID NO: 30 | GFTFSSY |
| HCDR2 (Chothia) | SEQ ID NO: 41 | KSVAQGGT |
| HCDR3 (Chothia) | SEQ ID NO: 40 | VSHSTFDV |
| LCDR1 (Kabat) | SEQ ID NO: 32 | SGSSSNIGSYYVS |
| LCDR2 (Kabat) | SEQ ID NO: 33 | RNNQRPS |
| LCDR3 (Kabat) | SEQ ID NO: 34 | DSWDHSSMNV |
| LCDR1 (Chothia) | SEQ ID NO: 32 | SGSSSNIGSYYVS |
| LCDR2 (Chothia) | SEQ ID NO: 33 | RNNQRPS |
| LCDR3 (Chothia) | SEQ ID NO: 34 | DSWDHSSMNV |
| VH | SEQ ID NO: 42 | EVQLVESGGGLVKPGGSLRLSCAAS GFTFSSYAMHWVRQAPGKGLEWVG RIKSVAQGGTTDYAAHVKGRFTISR DDSKNTLYLQMNSLKTEDTAVYYC ARVSHSTFDVWGQGTLVTVSS |
| VL | SEQ ID NO: 43 | QSVLTQPPSVSGAPGQRVTISCSGSSS NIGSYYVSWYQQLPGTAPKVLIYRN NQRPSGVPDRFSGSKSGTSASLAITG LQAEDEADYYCDSWDHSSMNVFGG GTKLTVLGQ |
| Heavy chain IgG1_AEASS | SEQ ID NO: 44 | EVQLVESGGGLVKPGGSLRLSCAAS GFTFSSYAMHWVRQAPGKGLEWVG RIKSVAQGGTTDYAAHVKGRFTISR DDSKNTLYLQMNSLKTEDTAVYYC ARVSHSTFDVWGQGTLVTVSSASTK GPSVFPLAPSSKSTSGGTAALGCLVK DYFPEPVTVSWNSGALTSGVHTFPA VLQSSGLYSLSSVVTVPSSSLGTQTYI CNVNHKPSNTKVDKRVEPKSCDKTH TCPPCPAPEAEGAPSVFLFPPKPKDTL MISRTPEVTCVVVDVSHEDPEVKFN WYVDGVEVHNAKTKPREEQYNSTY RVVSVLTVLHQDWLNGKEYKCKVS NKALPSSIEKTISKAKGQPREPQVYT LPPSREEMTKNQVSLTCLVKGFYPSD IAVEWESNGQPENNYKTTPPVLDSD GSFFLYSKLTVDKSRWQQGNVFSCS VMHEALHNHYTQKSLSLSPGK |
| Light chain | SEQ ID NO: 45 | QSVLTQPPSVSGAPGQRVTISCSGSSS NIGSYYVSWYQQLPGTAPKVLIYRN NQRPSGVPDRFSGSKSGTSASLAITG LQAEDEADYYCDSWDHSSMNVFGG GTKLTVLGQPKAAPSVTLFPPSSEEL QANKATLVCLISDFYPGAVTVAWKA DSSPVKAGVETTTPSKQSNNKYAAS SYLSLTPEQWKSHRSYSCQVTHEGST VEKTVAPTECS |

TABLE 2-continued

Antibody sequences of MAB#2

| MAB#2 | | SEQ ID NO: | [aa]/DNA |
|---|---|---|---|
| | | MAB#2 DNA | |
| HCDR1 (Kabat) | | SEQ ID NO: 58 | AGCTATGCGATGCAC |
| HCDR2 (Kabat) | | SEQ ID NO: 59 | CGTATCAAATCCGTGGCCCAGGGC GGTACGACCGACTACGCGGCGCAC GTGAAAGGC |
| HCDR3 (Kabat) | | SEQ ID NO: 60 | GTTTCTCATTCCACTTTCGATGTT |
| HCDR1 (Chothia) | | SEQ ID NO: 61 | GGATTTACCTTCAGCAGCTAT |
| HCDR2 (Chothia) | | SEQ ID NO: 62 | AAATCCGTGGCCCAGGGCGGTACG |
| HCDR3 (Chothia) | | SEQ ID NO: 60 | GTTTCTCATTCCACTTTCGATGTT |
| LCDR1 (Kabat) | | SEQ ID NO: 63 | AGCGGCAGCTCCTCCAATATTGGT AGCTATTACGTGAGC |
| LCDR2 (Kabat) | | SEQ ID NO: 64 | CGTAATAATCAACGTCCTAGC |
| LCDR3 (Kabat) | | SEQ ID NO: 65 | GACAGCTGGGATCACAGCTCCATG AATGTT |
| LCDR1 (Chothia) | | SEQ ID NO: 63 | AGCGGCAGCTCCTCCAATATTGGT AGCTATTACGTGAGC |
| LCDR2 (Chothia) | | SEQ ID NO: 64 | CGTAATAATCAACGTCCTAGC |
| LCDR3 (Chothia) | | SEQ ID NO: 65 | GACAGCTGGGATCACAGCTCCATG AATGTT |
| VH | | SEQ ID NO: 66 | GAGGTGCAATTGGTGGAAAGCGGC GGTGGCCTGGTGAAACCAGGCGGC AGCCTGCGCCTGAGCTGCGCCGCC TCCGGATTTACCTTCAGCAGCTATG CGATGCACTGGGTGCGCCAGGCCC CGGGCAAAGGTCTCGAATGGGTGG GTCGTATCAAATCCGTGGCCCAGG GCGGTACGACCGACTACGCGGCGC ACGTGAAAGGCCGCTTTACCATTA GCCGCGATGATTCGAAAAACACCC TGTATCTGCAAATGAACAGCCTGA AAACCGAAGATACGGCCGTGTATT ATTGCGCGCGTGTTTCTCATTCCAC TTTCGATGTTTGGGGCCAAGGCACC CTGGTGACTGTCTCGAGC |
| VL | | SEQ ID NO: 67 | CAGAGCGTGCTGACCCAGCCTCCT AGCGTGAGCGGTGCACCGGGCCAG CGCGTGACCATTAGCTGTAGCGGC AGCTCCTCCAATATTGGTAGCTATT ACGTGAGCTGGTATCAGCAGCTGC CGGGCACGGCGCCGAAAGTTCTGA TCTATCGTAATAATCAACGTCCTAG CGGCGTGCCGGATCGCTTTAGCGG ATCCAAAAGCGGCACCAGCGCCAG CCTGGCGATTACCGGCCTGCAAGC AGAAGATGAAGCGGATTATTACTG CGACAGCTGGGATCACAGCTCCAT GAATGTTTTGGCGGCGGTACCAA GCTGACCGTGCTGGGCCAG |
| Heavy chain (IgG1) | | SEQ ID NO: 68 | GAGGTGCAATTGGTGGAAAGCGGC GGTGGCCTGGTGAAACCAGGCGGC AGCCTGCGCCTGAGCTGCGCCGCC TCCGGATTTACCTTCAGCAGCTATG CGATGCACTGGGTGCGCCAGGCCC CGGGCAAAGGTCTCGAATGGGTGG GTCGTATCAAATCCGTGGCCCAGG GCGGTACGACCGACTACGCGGCGC ACGTGAAAGGCCGCTTTACCATTA GCCGCGATGATTCGAAAAACACCC TGTATCTGCAAATGAACAGCCTGA AAACCGAAGATACGGCCGTGTATT ATTGCGCGCGTGTTTCTCATTCCAC TTTCGATGTTTGGGGCCAAGGCACC CTGGTGACTGTCTCGAGCGCGTCG ACCAAAGGCCCCAGCGTGTTCCCT CTGGCCCCCAGCAGCAAGAGCACC TCTGGCGGAACAGCCGCCCTGGGC TGCCTGGTCAAGGACTACTTCCCCG AGCCCGTGACCGTGTCCTGGAACT CTGGCGCCCTGACCAGCGGCGTGC ACACCTTTCCAGCCGTGCTCCAGAG CAGCGGCCTGTACAGCCTGAGCAG CGTCGTGACCGTGCCCAGCAGCAG CCTGGGCACCCAGACCTACATCTG CAACGTGAACCACAAGCCCAGCAA |

TABLE 2-continued

Antibody sequences of MAB#2

| MAB#2 | SEQ ID NO: | [aa]/DNA |
|---|---|---|
| IgG1 AEASS | | CACAAAGGTGGACAAGCGGGTGGA<br>ACCCAAGAGCTGCGACAAGACCCA<br>CACCTGTCCCCCCTGCCCTGCCCCT<br>GAAGCGGAGGGAGCCCCCTCCGTG<br>TTCCTGTTCCCCCCAAAGCCTAAGG<br>ACACCCTGATGATCAGCCGGACCC<br>CCGAAGTGACCTGCGTGGTGGTGG<br>ACGTGTCCCACGAGGACCCTGAAG<br>TGAAGTTTAATTGGTACGTGGACG<br>GCGTGGAAGTGCACAACGCCAAGA<br>CCAAGCCCAGAGAGGAACAGTACA<br>ACAGCACCTACCGGGTGGTGTCCG<br>TGCTGACCGTGCTGCACCAGGACT<br>GGCTGAACGGCAAAGAGTACAAGT<br>GCAAGGTGTCCAACAAGGCCCTGC<br>CTTCCTCCATCGAGAAAACCATCA<br>GCAAGGCCAAAGGCCAGCCCCGCG<br>AGCCCCAGGTGTACACACTGCCCC<br>CTAGCCGGGAAGAGATGACCAAGA<br>ACCAGGTGTCCCTGACCTGCCTCGT<br>GAAGGGCTTCTACCCCAGCGACAT<br>TGCCGTGGAATGGGAGAGCAACGG<br>CCAGCCCGAGAACAACTACAAGAC<br>CACCCCCCCTGTGCTGGACAGCGA<br>CGGCTCATTCTTCCTGTACAGCAAG<br>CTGACCGTGGACAAGAGCCGGTGG<br>CAGCAGGGCAACGTGTTCAGCTGC<br>TCCGTGATGCACGAGGCCCTGCAC<br>AACCACTACACCCAGAAGTCCCTG<br>AGCCTGAGCCCCGGCAAG<br>CAGAGCGTGCTGACCCAGCCTCCT<br>AGCGTGAGCGGTGCACCGGGCCAG<br>CGCGTGACCATTAGCTGTAGCGGC<br>AGCTCCTCCAATATTGGTAGCTATT<br>ACGTGAGCTGGTATCAGCAGCTGC<br>CGGGCACGGCGCCGAAAGTTCTGA<br>TCTATCGTAATAATCAACGTCCTAG<br>CGGCGTGCCGGATCGCTTTAGCGG<br>ATCCAAAAGCGGCACCAGCGCCAG<br>CCTGGCGATTACCGGCCTGCAAGC<br>AGAAGATGAAGCGGATTATTACTG |
| Light chain (DNA) | SEQ ID NO: 69 | CGACAGCTGGGATCACAGCTCCAT<br>GAATGTTTTTGGCGGCGGTACCAA<br>GCTGACCGTGCTGGGCCAGCCCAA<br>AGCCGCCCCTAGCGTGACCCTGTTC<br>CCCCCCTCGAGTGAGGAACTCCAG<br>GCCAACAAGGCCACCCTCGTGTGC<br>CTGATCAGCGACTTCTACCCTGGCG<br>CCGTGACCGTGGCCTGGAAGGCCG<br>ATAGCAGCCCTGTGAAGGCCGGCG<br>TGGAAACCACCACCCCCAGCAAGC<br>AGAGCAACAACAAATACGCCGCCA<br>GCAGCTACCTGAGCCTGACCCCCG<br>AGCAGTGGAAGTCCCACAGATCCT<br>ACAGCTGCCAGGTCACACACGAGG<br>GCAGCACCGTGGAAAAGACCGTGG<br>CCCCCACCGAGTGCAGC |

MAB#2 DNA OPTIMIZED

| | | |
|---|---|---|
| HCDR1 (Kabat) | SEQ ID NO: 82 | AGCTACGCTATGCAC |
| HCDR2 (Kabat) | SEQ ID NO: 83 | CGGATCAAGAGCGTTGCCCAAGGC<br>GGCACCACCGATTACGCTGCTCAT<br>GTGAAGGGC |
| HCDR3 (Kabat) | SEQ ID NO: 84 | GTGTCCCACTCTACCTTCGATGTG |
| HCDR1 (Chothia) | SEQ ID NO: 85 | GGCTTCACCTTCTCCAGCTAC |
| HCDR2 (Chothia) | SEQ ID NO: 86 | AAGAGCGTTGCCCAAGGCGGCACC |
| HCDR3 (Chothia) | SEQ ID NO: 84 | GTGTCCCACTCTACCTTCGATGTG |
| LCDR1 (Kabat) | SEQ ID NO: 87 | TCCGGCTCCTCCTCCAACATCGGCT<br>CCTACTACGTGTCC |
| LCDR2 (Kabat) | SEQ ID NO: 88 | CGGAACAACCAGCGGCCTTCT |
| LCDR3 (Kabat) | SEQ ID NO: 89 | GACTCTTGGGACCACTCCTCCATGA<br>ACGTG |
| LCDR1 (Chothia) | SEQ ID NO: 87 | TCCGGCTCCTCCTCCAACATCGGCT<br>CCTACTACGTGTCC |

TABLE 2-continued

Antibody sequences of MAB#2

| MAB#2 | | SEQ ID NO: | [aa]/DNA |
|---|---|---|---|
| | LCDR2 (Chothia) | SEQ ID NO: 88 | CGGAACAACCAGCGGCCTTCT |
| | LCDR3 (Chothia) | SEQ ID NO: 89 | GACTCTTGGGACCACTCCTCCATGA<br>ACGTG |
| | VH | SEQ ID NO: 90 | GAAGTGCAGCTGGTGGAATCTGGC<br>GGCGGACTTGTGAAACCTGGCGGC<br>TCTCTGAGACTGTCTTGTGCCGCTT<br>CCGGCTTCACCTTCTCCAGCTACGC<br>TATGCACTGGGTCCGACAGGCCCC<br>TGGCAAAGGATTGGAGTGGGTCGG<br>ACGGATCAAGAGCGTTGCCCAAGG<br>CGGCACCACCGATTACGCTGCTCAT<br>GTGAAGGGCAGATTCACCATCAGC<br>CGGGACGACTCCAAGAACACCCTG<br>TACCTGCAGATGAACTCCCTGAAA<br>ACCGAGGACACCGCCGTGTACTAC<br>TGCGCCAGAGTGTCCCACTCTACCT<br>TCGATGTGTGGGGCCAGGGCACAC<br>TGGTTACAGTCTCGAGC |
| | VL | SEQ ID NO: 91 | CAGTCCGTGCTGACCCAGCCTCCTT<br>CTGTTTCTGGTGCTCCTGGCCAGAG<br>AGTGACCATCTCTTGCTCCGGCTCC<br>TCCTCCAACATCGGCTCCTACTACG<br>TGTCCTGGTATCAGCAGCTGCCTGG<br>CACCGCTCCTAAGGTGCTGATCTAC<br>CGGAACAACCAGCGGCCTTCTGGC<br>GTGCCCGATAGATTCTCCGGCTCTA<br>AGTCTGGCACCTCTGCCAGCCTGGC<br>TATCACTGGACTGCAGGCTGAGGA<br>CGAGGCCGACTACTACTGCGACTC<br>TTGGGACCACTCCTCCATGAACGTG<br>TTCGGCGGAGGTACCAAGCTGACC<br>GTGCTGGGACAG |
| | Heavy chain (IgG1)<br>IgG1 AEASS | SEQ ID NO: 92 | GAAGTGCAGCTGGTGGAATCTGGC<br>GGCGGACTTGTGAAACCTGGCGGC<br>TCTCTGAGACTGTCTTGTGCCGCTT<br>CCGGCTTCACCTTCTCCAGCTACGC<br>TATGCACTGGGTCCGACAGGCCCC<br>TGGCAAAGGATTGGAGTGGGTCGG<br>ACGGATCAAGAGCGTTGCCCAAGG<br>CGGCACCACCGATTACGCTGCTCAT<br>GTGAAGGGCAGATTCACCATCAGC<br>CGGGACGACTCCAAGAACACCCTG<br>TACCTGCAGATGAACTCCCTGAAA<br>ACCGAGGACACCGCCGTGTACTAC<br>TGCGCCAGAGTGTCCCACTCTACCT<br>TCGATGTGTGGGGCCAGGGCACAC<br>TGGTTACAGTCTCGAGCGCCTCCAC<br>CAAAGGACCCTCTGTGTTTCCTCTG<br>GCTCCCTCCAGCAAGTCTACCTCTG<br>GTGGAACAGCTGCCCTGGGCTGCC<br>TGGTCAAGGATTACTTTCCTGAGCC<br>TGTGACCGTGTCCTGGAACTCTGGC<br>GCTCTGACATCTGGCGTGCACACCT<br>TTCCAGCTGTGCTGCAGTCCTCTGG<br>CCTGTACAGCCTGTCCTCTGTCGTG<br>ACCGTGCCTTCTAGCTCTCTGGGCA<br>CCCAGACCTACATCTGCAATGTGA<br>ACCACAAGCCTTCCAACACCAAGG<br>TGGACAAGAGAGTGGAACCCAAGT<br>CCTGCGACAAGACCCACACCTGTC<br>CTCCATGTCCTGCTCCAGAAGCTGA<br>GGGCGCTCCTTCCGTGTTCCTGTTT<br>CCTCCAAAGCCTAAGGACACCCTG<br>ATGATCTCTCGGACCCCTGAAGTG<br>ACCTGCGTGGTGGTGGATGTGTCTC<br>ACGAGGACCCAGAAGTGAAGTTCA<br>ATTGGTACGTGGACGGCGTGGAAG<br>TGCACAACGCCAAGACCAAGCCTA<br>GAGAGGAACAGTACAACTCCACCT<br>ACAGAGTGGTGTCCGTGCTGACCG<br>TGCTGCACCAGGATTGGCTGAACG<br>GCAAAGAGTACAAGTGCAAGGTGT<br>CCAACAAGGCCCTGCCTTCCAGCA<br>TCGAAAAGACCATCTCCAAGGCCA<br>AGGGCCAGCCTAGGGAACCCCAGG<br>TTTACACCCTGCCTCCAAGCCGGGA |

TABLE 2-continued

Antibody sequences of MAB#2

| MAB#2 | | SEQ ID NO: | [aa]/DNA |
|---|---|---|---|
| Light chain (DNA) | | SEQ ID NO: 93 | AGAGATGACCAAGAACCAGGTGTC<br>CCTGACCTGCCTCGTGAAGGGCTTC<br>TACCCTTCCGATATCGCCGTGGAAT<br>GGGAGAGCAATGGCCAGCCTGAGA<br>ACAACTACAAGACAACCCCTCCTG<br>TGCTGGACTCCGACGGCTCATTCTT<br>CCTGTACTCCAAGCTGACAGTGGA<br>CAAGTCCAGATGGCAGCAGGGCAA<br>CGTGTTCTCCTGCTCCGTGATGCAC<br>GAGGCCCTGCACAATCACTACACA<br>CAGAAGTCCCTGTCTCTGTCCCCTG<br>GCAAG<br>CAGTCCGTGCTGACCCAGCCTCCTT<br>CTGTTTCTGGTGCTCCTGGCCAGAG<br>AGTGACCATCTCTTGCTCCGGCTCC<br>TCCTCCAACATCGGCTCCTACTACG<br>TGTCCTGGTATCAGCAGCTGCCTGG<br>CACCGCTCCTAAGGTGCTGATCTAC<br>CGGAACAACCAGCGGCCTTCTGGC<br>GTGCCCGATAGATTCTCCGGCTCTA<br>AGTCTGGCACCTCTGCCAGCCTGGC<br>TATCACTGGACTGCAGGCTGAGGA<br>CGAGGCCGACTACTACTGCGACTC<br>TTGGGACCACTCCTCCATGAACGTG<br>TTCGGCGGAGGTACCAAGCTGACC<br>GTGCTGGGACAGCCTAAGGCTGCC<br>CCTTCCGTGACACTGTTCCCTCCAT<br>CCTCTGAGGAACTGCAGGCCAACA<br>AGGCTACCCTCGTGTGCCTGATCTC<br>CGACTTTTACCCTGGCGCTGTGACC<br>GTGGCCTGGAAGGCTGATAGTTCT<br>CCTGTGAAGGCCGGCGTGGAAACC<br>ACCACACCTTCCAAGCAGTCCAAC<br>AACAAATACGCCGCCTCCTCCTACC<br>TGTCTCTGACCCCTGAACAGTGGA<br>AGTCCCACCGGTCCTACAGCTGCC<br>AAGTGACCCATGAGGGCTCCACCG<br>TGGAAAAGACCGTGGCTCCTACCG<br>AGTGCTCT |

TABLE 3

Antibody sequences of RefMAB#1

| RefMAB#1 | | SEQ ID NO: | [aa] |
|---|---|---|---|
| | | RefMAB#1 Protein | |
| Heavy chain IgG1_AEASS | SEQ ID NO: 94 | | EVQLVESGGGLVQPGGSLRLSCAASG<br>FTFSSYVMHWVRQATGKGLEWVSAI<br>DTGGGTYYADSVKGRFTISRENAKNS<br>LYLQMNSLRAGDTAVYYCARDYYYY<br>ASGSYYKAFDIWGQGTMVTVSSASTK<br>GPSVFPLAPSSKSTSGGTAALGCLVKD<br>YFPEPVTVSWNSGALTSGVHTFPAVL<br>QSSGLYSLSSVVTVPSSSLGTQTYICN<br>VNHKPSNTKVDKRVEPKSCDKTHTCP<br>PCPAPEAEGAPSVFLFPPKPKDTLMIS<br>RTPEVTCVVVDVSHEDPEVKFNWYV<br>DGVEVHNAKTKPREEQYNSTYRVVS<br>VLTVLHQDWLNGKEYKCKVSNKALP<br>SSIEKTISKAKGQPREPQVYTLPPSREE<br>MTKNQVSLTCLVKGFYPSDIAVEWES<br>NGQPENNYKTTPPVLDSDGSFFLYSK<br>LTVDKSRWQQGNVFSCSVMHEALHN<br>HYTQKSLSLSPGK |
| Light chain | SEQ ID NO: 95 | | EIVLTQSPGTLSLSPGERATLSCRASQS<br>VSSRYLAWYQQKPGQAPRLLIYGASS<br>RATGIPDRFSGSGSGTDFTLTISRLEPE<br>DFAVYYCQQYGSPLTFGQGTKLEIKR<br>TVAAPSVFIFPPSDEQLKSGTASVVCL<br>LNNFYPREAKVQWKVDNALQSGNSQ<br>ESVTEQDSKDSTYSLSSTLTLSKADYE<br>KHKVYACEVTHQGLSSPVTKSFNRGE<br>C |

WORKING EXAMPLES

Example 1: Antigen Generation and Quality Control

Amino acid sequences of C5aR and C5aR related GPCRs from various species were retrieved from publicly available sources (e.g. Uniprot), verified and produced in-house or by external service providers.

Synthetic Peptides

As antigens for the initial panning and screening, linear peptides covering the N-terminal extracellular region of human C5aR were used. The peptides were chemically synthesized with a biotin tag (JPT), RP-HPLC purified and delivered as lyophilized material. The lyophilized peptides were stored at −80° C. Alternatively, the peptides were conjugated to Transferrin or bovine serum albumin (BSA).

TABLE 4

Amino acid sequence of N-terminal human C5aR peptide used for initial panning and screening.
N-terminal C5aR peptides

| | | |
|---|---|---|
| Human | SEQ ID NO: 12 | MDSFNYTTPDYGHYDDKDTLDLNTPV DKTSN |

As antigens for later binding studies, linear peptides comprising the N-terminal region of human and cynomolgus monkey C5aR were used. The peptides were chemically synthesized with a biotin tag (Genscript), RP-HPLC purified and delivered as lyophilized material. The lyophilized peptides were stored at −80° C. For reconstitution, peptides were dissolved in the desired volume of PBS and stored at −80° C.

TABLE 5

Amino acid sequences of N-terminal C5aR peptides used for binding studies.
N-terminal C5aR peptides (C5aR_NT peptide)

| | | |
|---|---|---|
| Human | SEQ ID NO: 13 | MDSFNYTTPDYGHYDDKDTLDLNTPVDKTSN TLRVPD |
| Cynomolgus | SEQ ID NO: 14 | MDPFSSTTLDYEHYDGKNVLDSDTPVDKTSN TLRVPD |

Recombinant Proteins

C1q Protein

C1q protein purified from pooled normal human plasma was purchased from Complement Technology, Inc. (Catalog #A099).

Human C5a Protein

Recombinant human C5a was either purchased from R&D Systems (CAT #: 2037-C5) or was produced in house.

For in-house production, DNA encoding the amino acids of human C5a (Uniprot: P01031|Lys679-Arg751) was cloned into a pET21a expression vector (Novagen®) in frame with an N-terminal ompA signal sequence followed by a sequence coding for maltose-binding protein (MBP), a FXa cleavage site and a GS linker.

Human C5a (hC5a) was expressed in E. coli BL21 (DE3) cells (Novagen®) as a N-terminally tagged maltose-binding protein (MBP)-fusion protein. Protein expression was induced by the addition of IPTG and cultures were further cultivated for 20-23 h. Cells were harvested by centrifugation and the pellet was resuspended in lysis buffer (PBS buffer plus 2 mM $MgCl_2$, 20 U/ml Benzonase (Roche) and 1 tablet/50 ml cOmplete™, EDTA-free protease inhibitor cocktail tablets (Roche)). Cells were disrupted either by chemical lysis or high-pressure homogenization. The resulting suspension was centrifuged and the supernatant was sterile filtered for further purification steps.

The hC5a-MBP-fusion protein was purified by Dextrin-Sepharose affinity chromatography using a MBP-Trap column (GE-Healthcare) and optionally polished by cation exchange chromatography using a Hi-Trap™ SP FF column (GE LifeSciences). The purified MBP-fusions were buffer-exchanged by PD10 columns (GE Healthcare) into FXa-digest buffer (20 mM Tris/HCl pH 8.0; 100 mM NaCl; 2 mM CaCl2). The hC5a protein was released from the maltose-binding protein by addition of Factor Xa (1:100 (w/w)) and incubation O/N in a rotary shaker at room temperature. The released hC5a was purified by cation exchange chromatography using a Hi-Trap™ SP FF column (GE LifeSciences).

All affinity chromatography steps were performed using an ÄKTA™ Avant 25 preparative chromatography system.

Buffer exchange to PBS was performed using PD 10 columns (GE Healthcare). Samples were sterile filtered and hC5a concentration was determined by UV-spectrophotometry. The purity and integrity of the samples were analyzed in denaturing, reducing or non-reducing SDS-PAGE, SEC-HPLC and mass spectrometry.

Fc Gamma Receptors (FcγR) and FcRn Receptors

DNA encoding the extracellular region of human FcγRI, human FcγRIIa (131H), human FcγRIIa (131R), human FcγRIIb, human FcγRIIIa (158F) and human FcγRIIIa (158V) were cloned in frame with an N-terminal Vκ leader sequence and a C-terminal 6×His-tag into a pMAX expression vector, which is a modified expression vector based on pcDNA3.1 (Thermo Fisher).

DNA encoding the extracellular region of human, cynomolgus, mouse or rat FcRn large subunit p51 was cloned in frame with an N-terminal Vκ leader sequence and a C-terminal AVI-6×His-tag into a pMAX expression vector, which is a modified expression vector based on pcDNA3.1 (Thermo Fisher). In addition, DNA encoding human, cynomolgus monkey, mouse or rat FcRn small subunit p14 (=identical with beta-2 microglobulin) protein was cloned into a second open reading frame in frame with an N-terminal Vk leader sequence. The amino acid sequences of the produced receptors are summarized in Table 6 and 7.

The HEK293-6E cell line was developed by the National Research Council of Canada (NRC). Cells were maintained in Freestyle™ F17 medium (Thermo Scientific) in a humidified CO2-incubator at 37° C. and 6% $CO_2$. HKB11 (Parental clone: U.S. Pat. No. 6,136,599. J. Biomed. Sci. 2002; 9:631-638) is a human hybrid cell line resulting from a fusion of HEK293 human embryonic kidney and 2B8 Burkitt lymphoma cells. HKB11 #52 cells were maintained in MAC1.0 medium containing 1% FCS in a humidified $CO_2$ incubator at 37° C. and 6% $CO_2$.

HKB11 #52 or HEK293-6E cells were transiently transfected one day post seeding with a commercially available transfection reagent according to the manufacturer's instructions. The cells were cultured for 3 days and the conditioned cell culture supernatant was harvested by centrifugation followed by sterile filtration (0.22 μm). Stably transfected HKB11 #52 pools were generated by transfection of cells followed by selection with 800 μg/mL G418 (Thermo Scientific). Expression of antigens from stable pools was done for 4 days post seeding. The conditioned cell culture supernatants were harvested by centrifugation followed by sterile filtration (0.22 μm).

The respective proteins were purified by IMAC using Protino® Ni-NTA columns (Macherey-Nagel). All chromatography steps were performed using ÄKTA™ chromatography systems (GE Healthcare). The samples were buffer-exchanged to D-PBS using PD10 columns (GE Healthcare). In some cases, a polishing preparative SEC step was performed in D-PBS using a Superdex® 200 column (GE Healthcare).

Biotinylation of FcRn heterodimers was performed by in vitro biotinylation using the BirA Kit (Avidity) followed by a preparative SEC using a Superdex® 200 column (GE Healthcare).

The quality of the samples was analyzed by denaturing, reducing or non-reducing SDS-PAGE, Streptavidin-Shift Assay, HP-SEC and DLS.

TABLE 6

Amino acid sequences of produced FcRn proteins.

| FcRn Fusion Protein | UniProt IDs: | SEQ ID NO: | Protein sequence |
|---|---|---|---|
| Human FcRn p51 [1-297]/AviHis/p14 biotinylated | P55899 (p51) P61769 (p14) | SEQ ID NO: 15 | AESHLSLLYHLTAVSSPAPGTPAFWVSG WLGPQQYLSYNSLRGEAEPCGAWVWEN QVSWYWEKETTDLRIKEKLFLEAFKALG GKGPYTLQGLLGCELGPDNTSVPTAKFA LNGEEFMNFDLKQGTWGGDWPEALAIS QRWQQQDKAANKELTFLLFSCPHRLREH LERGRGNLEWKEPPSMRLKARPSSPGFS VLTCSAFSFYPPELQLRFLRNGLAAGTGQ GDFGPNSDGSFHASSSLTVKSGDEHHYC CIVQHAGLAQPLRVELESPAKSSVNSRGL NDIFEAQKIEWHEHHHHHHIQRTPKIQVY SRHPAENGKSNFLNCYVSGFHPSDIEVDL LKNGERIEKVEHSDLSFSKDWSFYLLYY TEFTPTEKDEYACRVNHVTLSQPKIVKW DRDM |
| Cynomolgus FcRn p51 [1-297]_AviHis/ p14 biotinylated | Q8SPV9 (p51) P61769 (p14) | SEQ ID NO: 16 | AESHLSLLYHLTAVSSPAPGTPAFWVSG WLGPQQYLSYDSLRGQAEPCGAWVVWE NQVSWYWEKETTDLRIKEKLFLEAFKAL GGKGPYTLQGLLGCELSPDNTSVPTAKF ALNGEEFMNFDLKQGTWGGDWPEALAI SQRWQQQDKAANKELTFLLFSCPHRLRE HLERGRGNLEWKEPPSMRLKARPGNPGF SVLTCSAFSFYPPELQLRFLRNGMAAGT GQGDFGPNSDGSFHASSSLTVKSGDEHH YCCIVQHAGLAQPLRVELETPAKSSVNS RGLNDIFEAQKIEWHEHHHHHHIQRTPKI QVYSRHPPENGKPNFLNCYVSGFHPSDIE VDLLKNGEKMGKVEHSDLSFSKDWSFY LLYYTEFTPNEKDEYACRVNHVTLSGPR TVKWDRDM |
| Mouse FcRn p51 [1-297]/AviHis/p14 biotinylated | Q61559 (p51) P61769 (p14) | SEQ ID NO: 17 | SETRPPLMYHLTAVSNPSTGLPSFWATG WLGPQQYLTYNSLRQEADPCGAWMWE NQVSWYWEKETTDLKSKEQLFLEALKT LEKILNGTYTLQGLLGCELASDNSSVPTA VFALNGEEFMKFNPRIGNWTGEWPETEI VANLWMKQPDAARKESEFLLNSCPERLL GHLERGRRNLEWKEPPSMRLKARPGNS GSSVLTCAAFSFYPPELKFRFLRNGLASG SGNCSTGPNGDGSFHAWSLLEVKRGDEH HYQCQVEHEGLAQPLTVDLDSSARSSVN SRGLNDIFEAQKIEWHEHHHHHHIQKTP QIQVYSRHPPENGKPNILNCYVTQFHPPH IEIQMLKNGKKIPKVEMSDMSFSKDWSF YILAHTEFTPTETDTYACRVKHDSMAEP KTVYWDRDM |
| Rat FcRn p51 [1-298]/AviHis/p14 biotinylated | P13599 (p51) P61769 (p14) | SEQ ID NO: 96 | AEPRLPLMYHLAAVSDLSTGLPSFWATG WLGAQQYLTYNNLRQEADPCGAWIWE NQVSWYWEKETTDLKSKEQLFLEAIRTL ENQINGTFTLQGLLGCELAPDNSSLPTAV FALNGEEFMRFNPRTGNWSGEWPETDIV GNLWMKQPEAARKESEFLLTSCPERLLG HLERGRQNLEWKEPPSMRLKARPGNSGS SVLTCAAFSFYPPELKFRFLRNGLASGSG NCSTGPNGDGSFHAWSLLEVKRGDEHH YQCQVEHEGLAQPLTVDLDSPARSSVNS RGLNDIFEAQKIEWHEHHHHHHIQKTPQI QVYSRHPPENGKPNFLNCYVSQFHPPQIE IELLKNGKKIPNIEMSDLSFSKDWSFYILA HTEFTPTETDVYACRVKHVILKEPKTVT WDRDM |

TABLE 7

Amino acid sequences of produced human FcγR proteins.

| FcγR Fusion Protein | UniProt IDs: | SEQ ID NO: | Protein sequence |
|---|---|---|---|
| Human FcγRI (1-279)_HIS$_6$ | P12314 | SEQ ID NO: 18 | QVDTTKAVITLQPPWVSVFQEETVTLHC EVLHLPGSSSTQWFLNGTATQTSTPSYRI TSASVNDSGEYRCQRGLSGRSDPIQLEIH RGWLLLQVSSRVFTEGEPLALRCHAWK DKLVYNVLYYRNGKAFKFFHWNSNLTIL KTNISHNGTYHCSGMGKHRYTSAGISVT VKELFPAPVLNASVTSPLLEGNLVTLSCE TKLLLQRPGLQLYFSFYMGSKTLRGRNT SSEYQILTARREDSGLYWCEAATEDGNV LKRSPELELQVNSRHHHHHH |
| Human FcγRIIa (1-209)-(131H)-HIS$_6$(133-2) | P12318 | SEQ ID NO: 19 | QAAAPPKAVLKLEPPWINVLQEDSVTLT CQGARSPESDSIQWFHNGNLIPTHTQPSY RFKANNNDSGEYTCQTGQTSLSDPVHLT VLSEWLVLQTPHLEFQEGETIMLRCHSW KDKPLVKVTFFQNGKSQKFSHLDPTFSIP QANHSHSGDYHCTGNIGYTLFSSKPVTIT VQVPSVNSRHHHHHH |
| Human FcγRIIa (1-209)-(131R)-HIS$_6$ (137-3) | P12318 | SEQ ID NO: 20 | QAAAPPKAVLKLEPPWINVLQEDSVTLT CQGARSPESDSIQWFHNGNLIPTHTQPSY RFKANNNDSGEYTCQTGQTSLSDPVHLT VLSEWLVLQTPHLEFQEGETIMLRCHSW KDKPLVKVTFFQNGKSQKFSRLDPTFSIP QANHSHSGDYHCTGNIGYTLFSSKPVTIT VQVPSVNSRHHHHHH |
| Human FcγRIIIa (1-193)-(158F)-HIS$_6$ (141-2) | P08637 | SEQ ID NO: 21 | GMRTEDLPKAVVFLEPQWYRVLEKDSV TLKCQGAYSPEDNSTQWFHNESLISSQAS SYFIDAATVDDSGEYRCQTNLSTLSDPVQ LEVHIGWLLLQAPRWVFKEEDPIHLRCH SWKNTALHKVTYLQNGKGRKYFHHNSD FYIPKATLKDSGSYFCRGLFGSKNVSSET VNITITQGVNSRHHHHHH |
| Human FcγRIIIa (1-193)-(158V)-HIS$_6$ | P08637 | SEQ ID NO: 22 | GMRTEDLPKAVVFLEPQWYRVLEKDSV TLKCQGAYSPEDNSTQWFHNESLISSQAS SYFIDAATVDDSGEYRCQTNLSTLSDPVQ LEVHIGWLLLQAPRWVFKEEDPIHLRCH SWKNTALHKVTYLQNGKGRKYFHHNSD FYIPKATLKDSGSYFCRGLVGSKNVSSET VNITITQGVNSRHHHHHH |
| Human FcγRIIB (1-202)-HIS$_6$ | P31994 | SEQ ID NO: 23 | TPAAPPKAVLKLEPQWINVLOEDSVTLT CRGTHSPESDSIQWFHNGNLIPTHTQPSY RFKANNNDSGEYTCQTGQTSLSDPVHLT VLSEWLVLQTPHLEFQEGETIVLRCHSW KDKPLVKVTFFQNGKSKKFSRSDPNFSIP QANHSHSGDYHCTGNIGYTLYSSKPVTIT VQAPSDNSRHHHHHH |

Virus-Like-Particles (VLPs)

VLPs stably expressing either one of the two natural variants of human C5aR (D/K variant or N/N variant) as well as mouse C5aR were generated in house as described in WO 2015/193143. All cloning experiments were performed using standard technologies. Antigens of interest were cloned in a suited two vector system for the expression in mammalian cells. In this system, one vector expresses GAG and the other vector expresses the GPCR-GAG fusion protein. Expression in these vectors is under the control of the CMV promoter. Subsequently, host cells were transfected with the two vectors. The generated constructs were produced as fusion proteins, in which the antigen of interest is fused N-terminal to the GAG-protein (HV1B1 (Uni-Prot ID: P03347)). Expression of the proteins and production of the VLPs was done under standard conditions in suspension cultures. Host cells used in the present experiments were HKB11 cells (ATCC; CRL-12568) and HEK cells (Life Technologies). Three days post transfection the supernatants containing the VLPs were harvested and purified using standard procedures (including precipitation and ion exchange chromatography). The proteins isolated were subjected to SDS-PAGE chromatography. The supernatants were probed with a commercial anti-GAG antibody or a commercial anti-C5aR antibody and revealed that co-expression of GAG and a GPCR-GAG fusion protein resulted in a high expression level of GAG and GPCR-GAG in the VLPs. This confirmed that the C5aR antigens were efficiently integrated into the VLPs, and that the C5aR antigens were detectable with antibodies. The amino acid sequences of the produced fusion proteins are summarized in Table 8.

TABLE 8

Protein sequences of C5aR-GAG fusion protein expressed on virus-like-particles.

| C5aR-HV1B1 fusion protein | SEQ ID NO: | Protein sequence |
| --- | --- | --- |
| HIS$_6$-human C5aR (D/K variant)-HV1B1-GAG | SEQ ID NO: 24 | DGSHHHHHHGTMDSFNYTTPDYGHYDDKDTLDLNTP VDKTSNTLRVPDILALVIFAVVFLVGVLGNALVVWVT AFEAKRTINAIWFLNLAVADFLSCLALPILFTSIVQHHH WPFGGAACSILPSLILLNMYASILLLATISADRFLLVFK PIWCQNFRGAGLAWIACAVAWGLALLLTIPSFLYRVV REEYFPPKVLCGVDYSHDKRRERAVAIVRLVLGFLWP LLTLTICYTFILLRTWSRRATRSTKTLKVVVAVVASFFI FWLPYQVTGIMMSFLEPSSPTFLLLKKLDSLCVSFAYI NCCINPIIYVVAGQGFQGRLRKSLPSLLRNVLTEESVV RESKSFTRSTVDTMAQKTQAVDIDYKDDDDKIEGRM DGARASVLSGGELDRWEKIRLRPGGKKKYKLKHIVW ASRELERFAVNPGLLETSEGCRQILGQLQPSLQTGSEEL RSLYNTVATLYCVHQRIEIKDTKEALDKIEEEQNKSKK KAQQAAADTGHSSQVSQNYPIVQNIQGQMVHQAISPR TLNAWVKVVEEKAFSPEVIPMFSALSEGATPQDLNTM LNTVGGHQAAMQMLKETINEEAAEWDRVHPVHAGPI APGQMREPRGSDIAGTTSTLQEQIGWMTNNPPIPVGEI YKRWIILGLNKIVRMYSPTSILDIRQGPKEPFRDYVDRF YKTLRAEQASQEVKNWMTETLLVQNANPDCKTILKA LGPAATLEEMMTACQGVGGPGHKARVLAEAMSQVT NTATIMMQRGNFRNQRKMVKCFNCGKEGHTARNCR APRKKGCWKCGKEGHQMKDCTERQANFLGKIWPSY KGRPGNFLQSRPEPTAPPFLQSRPEPTAPPEESFRSGVE TTTPPQKQEPIDKELYPLTSLRSLFGNDPSSQVNSRGLN DIFEAQKIEWHE |
| HIS$_6$-human C5aR (N/N variant)-HV1B1-GAG | SEQ ID NO: 25 | DGSHHHHHHGTMNSFNYTTPDYGHYDDKDTLDLNTP VDKTSNTLRVPDILALVIFAVVFLVGVLGNALVVWVT AFEAKRTINAIWFLNLAVADFLSCLALPILFTSIVQHHH WPFGGAACSILPSLILLNMYASILLLATISADRFLLVFK PIWCQNFRGAGLAWIACAVAWGLALLLTIPSFLYRVV REEYFPPKVLCGVDYSHDKRRERAVAIVRLVLGFLWP LLTLTICYTFILLRTWSRRATRSTKTLKVVVAVVASFFI FWLPYQVTGIMMSFLEPSSPTFLLLNKLDSLCVSFAYI NCCINPIIYVVAGQGFQGRLRKSLPSLLRNVLTEESVV RESKSFTRSTVDTMAQKTQAVDIGARASVLSGGELDR WEKIRLRPGGKKKYKLKHIVWASRELERFAVNPGLLE TSEGCRQILGQLQPSLQTGSEELRSLYNTVATLYCVHQ RIEIKDTKEALDKIEEEQNKSKKKAQQAAADTGHSSQ VSQNYPIVQNIQGQMVHQAISPRTLNAWVKVVEEKAF SPEVIPMFSALSEGATPQDLNTMLNTVGGHQAAMQM LKETINEEAAEWDRVHPVHAGPIAPGQMREPRGSDIA GTTSTLQEQIGWMTNNPPIPVGEIYKRWIILGLNKIVR MYSPTSILDIRQGPKEPFRDYVDRFYKTLRAEQASQEV KNWMTETLLVQNANPDCKTILKALGPAATLEEMMTA CQGVGGPGHKARVLAEAMSQVTNTATIMMQRGNFR NQRKMVKCFNCGKEGHTARNCRAPRKKGCWKCGKE GHQMKDCTERQANFLGKIWPSYKGRPGNFLQSRPEPT APPFLQSRPEPTAPPEESFRSGVETTTPPQKQEPIDKELY PLTSLRSLFGNDPSSQ |
| HIS$_6$-mouse C5aR-HV1B1-GAG | SEQ ID NO: 26 | DGSHHHHHHGTMDPIDNSSFEINYDHYGTMAPNIPAD GIHLPKRQPGDVAALIIYSVVFLVGVPGNALVVWVTA FEARRAVNAIWFLNLAVADLLSCLALPVLFTTVLNHN YWYFDATACIVLPSLILLNMYASILLLATISADRFLLVF KPIWCQKVRGTGLAWMACGVAWVLALLLTIPSFVYR EAYKDFYSEHTVCGINYGGGSFPKEKAVAILRLMVGF VLPLLTLNICYTFLLLRTWSRKATRSTKTLKVVMAVVI CFFIFWLPYQVTGVMIAWLPPSSPTLKRVEKLNSLCVS LAYINCCVNPIIYVMAGQGFHGRLLRSLPSIIRNALSED SVGRDSKTFTPSTTDTSTRKSQAVDIDYKDDDDKIEGR MDGARASVLSGGELDRWEKIRLRPGGKKKYKLKHIV WASRELERFAVNPGLLETSEGCRQILGQLQPSLQTGSE ELRSLYNTVATLYCVHQRIEIKDTKEALDKIEEEQNKS KKKAQQAAADTGHSSQVSQNYPIVQNIQGQMVHQAI SPRTLNAWVKVVEEKAFSPEVIPMFSALSEGATPQDLN TMLNTVGGHQAAMQMLKETINEEAAEWDRVHPVHA GPIAPGQMREPRGSDIAGTTSTLQEQIGWMTNNPPIPV GEIYKRWIILGLNKIVRMYSPTSILDIRQGPKEPFRDYV DRFYKTLRAEQASQEVKNWMTETLLVQNANPDCKTI LKALGPAATLEEMMTACQGVGGPGHKARVLAEAMS QVTNTATIMMQRGNFRNQRKMVKCFNCGKEGHTAR NCRAPRKKGCWKCGKEGHQMKDCTERQANFLGKIW |

TABLE 8-continued

Protein sequences of C5aR-GAG fusion protein expressed on virus-like-particles.

| C5aR-HV1B1 fusion protein | SEQ ID NO: | Protein sequence |
|---|---|---|
| | | PSYKGRPGNFLQSRPEPTAPPFLQSRPEPTAPPEESFRS GVETTTPPQKQEPIDKELYPLTSLRSLFGNDPSSQVNSR GLNDIFEAQKIEWHE |

Cell Lines

CHO Flp-In cells stably expressing full length human C5aR, cynomolgus C5aR, mouse C5aR, rat C5aR and the C5aR related GPCRs human C5L2, human C3aR, human FPR1 and human ChemR23 were generated. For the generation of Flp-In CHO cells, various vector constructs were gene synthesized in-house and transfection of cells was performed according to the instructor's manual (Thermofischer/Invitrogen). All constructs contained an N-terminal V5/His tag. Commercially available anti-His (e.g. Dianova CAT #DIA-910) or anti-V5 (e.g. AbD Serotec CAT #MCA2285GA) detection antibodies were used to confirm the expression of the respective GPCR on the surface of the cell line, even in the absence of a commercially available specific anti-GPCR tool antibody.

Example 2: Generation of Human C5aR Specific Antibodies from the HuCAL PLATINUM® Library For antibody generation, the HuCAL Platinum® library was used to select for antibodies with specificity for human C5aR. The HuCAL PLATINUM® library is a phagemid library based on the HuCAL® concept (Knappik et al., (2000) J Mol Biol 296:57-86) and employs the CysDisplay® technology for displaying the Fab on the phage surface (Lohning et al., WO2001/05950).

To identify human C5aR specific antibodies, panning strategies were performed using human and cynomolgus monkey C5aR antigen material to select species cross-reactive antibodies. Each conducted panning comprised of at least 3 individual rounds of selection against various C5aR antigens (either as soluble recombinant antigens or overexpressed on cells).

Although the overall homology between cynomolgus and human C5aR with 90% is rather high, the extracellular domains share only 75% identity of the protein sequences. Indeed, the identification of cynomolgus C5aR cross-reactive antibodies turned out to be challenging, with the ancestor antibody of MAB #1 and MAB #2 being one of a few candidates revealing specific cell binding to human C5aR expressed on cells, cross-reactivity to cynomolgus monkey C5aR and no binding to other related GPCRs.

Bead based solution pannings against peptides representing the N-terminus (NT) of human C5aR were conducted which resulted in the identification of the ancestor antibody of MAB #1 and MAB #2 with specificity for human and cynomolgus monkey C5aR and being able to bind to full-length human C5aR expressed on cells.

This clone was subjected to two consecutively conducted affinity maturation panning using CHO Flp-In™ cells engineered to overexpress either human or cynomolgus C5aR in order to further increase affinity and specificity for human and cynomolgus C5aR. In addition, antibody engineering was conducted to further increase specificity, to remove potential posttranslational modification sites (PTM motifs) and for germlining purposes.

With this last step of engineering process, MAB #1 and MAB #2 were identified as potential therapeutic candidates. Since both candidates, MAB #1 and MAB #2 are derived from the same ancestors, they share similar amino acid sequences and in vitro characteristics.

These two antibodies are further described in the examples as outlined below.

Example 3: Production of Human C5aR Specific Antibodies

Both, MAB #1 and MAB #2 are of the human IgG1f isotype but are engineered in the Fc region to abolish the ability of the antibodies to mediate immune effector function. The Fc region comprises 5 amino acid substitutions compared to the wild-type human IgG1 Fc region, namely L234A, L235E, G237A, A330S and P331S (h_IgG1f_AEASS) with numbering according EU index.

The antibodies consist of the heavy chain framework VH3-15 and the antibody light chain framework lambda 1.

Transient Antibody Production—Advanced Micro Scale Production HKB11

Eukaryotic HKB11 #52 cells were transiently transfected with mammalian expression vectors encoding heavy and light chains of MAB #1 or MAB #2 (human IgG1_AEASS), respectively. Cell culture supernatants were harvested 7 days post transfection and subjected to Protein A affinity chromatography (MabSelect SuRe™|GE Healthcare) using a liquid handling station. The samples remained in neutralized elution buffer (NaPS: 137 mM NaPhosphate, 81 mM NaCl, pH 7). Samples were sterile filtered (0.2 µm pore size). Protein concentrations were determined by UV-spectrophotometry at 280 nm and purity of IgG was analysed under denaturing, reducing conditions using CE-SDS (LabChip® GXII|Perkin Elmer). UHP-SEC was performed to analyse IgG preparations in native state.

Transient Antibody Production—Exploratory Scale Production in CHO

CHO3-E7 cells were transiently transfected with mammalian expression vector encoding heavy and light chains of MAB #1 or MAB #2 (human IgG1_AEASS), respectively. Cell culture supernatants were harvested on day 6 post transfection and subjected to standard Protein A affinity chromatography (MabSelect SuRe™|GE Healthcare). If not stated otherwise, buffer exchange was performed to 1× Dulbecco's PBS (pH 7.2|Invitrogen) and samples were sterile filtered (0.2 µm pore size). Protein concentrations were determined by UV-spectrophotometry at 280 nm and purity of IgG was analysed under denaturing, reducing and non-reducing conditions using CE-SDS (LabChip® GXII|Perkin Elmer). UHP-SEC was performed to analyse IgG preparations in native state.

Results Transient Production

Data on product quality (SEC monomer content) and productivity of MAB #1 and MAB #2 are summarized in Table 9. Overall, acceptable monomer contents (>95%) and yields (>55 mg/L in HKB11 cells) were achieved. Volumetric yields derived from CHO3E-7 transient Exploratory Scale productions were also in the expected range.

TABLE 9

Production data of MAB#1 and MAB#2 in transient expression

| Antibody | Production Platform | SEC Monomer [%] | Volumetric yield [mg/L] |
|---|---|---|---|
| MAB#1 | Advanced Micro HKB11 | 97.5 | 56.1 |
|  | Exploratory CHO | 96.4 | 3.0 |
| MAB#2 | Advanced Micro HKB11 | 97.4 | 58.9 |
|  | Exploratory CHO | 98.5 | 2.4 |

Generation of Stable HKB11 Pools

For the generation of HKB11 #52 pools stably expressing MAB #1 or MAB #2, a two-vector system was used for co-transfection.

In order to facilitate pool selection these vectors contain Zeocin and Neomycin resistance cassettes. The two vectors were transiently co-transfected into actively dividing HKB11 #52 cells in a 1:1 ratio. One day post transfection selection was started by the addition of 160 µg/mL Zeocin and 800 µg/mL Geneticin to the cell suspension. During the selection cell count and viability initially decreased. 20 days after transfection cells started to recover. Reaching a viability of ~80%, stable pools were scaled up to the desired volume depending on the amount needed. Cell culture supernatants of the batch productions were harvested on day 6 post seeding.

Large Scale Purification of MAB #1 and MAB #2

Purification of MAB #1 and MAB #2 from cell culture supernatants of HKB11 #52 stable pools via Protein A affinity chromatography (MabSelect SuRe™|GE Healthcare) was performed using 100 mM Citrate, 150 mM NaCl pH 3.5 as elution buffer. After incubation at pH 3.5 for 60 minutes, the samples were neutralized. Buffer exchange was performed into 150 mM Histidine, pH 6.0 and samples were sterile filtered (0.2 µm pore size). Protein concentrations were determined by UV-spectrophotometry at 280 nm and purity of IgG was analysed under denaturing, reducing and non-reducing conditions using CE-SDS (LabChip® GXII|Perkin Elmer). UHP-SEC was performed to analyse IgG preparations in native state.

Results Large Scale Production

As summarized in Table 10, production of MAB #1 and MAB #2 resulted in favorable yields, purity and integrity.

TABLE 10

Production data of MAB#1 and MAB#2 derived from stable cell pool expressions.

| Antibody | Production Platform | SEC Monomer [%] | HMW [%] | LMW [%] | Volumetric yield [mg/L] |
|---|---|---|---|---|---|
| MAB#1 | Large Scale HKB11 | 99.1 | 0.5 | 0.4 | 60.5 |
| MAB#2 | Large Scale HKB11 | 99.1 | 0.6 | 0.3 | 100.5 |

Control Antibodies

Various control antibodies were produced and included in experiments for comparative purposes:

RefMAB #1: Benchmark Antibody

Nucleotide sequences encoding the VH and VL region from the human C5aR specific antibody "IPH5401" were retrieved from US patent application US2013/0295116 (NOVO NORDISK—clone 32F3A6GL). Nucleotide sequences were gene synthesized as linear DNA fragments with appropriate flanking regions (e.g. suitable restriction enzyme recognition sites, linker sequences) either in-house or by an external provider. The DNA fragments were cloned into suited mammalian IgG expression vectors encoding heavy and light chains of human IgG1_AEASS as described above by using standard molecular biology methods. RefMAB #1 was transiently produced as described above. The heavy and light chain amino acid sequences of RefMAB #1 are depicted in Table 3.

Additional Control Antibodies:

An in-house negative isotype control antibody with specificity for hen-egg lysozyme (MOR03207) as well as an in-house positive control antibody (anti-C5aR antibody) with specificity for the N-terminus of human C5aR were transiently produced as described above either in human IgG1 or human IgG1_AEASS format.

Characterization of the Binding Properties of MAB #1 and MAB #2

Example 4: Monovalent Affinity Determination for MAB #1 and MAB #2 for C5aR N-Terminal Peptides Using SPR Method $K_D$ determination via IgG capture setup was performed at 25° C. with a Biacore® T200 instrument (Biacore®, GE Healthcare). Approx. 500 RU of IgG diluted in HBS-EP+, pH 7.4, were captured on a CM5 chip (Biacore®, GE Healthcare) immobilised with anti-human-Fc antibody (GE Healthcare) using standard EDC-NHS amine coupling chemistry. The reference flow cell 1 was only activated and deactivated. Kinetic measurements were done using 6 different human or cynomolgus C5aR_NT-bio peptide concentrations (SEQ ID NO: 13 or SEQ ID NO: 14, respectively) (2n serial dilution, 2000 to 62.5 nM) with HBS-EP+ (GE Healthcare) as running buffer (injection time 300 s; dissociation time 600 s; flow rate 30 µL/min). After each cycle the sensor chip was regenerated to remove bound peptide/antibody complex with 3×20 s injections of 3 mM $MgCl_2$. A blank injection of running buffer was used for double referencing. All sensorgrams were fitted using Biacore® T200 Evaluation Software 3.1, (Biacore®, GE Healthcare) to determine $k_{on}$ and $k_{off}$ rate constants, which were used to calculate $K_D$. The raw data was fitted with a 1:1 binding model, with parameters $R_{max}$ set to local and RI set to 0.

Results

Results are summarized in Table 11. Both antibodies revealed similar binding to the human C5aR peptide with $K_D$ values in the low double-digit nanomolar range and weaker binding to the cynomolgus C5aR peptide.

TABLE 11

Determination of association and dissociation rate constants for binding of MAB#1 and MAB#2 to human and cynomolgus C5aR N-terminal peptides.

| Antibody | Antigen | $k_{on}$ [1/Ms] | $k_{off}$ [1/s] | $K_D$ [nM] | Comment |
|---|---|---|---|---|---|
| MAB#2 | Human | 4.33E+04 | 1.27E−03 | 29 | |
| MAB#1 | C5aR_NT | 5.01E+04 | 1.79E−03 | 36 | |
| MAB#2 | Cynomolgus | *4.29E+03* | *1.45E−01* | *34000* | fast $k_{on}$, fast $k_{off}$ |
| MAB#1 | C5aR_NT | *1.36E+04* | *1.11E−07* | *8200* | fast $k_{on}$, fast $k_{off}$ |

*Values formatted in grey italics are intended for ranking purposes.

Example 5: Apparent Affinity (Bivalent) Determination of MAB #1 and MAB #2 for C5aR N-Terminal Peptides Using Octet®

Method

Apparent $K_D$ determination via C5aR_NT-bio peptide capture setup was performed at 27° C. with the Octet® HTX instrument (FortéBIO, Pall Life Sciences). Approx. 0.03 nm of peptide diluted in PBS, pH 7.4, were loaded onto streptavidin (SA) sensors (FortéBIO, Pall Life Sciences). Kinetic measurements were done using 7 different IgG concentrations (3-fold serial dilution, 200 to 0.27 nM for human C5aR_NT-bio peptide (SEQ ID NO: 13) and 1000 to 1.4 nM for cynomolgus C5aR_NT-bio peptide (SEQ ID NO: 14) in Octet® buffer (PBS, 0.05% (v/v) Tween-20, 0.1% (w/v) BSA) with 480 s association time and 900 s dissociation time. After each dissociation step the sensors were regenerated to remove bound antibody (3×30 s Gly/HCl, pH 1.5). All sensorgrams were fitted using Octet® Data Analysis Software 10.0 (FortéBIO) to determine apparent $k_{on}$ and app. $k_{off}$ rate constants, which were used to calculate apparent $K_D$ (using a 1:1 binding model).

Results

Results are summarized in Table 12. Both antibodies revealed strong binding to the human C5aR peptide in bivalent format with apparent $K_D$ values in the double to triple digit picomolar range. Binding to the cynomolgus C5aR peptide was approx. 1000-fold weaker. The observed weaker binding to cynomolgus monkey C5aR peptide appeared mainly due to fast $k_{off}$ rates. In terms of apparent affinities to human C5aR_NT, MAB #2 exhibited an about 10-fold weaker binding affinity compared to MAB #1 ($K_D$: 290 pM vs. 20 pM).

TABLE 12

Determination of apparent association and dissociation rate constants for binding of MAB#1 and MAB#2 to human and cynomolgus C5aR N-terminal peptide.

| Antibody | Antigen Name | Apparent $k_{on}$ [1/Ms] | Apparent $k_{off}$ [1/s] | Apparent $K_D$ [nM] | Comment |
|---|---|---|---|---|---|
| MAB#2 | Human | 3.78E+05 | 1.11E−04 | 0.29 | |
| MAB#1 | C5aR_NT | 4.76E+05 | 9.99E−06 | 0.02 | |
| MAB#2 | Cynomolgus | 1.38E+05 | 1.89E−02 | 140 | fast $k_{off}$ |
| MAB#1 | C5aR_NT | 1.71E+05 | 1.08E−02 | 63 | fast $k_{off}$ |

Example 6: Apparent Affinity (Bivalent) Determination for MAB #1 on Full-Length C5aR Expressed on Cells by Using KinExA®

Since C5aR belongs to the family of GPCRs, it is very difficult to generate recombinant full-length antigen material that can be used for SPR measurements. Therefore, Flp-In™ CHO cells stably expressing human C5aR or cynomolgus C5aR and KinExA® measurements were performed.

Method

Apparent $K_D$ determination on C5aR-expressing cells was performed at RT with a KinExA® 3200 instrument (Sapidyne Instruments). PBS (Gibco), supplemented with BSA (1 mg/mL) and 0.02% (v/v) NaN$_3$ was used as assay buffer. MAB #1 (conc.: of 2 nM and 30 pM) was used as analyte and Flip-In CHO hC5aR_V5/His cells (final concentration 3 Mio cells/mL and 1 Mio cells/mL, 2n serial dilution) or Flp-In™ CHO cyC5aR_V5/His cells (final concentration 25 Mio cells/ml and 6 Mio cells/ml, 2n serial dilution) as titrant and equilibrated over night at RT in an overhead shaker. After equilibration, the samples were centrifuged and the supernatants were used for analysis. Free concentration of MAB #1 was determined using polymethylmethacrylate (PMMA) beads coated with MabSSL (GE Healthcare) and anti-human Fab2 Alexa Fluor 647 (500 ng/mL) was used for detection. The apparent $K_D$ was obtained using KinExA® software and by "n-curve analysis," which fits all of the given curves to a single $K_D$ value simultaneously.

Results

Results are summarized in Table 13. MAB #1 revealed strong binding to full-length human C5aR with an apparent $K_D$ value of 130 pM. Binding to full-length cynomolgus C5aR appeared about 20× weaker with an apparent $K_D$ value of approx. 3 nM. Similar findings concerning binding to cynomolgus C5aR were observable before in Octet® and Biacore® measurements (see Example 4 and Example 5).

TABLE 13

Bivalent binding of MAB#1 to full-length human and cynomolgus C5aR expressed on Flp-In ™ CHO cells

| | Flp-In CHO | Apparent $K_D$ [nM] |
|---|---|---|
| MAB#1 | human_C5aR | 0.130 |
| | cyno_C5aR | 2.98 |

Example 7: Binding of MAB #1 and MAB #2 to Full-Length C5aR Expressed on Flp-In CHO Cells and Whole-Blood Derived Neutrophils (FACS Analysis)

Cell binding to CHO Flp-In™ cell lines stably expressing various full-length C5aR antigens and related GPCRs as well as binding to purified human or cynomolgus neutrophils, expressing human or cynomolgus C5aR endogenously, was investigated via FACS. Cynomolgus neutrophils were obtained from whole-blood of cynomolgus monkey from three different animals (LPT Hamburg).

Methods

The C5aR-CHO Flp-In™ cell lines were blocked and IgGs were added either in serial dilutions or at a single (high) concentration of 300 nM. For detection of IgG binding, an R-phycoerythrin (R-PE) conjugated anti-human IgG (Fc-gamma fragment specific)2 antibody was added and fluorescence was measured using the FACS Array or Novocyte device.

Neutrophils were purified from EDTA-whole blood samples using a MACSexpress® Neutrophil Isolation Cocktail from Miltenyi Biotec. Briefly, using this kit, cells are isolated using magnetic labeling and negative magnetic separation. After removal of erythrocytes, the cells were stained by adding the IgGs in a serial dilution, followed by a Alexa Fluor 647-conjugated anti-Human F(ab)2 fragment specific detection antibody. Measurements were done at the FACS Array device. FACS data were evaluated using FlowJo™, entered into GraphPad® Prism (v4.0) and fitted to the sigmoidal dose-response curve using non-linear regression to calculate the EC50.

Results

Figure 2:
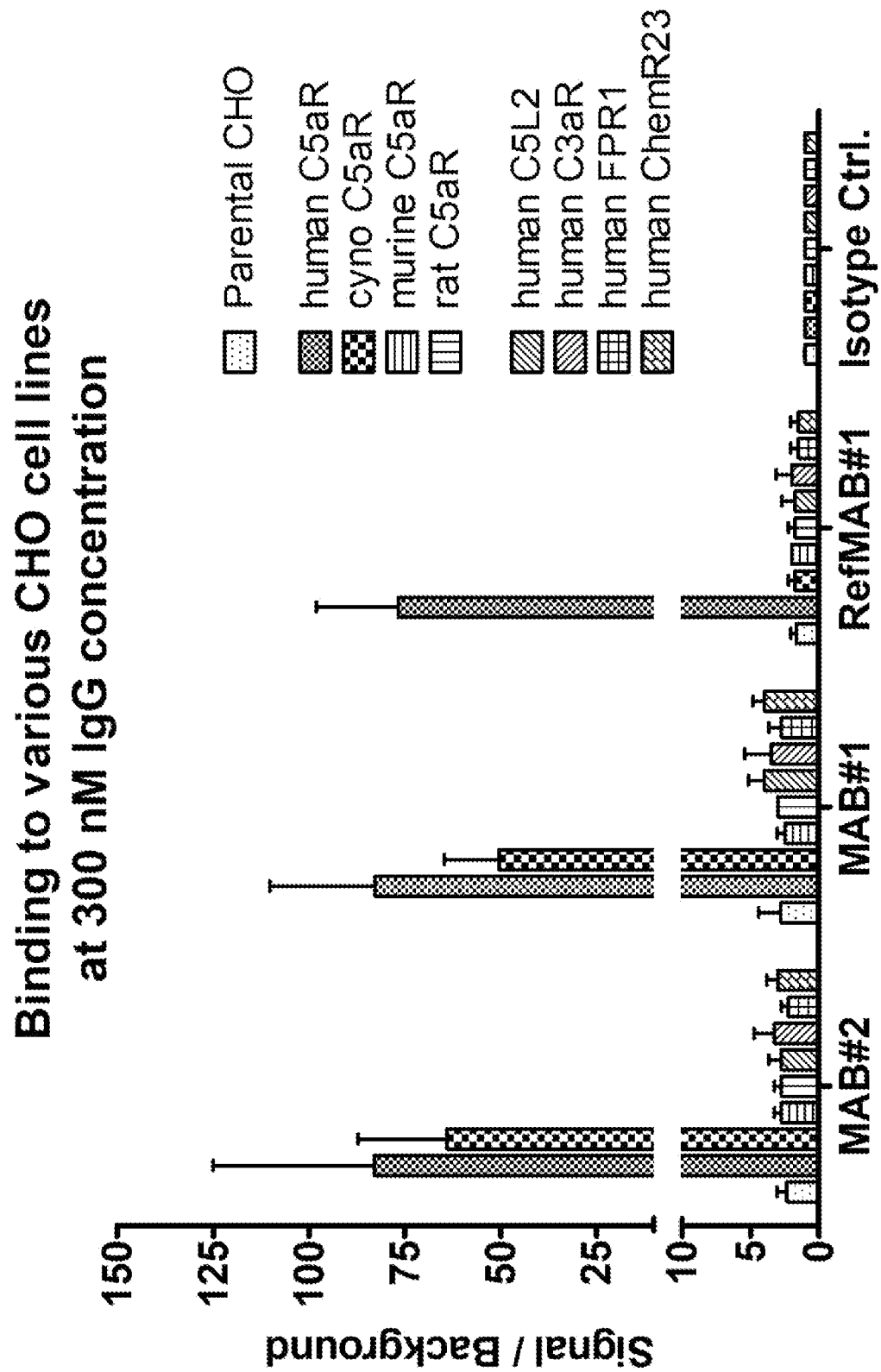
FIG. 2: Cell binding of MAB #1, MAB #2, RefMAB #1 and negative isotype control MOR03207 to human, cynomolgus and rodent C5aR as well as to the C5aR related GPCRs human C5L2, human C3aR, human FPR1 and human ChemR23 determined via FACS at an IgG concentration of 600 nM.

Results are summarized in Table 14 and FIGS. 1 and 2. FIGS. 1A and C depict binding of MAB #1, MAB #2 and RefMAB #1 to human and cynomolgus C5aR present on engineered CHO cells expressing the respective full-length receptor. Overall, very comparable binding curves on human C5aR with almost identical $EC_{50}$ concentrations were determined for MAB #1, MAB #2 and RefMAB #1. Similar results were obtained on cynomolgus C5aR for MAB #1 and MAB #2. As expected, RefMAB #1 revealed no binding to cynomolgus C5aR expressed on CHO cells.

Binding to cynomolgus and human C5aR was also confirmed using purified neutrophils obtained from human or cynomolgus whole-blood (FIGS. 1B and D). Again, very comparable binding curves with almost identical $EC_{50}$ values on human and cynomolgus neutrophils were observable for MAB #1. Interestingly, MAB #2 revealed overall lower signal over background levels on cynomolgus neutrophils when compared to MAB #1. This finding was not observable when binding to cynomolgus C5aR expressed on CHO cells was analyzed. Lack of binding to cynomolgus monkey neutrophils was confirmed for RefMAB #1

For rodent C5aR, no cross-reactivity to rat and mouse C5aR was expected due to the low sequence homology (66% overall identity). Indeed, neither MAB #1 nor MAB #2 showed any significant binding to rat or mouse C5aR expressed on CHO-Flp cell when tested at an IgG concentration of 300 nM (FIG. 2). In order to exclude cross-reactivity to any other member of the C5aR subfamily, binding to full-length human C5L2, ChemR23, FPR1 and C3aR expressed on CHO Flp-In™ cells was also determined via FACS (compared to non-transfected parental CHO Flp-In™ cells). As shown in FIG. 2, even at an IgG concentration of 300 nM, no significant cell binding of MAB #1 and MAB #2 was detectable to any of the C5aR-related GPCRs or to the parental CHO cells.

Taken together, both, MAB #1 and MAB #2 revealed specific binding to human and cynomolgus monkey C5aR.

TABLE 14

Binding of MAB#1, MAB#2 and RefMAB#1 to full-length human or cynomolgus C5aR expressed by engineered CHO cells or purified neutrophils. Each antibody was tested in at least in two independent assay runs.

| Full-length protein expressed on cells | MAB#1 | MAB#2 | RefMAB#1 |
|---|---|---|---|
| human C5aR expressed on CHO cells | $EC_{50}$ = 1.7 nM | $EC_{50}$ = 1.2 nM | $EC_{50}$ = 1.1 nM |
| C5aR expressed on purified human neutrophils | $EC_{50}$ = 6.0 nM | $EC_{50}$ = 5.4 nM | $EC_{50}$ = 3.1 nM |
| cynomolgus C5aR expressed on CHO cells | $EC_{50}$ = 1.1 nM | $EC_{50}$ = 1.4 nM | No binding |
| C5aR expressed on purified cynomolgus neutrophils | $EC_{50}$ = 4.5 nM | $EC_{50}$ = 3.8 nM | No binding |

Example 8: Binding of MAB #1 and MAB #2 to Full-Length Human C5aR Displayed on Virus-Like-Particles (VLPs)—Binding to Natural Variants of Human C5aR Two natural variants of human C5aR (SEQ ID NO: 1; D/K variant and SEQ ID NO: 2; N/N variant) are reported.

To compare binding of MAB #1 and Mab #2 to the two natural variants, VLPs expressing either of the two C5aR variants were generated as described in Example 1. As negative control, VLPs expressing murine C5aR were included, since MAB #1 and Mab #2 are not cross-reactive to murine C5aR.

Method

For assessment of binding, produced VLPs were coated overnight and after a blocking step, IgG titrations were added on the next day. Binding of the IgGs to the coated antigen was detected using an Alkaline Phosphatase-conjugated anti-human IgG2 antibody and AttoPhos® as substrate.

Results

Figure 3:
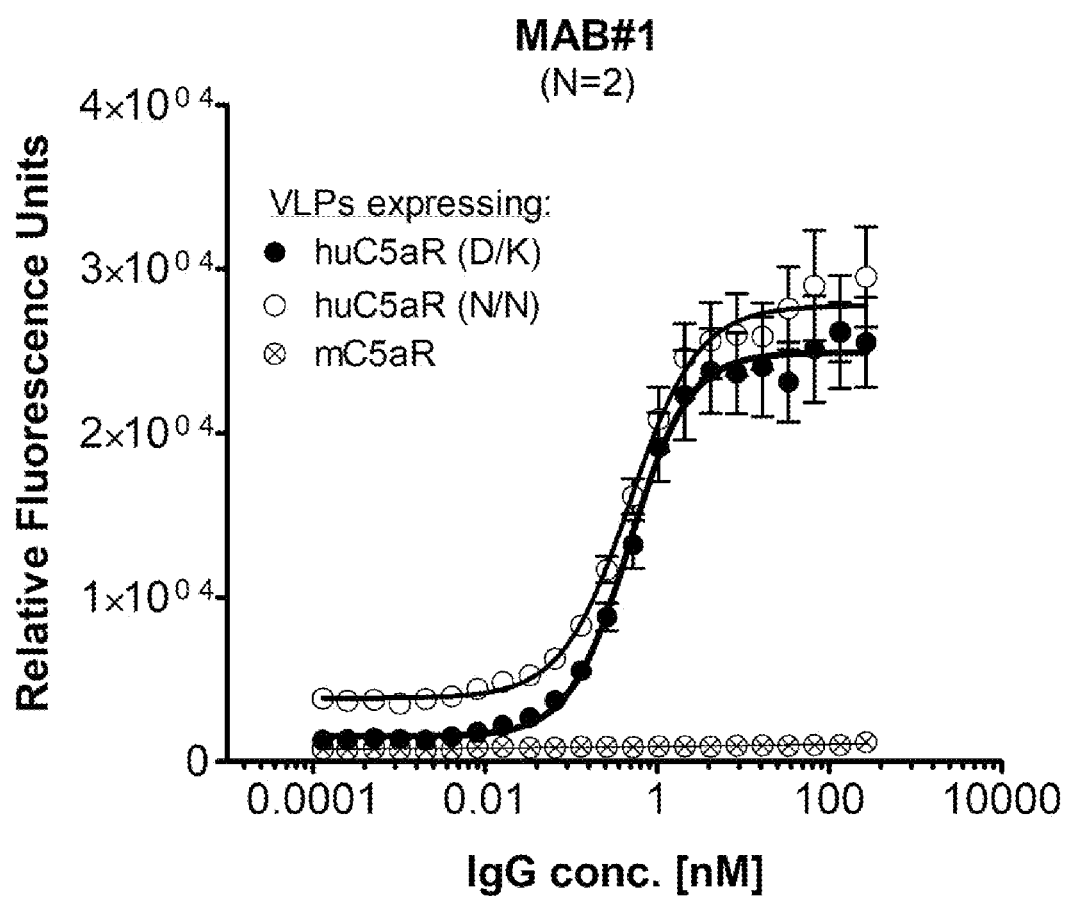
FIG. 3: ELISA binding of MAB #1 to two natural variants of human C5aR as well as to mouse C5aR expressed on virus-like-particles (VLPs).

Results are summarized in Table 15 and depicted in FIG. 3. Both, MAB #1 and MAB #2 revealed comparable titration curves on both natural variants of human C5aR with equal $EC_{50}$ concentrations. As expected, no binding to murine C5aR was detected. Based on these data, high affinity binding of MAB #1 and MAB #2 to human C5aR can be expected in vivo, independent of the natural variant present on the respective target cells.

TABLE 15

Binding of MAB#1 and MAB#2 to two natural variants of human C5aR expressed on VLPs.

| C5aR variant | MAB#1 | MAB#2 |
|---|---|---|
| huC5aR (D/K) | $EC_{50}$ = 0.5 nM (N = 2) | $EC_{50}$ = 0.5 nM (N = 2) |
| huC5aR (N/N) | $EC_{50}$ = 0.5 nM (N = 2) | $EC_{50}$ = 0.5 nM (N = 2) |

Example 9: Protein Panel Profiling (3P)

Potential unspecific off-target binding for MAB #1 was determined in the generic 3P assay.

Method:

Protein panel profiling was mainly performed as described by Frese et al. (mAbs 5:2, 279-287; March/April 2013). 32 different proteins and controls were coated on two 384-well MSD standard plates at a concentration of 1.0 µg/mL at 4° C. over night. The coating solution was discarded and plates were blocked with 50 µL 3% (w/v) BSA in PBS for one hour at RT on a microtiter plate shaker (~500 rpm) followed by three washing steps with 50 µL washing buffer (PBS with 0.05% (v/v) Tween 20). IgG samples were diluted to 100 nM and 10 nM in assay buffer (PBS with 0.5% (w/v) BSA, 0.05% (v/v) Tween 20). As controls, isotype control antibody MOR03207 (IgG1f_AEASS) and assay buffer were used. Samples and controls were added at 30 µL/well and incubated for three hours at RT on a microtiter plate shaker. The plates were washed three times and 30 µL detection antibody (ECL-labeled anti-human Fab) were added per well and incubated for one hour on a microtiter plate shaker (~500 rpm). After washing the MSD plate and adding 35 µL/well MSD Read Buffer T with surfactant, electro-chemiluminescence signals were detected using a SECTOR® Imager S600 instrument (Meso Scale Diagnostics).

For evaluation, binding signals of the antibody sample to a certain protein were divided by the respective binding signals of the reference antibody MOR03207 resulting in a binding ratio (BR). The cumulative binding ratio (CBR) of all proteins except the controls (25 in total) was then calculated: CBR up to 150 indicates an IgG without detectable unspecific binding. Values above 150 indicates an IgG with increased unspecific binding compared to the reference antibody MOR03207.

Results

Results for MAB #1 and MAB #2 are summarized in FIG. 10. In sum, no critical unspecific binding was detectable to any of the tested proteins. Very low (MAB #2) and low (MAB #1) binding to bovine transferrin was observed. Binding to bovine transferrin was confirmed in an Octet® based binding assay, but no binding to rat and cynomolgus transferrin was detected (data not shown). Thus, the observed binding to bovine transferrin was regarded as non-critical.

Final Antibody Format and Safety

C5aR is expressed on various immune cells, such as leukocytes, neutrophils and lymphocytes and human IgG1 Fc-mediated depletion of such cells needs to be prevented to avoid unwanted side effects. Accordingly, the final IgG format of an anti-C5aR antibody needs to be silent in terms of its ability to induce any effector function during therapeutic intervention.

Both, MAB #1 and MAB #2 contain five amino acid substitutions in the Fc region of human IgG1f, namely L234A, L235E, G237A, A330S and P331S (hIgG1f_AEASS, numbering according EU index) to abolish antibody induced effector function. Clinical safety of this format in the context of C5aR antibody therapy has been described in the art (Wagner F et al. Annals of the Rheumatic Diseases. 2014; 73: 499. doi: 10.1136/annrheumdis-2014-eular.2156.)

The lack of ability of MAB #1 and MAB #2 to induce effector function was confirmed in various assays, such as binding studies to Fcγ receptors or C1q as well as in vitro ADCC and ADCP assays as outlined below.

Example 10: Binding of MAB #1 and MAB #2 to FcRn Receptor Using Octet®

Method

Apparent $K_D$ determination to immobilized neonatal Fc receptor (FcRn) from different species was performed at pH 6.0 and 7.2 at 27° C. using an Octet® HTX instrument (FortéBIO, Pall Life Sciences). 0.5 nm of biotinylated human, cynomolgus, mouse and rat FcRn were captured on streptavidin (SA) sensors (FortéBIO, Pall Life Sciences). Kinetic measurements were performed using 8 different concentrations of IgGs (3n serial dilution, 1000 to 0.46 nM) in Octet® buffer (PBS, 0.05%/v/v) Tween-20, 0.1% (w/v) BSA) with 240 s association time and 180 s dissociation time. After each cycle the sensor was regenerated to remove bound ligand/antibody complex (2×30 s in HBS-EP+, pH 8.0). All sensorgrams were fitted using Data Analysis Software 10.0 (FortéBIO, Pall Life Sciences) to determine the apparent affinity and the data was fitted with a steady state model.

Results

Results are summarized in Table 16. MAB #1 and MAB #2 revealed apparent binding affinities to FcRn from different species in an expected affinity range (comparable to isotype control antibody MOR03207 IgG1f and the physiological binding behavior for binding to human FcRn could be confirmed for both IgG molecules, i.e. no binding at neutral pH (7.2) was detectable. Accordingly, the introduced 5 mutations into the Fc region of the antibodies did not adversely affected human FcRn binding.

TABLE 16

Binding of MAB#1 and MAB#2 to FcRn via the Fc region at pH 6.0 and 7.2.

| Antibody | Antigen | $K_D$ [nM] pH 6.0 | $K_D$ [nM] pH 7.2 |
|---|---|---|---|
| MAB#2 | Human | 36* | no binding |
| MAB#1 | FcRn | 9.0* | no binding |
| MAB#2 | Cynomolgus | 30* | no binding |
| MAB#1 | FcRn | 6.8* | 560** |
| MAB#2 | Murine | 7.3 | 130 |
| MAB#1 | FcRn | 4.3 | 39 |
| MAB#2 | Rat | 10 | 300 |
| MAB#1 | FcRn | 5.7 | 110 |

*Deviation from fit model (pH 6.0)
**Slight binding at pH 7.2
*** Values formatted in italics are mainly intended for ranking purposes Example 11: Binding of MAB #1 and MAB #2 to Human Fcγ Receptors Using Octet®

Method $K_D$ determination via IgG capture setup was performed at 27° C. using Octet® (FortéBIO, Pall Life Sciences). 2.0 nm of IgGs diluted in Octet assay buffer (PBS, 0.05% (v/v) Tween-20, 0.1% (w/v) BSA) were captured on Protein A sensors (FortéBIO, Pall Life Sciences). Kinetic measurements were performed using 7 concentrations of Fc gamma receptors (2n serial dilution) in assay buffer. After each cycle the sensors were regenerated to remove bound ligand/antibody complex (2×30 s in 10 mM Gly/HCl, pH 1.5). All sensorgrams were fitted using Data Analysis Software 10.0, (FortéBIO, Pall Life Sciences) to determine $k_{on}$ and $k_{off}$ rate constants, which were used to calculate $K_D$. The raw data was fitted with a 1:1 binding model, with parameter $R_{max}$ set to local.

Results

Results are summarized in Table 17. No or only very weak binding of MAB #1 and MAB #2 to any of the tested Fcγ receptors could be detected and confirmed that the introduced mutations into the human IgG1 Fc region are effective in abolishing Fcγ receptor binding.

TABLE 17

Binding of MAB#1 and MAB#2 to human Fcγ receptors via Fc-region

| FcγR | MAB#2 | Mab#1 |
|---|---|---|
| hu_FcγRI | no binding | no binding |
| hu_FcγRIIa (131H) | no binding | no binding |
| hu_FcγRIIa (131R) | very slight binding only at highest antibody concentration observed | very slight binding only at highest antibody concentration observed |
| hu_FcγRIIIa (158F) | no binding | no binding |
| hu_FcγRIIIa (158V) | no binding | no binding |
| hu_FcγRIIb | no binding | no binding |

Example 12: Binding of MAB #1 and MAB #2 to C1q Using Octet®

Method

Apparent (bivalent) $K_D$ determination via IgG capture setup was performed at 27° C. using Octet® (Fortébio Pall Life Sciences). 2.0 nm of IgGs diluted in Octet® buffer were captured onto anti-hu Fab CH1 kappa/lambda (BAC) immobilised onto streptavidin (SA) sensors (FortéBIO, Pall Life Sciences). Kinetic measurements were done using 8 concentrations of C1q (3n serial dilution, 500 to 0.69 nM) in Octet® assay buffer (see above) with 240 s association time and 240 s dissociation time. After each cycle the sensors were regenerated to remove bound ligand/antibody complex (2×50 mM NaOH, 1×10 mM Gly/HCl, pH 1.5, for 30 s each). All sensorgrams were fitted using Data Analysis Software 9 (FortéBIO, Pall Life Sciences) to determine the apparent affinity. The data was fitted with a steady state model.

Results

Results are summarized in Table 18. As expected, no binding of MAB #1 and MAB #2 to C1q (isolated from pooled human plasma) was observable and confirmed that the introduced mutations into the human IgG1 Fc region are effective in abolishing C1q binding.

TABLE 18

Binding of MAB#1 and MAB#2 to human C1q.

| Antigen | MAB#2 | MAB#1 |
|---|---|---|
| Human C1q | no binding | no binding |

Example 13: ADCC and ADCP In Vitro Activity of MAB #1

Methods

ADCC and ADCP activity for MAB #1 was tested using the Promega ADCC and ADCP Reporter Bioassays according to the manufacturer's instructions (Cat #G7017 and Cat #G988A, respectively). The kits employs engineered Jurkat cells as effector cells. The cells either stably express the FcγRIIIa receptor, V158 (high affinity) variant for ADCC and FcγRIIa_H receptors for ADCP and an NFAT response element driving expression of firefly luciferase. As target cells, CHO Flp-In™ cells expressing human C5aR were used. Binding of the effector cells to the target through the antibody bridge (e.g. through MAB #1 or MAB #2) initiates a cascade of events in the NFAT pathway, resulting in the expression of the firefly luciferase protein. The enzymatic reaction produces luminescence, which is proportional to the luciferase concentration, directly correlating to ADCC or ADCP activity. ADCC or ADCP activity was analyzed for MAB #1 by plotting the average signal to background values.

Since for MAB #1, a wild-type human IgG1f version was not available, a wild-type IgG1f as well as a Fc-silent human IgG1f_AEASS version of an in-house human anti-C5aR control antibody was included as positive control. In addition, a Fc-silent (hIgG1_AEASS) and wild-type version (hIgG1f) version of the isotype control antibody MOR03207 was included as negative control.

Results

Figure 8:
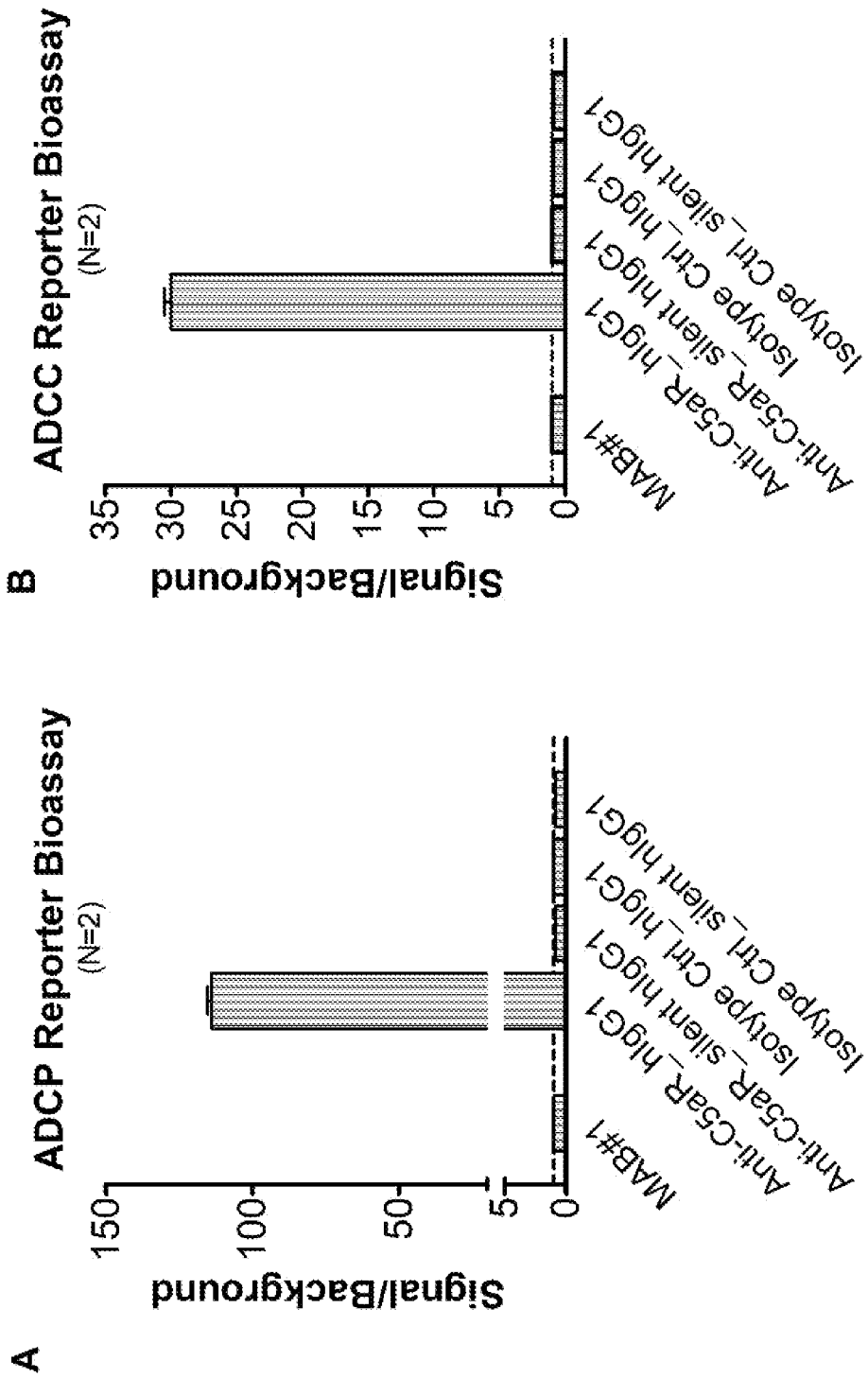
FIG. 8: Promega ADCC and ADCP reporter bioassay. Comparison of MAB #1 and a monoclonal anti-C5aR control IgG bearing either a wild-type (non-silent) human IgG1 Fc region or a variant (silent) Fc region identical to the Fc region of MAB #1. In addition, isotype control antibody MOR03207 was included with either the variant or wild-type human IgG1 Fc region. Assays were performed according to the supplier's instructions using engineered Jurkat cells either expressing FcγRIIa_H to mimic the ADCP pathway or Jurkat cells expressing the FcγRIIIa, V158 high affinity variant to mimic the ADCC pathway and C5aR expressing CHO cells. A Results from the ADCP reporter bioassay at an IgG concentration of 10 µg/ml. B Results from the ADCC reporter bioassay at an IgG concentration of 10 µg/ml. Data are provided as average fluorescence signal over background.

Results are summarized in Table 19 and depicted in FIGS. 8A (ADCP) and B (ADCC) for an IgG concentration of 10 μg/ml. MAB #1 did not induce FcγRIIIa or FcγRIIa_H activation of the NFAT pathway in engineered effector cells in the presence of C5aR overexpressing CHO cells, similar to the Fc-silent version of the anti-C5aR control antibody and the Fc-silent version of MOR03207. The wild-type (non-silent) version of the C5aR specific control antibody clearly induced luciferase production in engineered Jurkat cells in the presence of C5aR expressing CHO cells.

In sum, the experiment clearly confirmed that the introduced mutations into the wild-type human IgG1 Fc region are efficient in preventing ADCC and ADCP activity.

TABLE 19

Overview of the conducted in vitro assays to confirm that MAB#1 (hIgG1f_AEASS) does not mediate effector function.

| Criteria | Assay | Results for MAB#1 |
|---|---|---|
| No ADCC | ADCC Reporter Bioassay | No FcγRIIIa_V activation of NFAT pathway in engineered effector cells detectable |
| No ADCP | ADCP Reporter Bioassay | No FcγRIIa_H activation of NFAT pathway in engineered effector cells detectable |
| No CDC | huC1q Binding (Octet ®) | No binding to human C1q detectable |
| No binding to Fcγ Receptors | FcγR Binding (Octet ®) | No binding to the FcγRs. Highest background (close to slight binding) on hFcγRIIa_R |
| Physiological FcRn binding | FcRn Binding (Octet ®) | Physiological binding with apparent $K_D$ in the expected range |

Functional Characterization of MAB #1 and MAB #2

The neutralizing activities of MAB #1 and MAB #2 were analyzed in different in vitro assays which monitor C5a induced activation of C5aR.

As elevated levels of C5a has been described under pathophysiological conditions, the capability of a C5aR antagonistic antibody to neutralize high concentrations of C5a, which may be present locally at the disease site, is expected to provide a beneficial therapeutic effect in vivo. Accordingly, the in vitro experiments were also set-up to reflect such in vivo pathological conditions.

Example 14: PathHunter® β-Arrestin Assay (DiscoveRx)

Methods:

The PathHunter® β-Arrestin sssay from DiscoveRx was performed according to the manufacturer's instructions. In brief, human C5a induced human C5aR activity was measured by the detection of the interaction of β-arrestin with the activated C5aR using β-galactosidase enzyme fragment complementation.

β-arrestin recruitment was induced using recombinant human C5a and enzyme activity was measured using chemiluminescent detection reagents from DiscoveRx. Chinese hamster ovarian cells (CHO) cells, expressing the engineered version of human C5aR were seeded overnight and serial dilutions of human C5a (R&D Systems) were added and incubated at 37° C. and 5% CO2 for 1.5 h (generating the titration curves in absence of the antagonist). In parallel, titration curves of human C5a were determined in presence of the C5aR specific antibodies (fixed IgG conc. of 50 nM). For doing so, IgGs were added to the cells before stimulation with human C5a and incubated for 1 h at 37° C. and 5% $CO_2$. Results were expressed as relative luminescence units. Titration curves for human C5a in the presence and absence of the antagonistic IgGs were generated via GraphPad® Prism.

Figure 4:
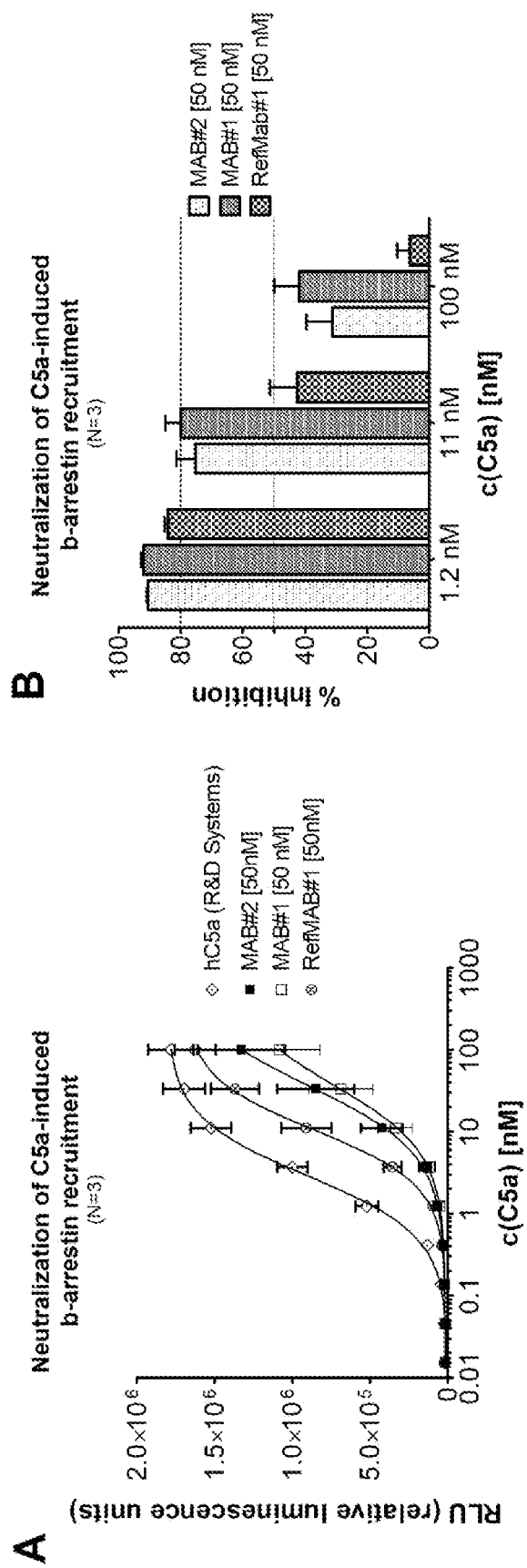
FIG. 4: PathHunter®—β-arrestin assay from DiscoveRx. Neutralization of human C5a induced β-arrestin recruitment. A Log dose-response curves for increasing concentrations of recombinant human C5a in absence or presence of MAB #1 (50 nM), MAB #2 (50 nM) and RefMAB #1 (50 nM). B Percentage inhibition was calculated for three increasing concentrations of human C5a (1.2 nM, 11 nM and 100 nM, respectively) at a final IgG concentration of 50 nM.

For the β-arrestin assay, the shifts in the dose-response curves for human C5a to higher doses (i.e. horizontally to the right on the dose axis) were compared for MAB #1, MAB #2 and RefMAB #1 (FIG. 4A). Additionally, the % inhibition at three increasing C5a concentrations (1.2 nM, 11 nM and 100 nM) was calculated and compared (FIG. 4B).

Results

The results from the β-arrestin assays are depicted in FIGS. 4A and 4B and summarized in Table 20 and Table 21. In the absence of antibody, a dose-response curve for human C5a with an average $EC_{50}$ concentration of 2.9 nM was obtained (FIG. 4A).

Adding MAB #1 or MAB #2 to human C5a at a final IgG concentration of 50 nM resulted in a significant shift in the dose-response curve of more than 12-fold to higher doses of human C5a. Being more precisely, in the presence of 50 nM MAB #1 or MAB #2, a dose-response curve for human C5a with an average $EC_{50}$ concentration of 37 nM was obtained (FIG. 4A, Table 20). In other word, the presence of MAB #1 or MAB #2 significantly reduces the ability of human C5 to induce C5aR activation or, alternatively, in the presence of MAB #1 or MAB #2, human C5a needs to be added in an at least 12-fold higher concentration in order to induce the same C5aR activity when compared to its activity in the absence of antibody.

This observation was also reflected when the % inhibition at three increasing C5a concentrations was calculated (FIG. 4B). At 1.2 nM human C5a, all three tested antibodies, MAB #1, MAB #2 and RefMAB #1, revealed a comparable inhibition of C5a induced C5aR activity of more than 80% at an IgG concentration of 50 nM. If however, an about 10-fold higher concentration of human C5a (11 nM) was used for activation of C5aR, RefMAB #1 was only able to neutralize of about 50% of C5a induced C5aR activity. This is in strong contrast to MAB #1 and MAB #2, which were still able to neutralize up to 80% of C5a induced C5aR activity.

This effect was even more pronounced when a 100-fold higher concentration of human C5a (100 nM) for activation of C5aR was used. Here, almost no neutralizing activity was detectable for RefMAB #1, whereas MAB #1 and MAB #2 were still able to neutralize of about 40% and 30%, respectively, of the human C5a induced C5aR activity.

Accordingly, both, MAB #1 and MAB #2 are efficient in neutralizing pathophysiological C5a concentrations in vitro and are significant more potent compared to RefMAB #1.

TABLE 20

In vitro β-arrestin assay (n = 3): Inhibitory activity of C5aR specific antibodies on C5a-induced C5aR activity measured by the detection of the interaction of β-arrestin with activated C5aR using β-galactosidase enzyme fragment complementation.

|  | Activity of human C5a $EC_{50}$ (nM) in absence or presence of anti-C5aR antibody | x fold reduced activity of C5a in presence of anti-C5aR antibody |
|---|---|---|
| hC5a | 2.9 | — |
| hC5a + MAB#1 (50 nM) | 37 | 12.8 |
| hC5a + MAB#2 (50 nM) | 37 | 12.8 |
| hC5a + RefMAB#1 (50 nM) | 10 | 3.4 |

TABLE 21

In vitro β-arrestin assay (n = 3): Inhibitory activity of C5aR specific antibodies on C5a-induced C5aR activity calculated for 3 concentrations of C5a and a fixed IgG concentration of 50 nM and measured by the detection of the interaction of β-arrestin with activated C5aR using β-galactosidase enzyme fragment complementation.

|  | MAB#2 | MAB#1 | RefMab#1 |
|---|---|---|---|
| [%] inhibition at 1.2 nM C5a and 50 nM IgG | 90.5 | 91.9 | 84.2 |
| [%] inhibition at 11 nM C5a and 50 nM IgG | 75.2 | 79.9 | 38.9 |
| [%] inhibition at 100 nM C5a and 50 nM IgG | 31.2 | 41.8 | 6.4 |

Example 15: Inhibition of Neutrophil and Monocyte Activation by MAB #1 and MAB #2—CD11b Assay The neutralization potency of MAB #1 and MAB #2 was furthermore determined in a functional CD11b whole blood assay representing a more physiological set up. CD11b combines with CD18 to form the integrin Mac-1 complex, which serves as a multi-ligand receptor. CD11b is constitutively expressed on the surface of >50% peripheral blood leukocytes; upon leukocyte activation, its expression is up regulated through the fusion of CD11b containing secretory granules into the cell membrane. CD11b expression is thus widely used as a marker of leukocyte activation both in vivo and in vitro.

C5a, as a potent activator of human neutrophils and monocytes, induces up-regulation of surface antigen CD11b. Thus, the ability of MAB #1 and MAB #2 to prevent C5a-induced activation of granulocytes and monocytes was investigated by assessing the CD11b levels in whole-blood derived granulocytes and monocytes. The experiments were basically performed as described in US patent application US2013/0295116 (NOVO NORDISK).

Method

In a first assays set-up, whole heparinized blood was mixed with IgG (in serial dilutions) and incubated for 20 min at 37° C., 5% $CO_2$. Human C5a was added at a standard concentration of 15 nM and incubated for 20 min at 37° C., 5% $CO_2$. Anti-CD11b-PE or isotype control antibody MOR03207 was added and the plate was incubated for 20 min. at 37° C., 5% $CO_2$. Finally, a red blood cell lysing buffer was added and incubated at room temperature for 15 min in the dark, the cells were washed and again resuspended in lysing buffer.

In a second experimental set-up, human C5a was added at a more clinical relevant pathophysiological concentration of 150 nM without modifying the remaining assays set-up as described above.

To investigate the receptor residence time of MAB #1, the assay was further adapted by prolonging the incubating time of the heparinized whole blood with IgG from 20 min to 300 min.

Fluorescence was measured using the FACS Array or Novocyte device. Samples were gated to exclude dead cells and debris. Monocytes and granulocytes were identified according to their FSC and SSC profiles and gated. The median fluorescence intensity (MFI) of the gated granulocytes and/or monocytes in the CD11b-PE channel (Yellow-A) was calculated. Results were expressed as a percentage of inhibition (% Inhibition). Maximum CD11b expression ($MFI_{Max}$) was the average MFI of the cells incubated with C5a but without IgG. The minimum (background) CD11b expression ($MFI_{Min}$) was the average MFI of the cells incubated without C5a and without IgG. The formula used to calculate % inhibition for each samples was:

$$\% \text{ Inhibition} = 100 - (((MFI_{Sample} - MFI_{Min}))/((MFI_{Max} - MFI_{Min})) \times 100)$$

Data was evaluated using FlowJo™, entered into GraphPad® Prism (v4.0) and fitted to the sigmoidal dose-response curve using non-linear regression to calculate the $IC_{50}$.

Results for MAB #1 Using 15 nM C5a Ligand

Results for MAB #1 from the CD11b whole blood assays are summarized in Table 22. For both gated cell populations (monocytes and granulocytes), $IC_{50}$ values in the single-digit nM range were determined with maximum inhibition of almost 88% for granulocytes and 83% for monocytes.

TABLE 22

Ability of MAB#1 to prevent C5a-mediated activation of granulocytes and monocytes. Overview maximum inhibition and $IC_{50}$ values was determined in the CD11b assay using 15 nM C5a (n = 3).

| Cell type | MAB#1 - Inhibition of CD11b expression | |
| --- | --- | --- |
| CD11b Granulocytes | max % inhibition (at 600 nM IgG) | 87.2 ± 1.7 (N = 3) |
| | $IC_{50}$ (nM) | 9.8 ± 0.6 (N = 3) |
| CD11b Monocytes | max % inhibition (at 600 nM IgG) | 83.3 ± 3.6 (N = 3) |
| | $IC_{50}$ (nM) | 4.2 ± 0.8 (N = 3) |

Results for MAB #1, MAB #2 and RefMAB #1 Using 15 nM vs. 150 nM C5a Ligand

Besides adding 15 nM of human C5a for stimulation of granulocytes (as described above), a ten-fold higher concentration (150 nM) of ligand was used to simulate a more pathophysiological ligand concentration.

Again, MAB #1, MAB #2 and RefMAB #1 were dose-titrated and inhibition curves were generated using GraphPad® Prism via the nonlinear regression function. The results are quantitatively expressed as "concentration of antagonist needed in order to induce 50% of inhibition".

Figure 5:
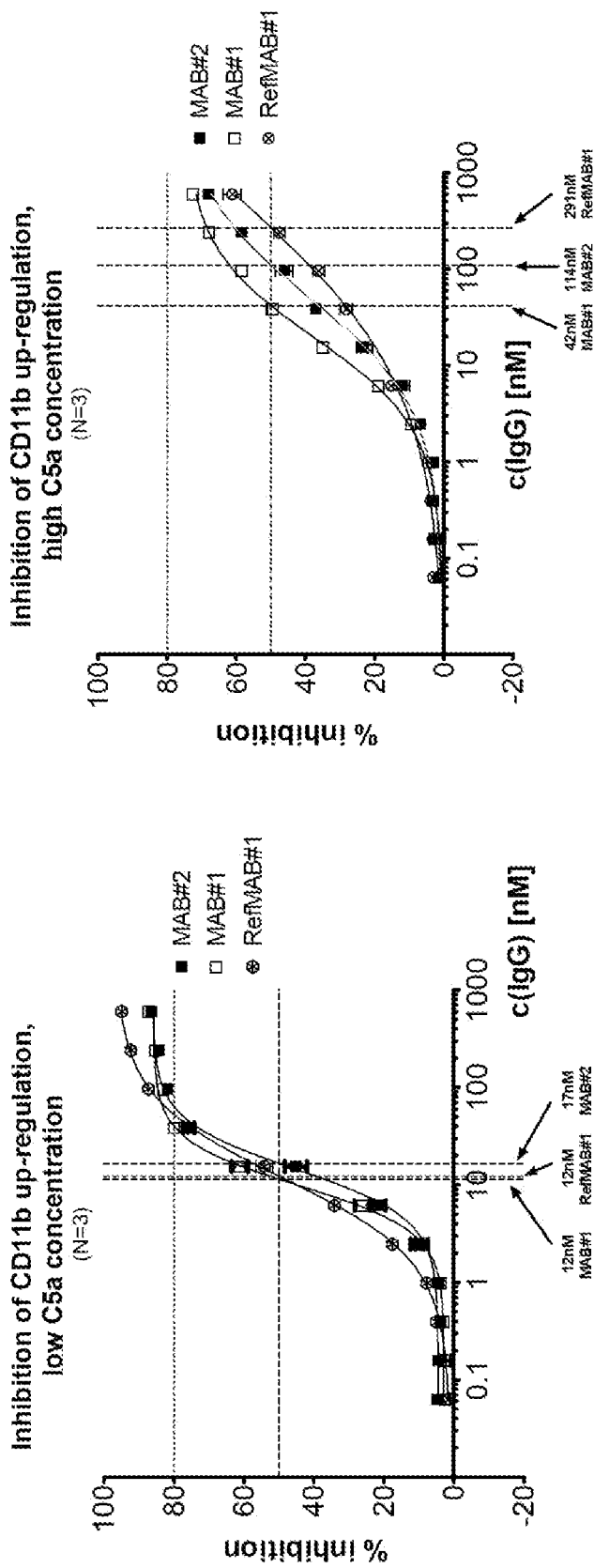

The results from this CD11b whole blood assay are shown in FIGS. 5A and B.

FIG. 5A depicts the neutralizing activity of MAB #1, MAB #2 and RefMAB #1 at 15 nM C5a and FIG. 5B depicts the respective neutralizing activity at 150 nM C5a. As a quantitative read-out, the IgG concentration for reaching 50% inhibition of CD11b upregulation was calculated and the results are indicated below the x-axis in both Figures.

Overall, similar observations as for the β-arrestin assay (Example 14) were made when using increasing C5a concentrations in the CD11b whole blood assay gated on granulocytes as primary target cells. In order to block the effects of 15 nM human C5a to 50%, an IgG concentration of 12 nM for MAB #1 and RefMAB #1 was needed, whereas for MAB #2 an IgG concentration of 17 nM was sufficient. However, in order to block 50% of CD11b upregulation induced by a 10 fold higher C5a concentration (150 nM) significant different amounts of the antagonists were required. While for MAB #1, an IgG concentration of 42 nM were now sufficient to inhibit 50% of the C5a induced activation of C5aR, a 7-fold higher concentration of RefMAB #1 (291 nM) was required to reach the same blocking effect. For MAB #2 an IgG concentration of 114 nM was sufficient.

Accordingly, the same ranking of the 3 IgGs in terms of potency as already seen in the β-arrestin assay (MAB #1>MAB #2>RefMAB #1) could be done and both, MAB #1 and MAB #2 appeared very efficient in neutralizing pathophysiological C5a concentrations in vitro and were significant more potent compared to RefMAB #1.

Results for MAB #1—Influence on Receptor Residence Time

Seow and colleagues (Seow V et al., Sci Rep. 2016; 6: 24575) reported that the generation of C5a is localized at the cell membrane and can be profoundly high for brief but repeated periods. Therefore, it was suggested that an antagonist of C5aR with long residence time could be advantageous in systems with rapid and transient signaling. It was also concluded that an increased receptor residence time measured in vitro could also translate to the duration of action and degree of efficacy in vivo.

To compare the receptor residence time of the two antibodies in a similar set up as published by Seow and co-workers, log dose inhibition curves for 20 minutes and 300 minutes of IgG incubation with granulocytes and monocytes present in whole blood was evaluated as described above.

The results from this experimental set-up of the CD11b whole blood assay are shown in FIG. 6A-D. Surprisingly, a significant increase in the neutralizing activity over a prolonged period of incubation time was observable of MAB #1. As shown in FIGS. 6A and C, for both, granulocytes and monocytes populations, the calculated $IC_{50}$ concentration for MAB #1 decreased over time of about 6-fold ($IC_{50}$ values are summarized in Table 23). For RefMAB #1, no shift or decrease in the inhibition curves was observable after 300 minutes (FIGS. 6B and D).

TABLE 23

CD11b assay after 20 minutes or 300 minutes of IgG incubation with whole-blood at 15 nM C5a. Provided are IC$_{50}$ values and x-fold potency improvements (20 min. vs 300 min.) for granulocytes (upper panel) and monocytes (lower panel)

|  | MAB#1 | | RefMAB#1 | |
| --- | --- | --- | --- | --- |
|  | IC50 (in nM) | x-fold improvement | IC50 (in nM) | x-fold improvement |
| CD11b Granulocytes | | | | |
| 20 minutes | 11.0 ± 1.0 (N = 2) | 4.8 | 10.2 ± 1.9 (N = 2) | 1.6 |
| 300 minutes | 2.3 ± 0.0 (N = 2) |  | 6.5 ± 0.5 (N = 2) |  |
| CD11b Monocytes | | | | |
| 20 minutes | 4.0 ± 1.0 (N = 2) | 5.7 | 1.8 ± 0.5 (N = 2) | 0.3 |
| 300 minutes | 0.7 ± 0.2 (N = 2) |  | 5.3 ± 1.0 (N = 2) |  |

In sum, the combination of both, efficient neutralization of pathophysiological C5a levels and an increased potency over time is expected to be beneficial in vivo.

Example 16: C5a Induced Migration of Neutrophils

C5a induced chemotaxis of purified neutrophils was analyzed. The experiment was basically performed as described in US patent application US2013/0295116.
Methods
Neutrophils were isolated and purified from whole blood of three different human donors using the MACSxpress® Whole Blood Neutrophil Isolation Kit, human (Miltenyi Biotec Cat #130-104-434 and the MACSxpress® Erythrocyte Depletion Kit, human (Miltenyi Biotec, CAT #130-098-196).

The potency of the IgGs to inhibit hC5a dependent neutrophil migration was analyzed by the Boyden chamber technique using FluoroBlok® 3.0 μM pore size 96-well plates. The membrane of the Boyden chamber pore was coated with 1 mg/mL human fibrinogen for 2 hrs at 37° C. After washing, the membranes were blocked with a solution containing 2% bovine serum albumin (BSA) for 1 hr at 37° C. Purified neutrophils were then stained with calcein and $10^5$ stained cells added to the upper compartment in the Boyden chamber with and without the antagonistic IgGs (100 and 600 nM). hC5a (R&D Systems, 10 nM) was applied to the lower compartment in the Boyden chamber. The plate was measured at 485/538 nm at 37° C. every 5 min for 60 min in a plate reader (Tecan M1000Pro). The ability of neutrophils to migrate to the lower chamber is determined measuring the calcein-stained neutrophils passing through the fluoroblok membrane. The results are expressed as kinetic migration curves (5-60 min) as well as percentage inhibition calculated at selected time points (15, 25 and 35 min).
The formula used to calculate % inhibition was % Inhibition=100−(((RFU$_{Sample}$−RFU$_{Min}$))/((RFU$_{Max}$−RFU$_{Min}$))×100)

Results
The average percentage inhibition of neutrophil migration at selected time points at two tested IgG concentrations was calculated from 3 independent experiments using neutrophils from three different human donors.

Figure 7:
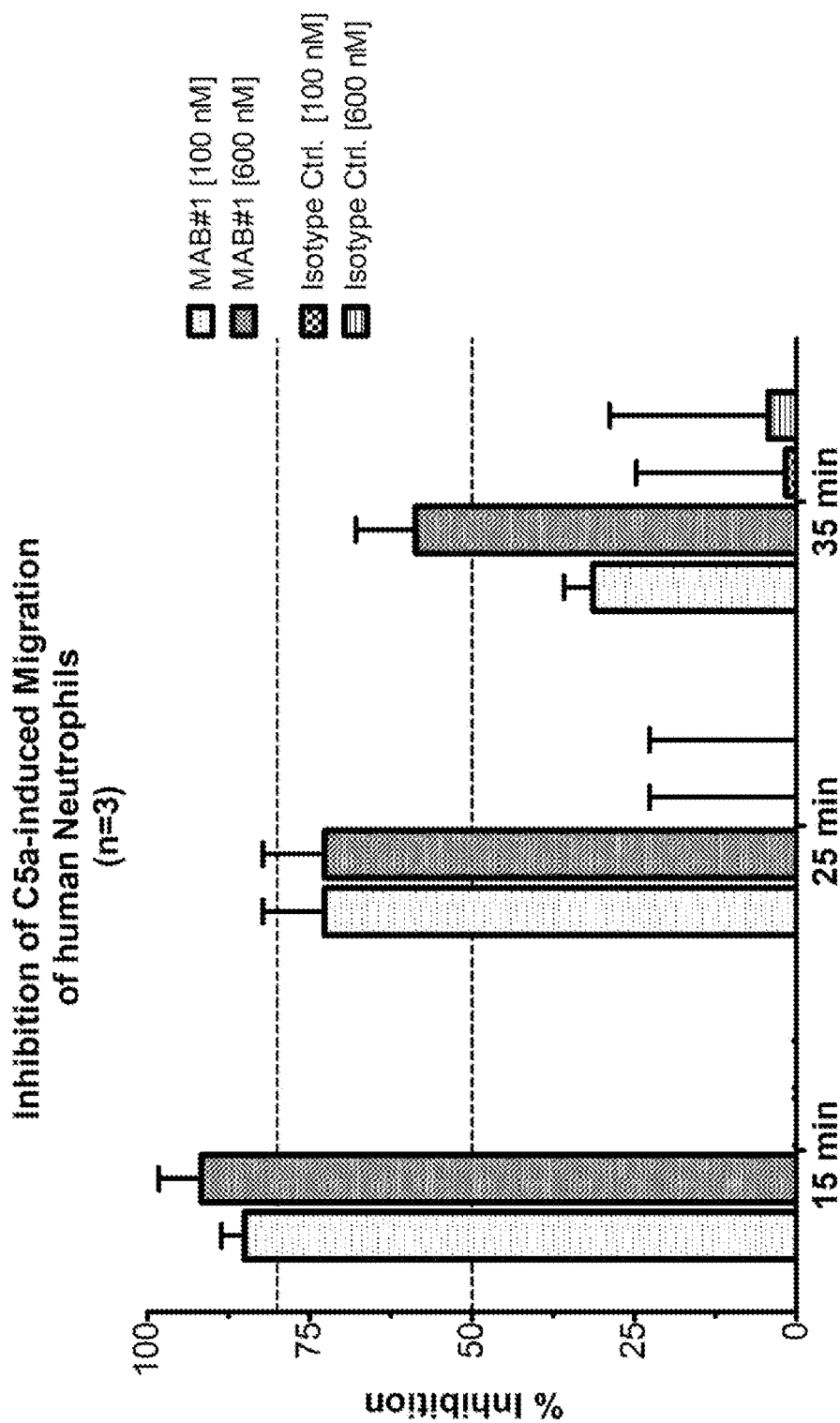
FIG. 7: Inhibition of human C5a induced human neutrophil migration. MAB #1 and negative control MOR03207 were each tested at two IgG concentration (100 nM and 600 nM, respectively) in the presence of 10 nM human C5a. Average values from three independent assay runs at 3 different time points (15 min., 25 min., 35 min.) are shown. Neutrophils were obtained from 3 different human donors. Percentage inhibition was calculated on the basis of neutrophil migration in the absence of antibody.

As depicted in FIG. 7, after 15 min of migration, almost complete inhibition of C5a-induced neutrophil migration was reached for MAB #1. After 35 min of migration and the highest IgG concentration tested (600 nM), MAB #1 still revealed >50% inhibition. The negative isotype control antibody MOR03207 showed no inhibitory effect on neutrophil migration.

Example 17: C5a Induced Release of Cytokines by Macrophages

Figure 11:
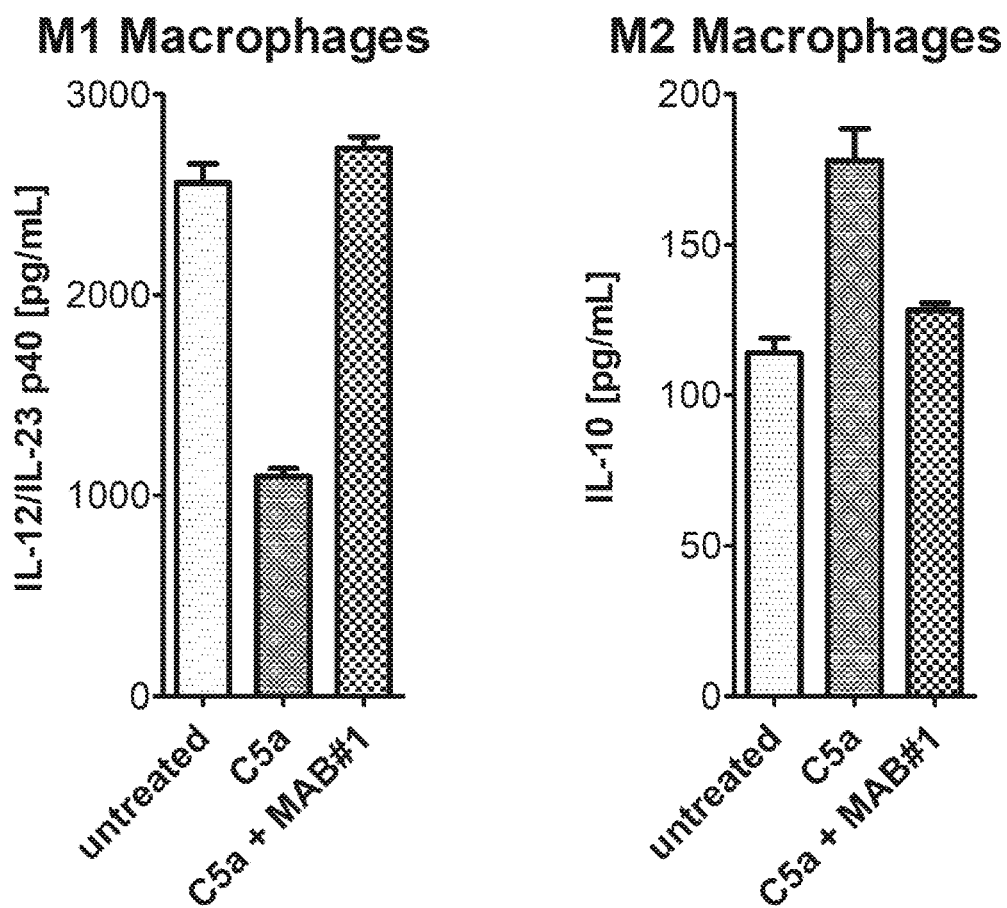
FIG. 11: Cytokine release by monocyte-derived in vitro-matured M1 and M2 macrophages. IL-10 and IL-12 levels were determined by ELISA after treatment with MAB #1 and incubation with C5a overnight.

Macrophages release pro- or anti-inflammatory cytokines upon activation depending on their polarization. Hence, it was evaluated whether blockade of the C5a/C5aR interaction with MAB #1 affects the C5a-induced release of cytokines by M1 and M2 macrophages. A cytokine ELISA was performed to detect the production of anti-inflammatory IL-10 by M2 macrophages and pro-inflammatory IL-12 by M1 macrophages.
Methods
Briefly, peripheral blood mononuclear cells (PBMCs) were prepared from whole blood of healthy human donors by density-gradient centrifugation with Biocoll® separating solution and SepMate™ tubes (Stemcell). Monocytes were isolated from PBMCs using a CD14+ selection kit (Miltenyi Biotech) and cultured in RPMI supplemented with 10% FCS and 1×GlutaMax™ in 96 well plates. Overnight-plated monocytes were polarized for 24 hours at 37° C. to M1 macrophages using LPS (20 ng/ml) and IFNγ (50 ng/ml) and pre-incubated with MAB #1 (30 nM) for 30 minutes followed by addition of C5a (15 nM) for another 24 hours. M1 macrophages stimulated with C5a in absence of MAB #1 and untreated controls were included. After 24 hours, cell supernatants were analyzed by an IL-12/IL23 DuoSet® ELISA (R&D Systems) according to manufacturer's instructions. For generation of M2 macrophages, monocytes were pre-differentiated into macrophages by culture for 5 days in RPMI/10% FCS supplemented with M-CSF and addition of M-CSF, IL-4, IL-13 and IL-6 (40 ng/ml each) at day 5. C5a (15 nM)+/−MAB #1 (30 nM) were added daily from day 5 until 9. On day 9, cell supernatants were analyzed by an IL-10 DuoSet® ELISA (R&D Systems) according to manufacturer's instructions.
Results
While incubation with C5a lead to decreased IL-12 production of M1 macrophages, no reduction in IL-12 levels could be observed after pre-treatment with MAB #1 in comparison to the untreated control. On the other hand, treatment with MAB #1 inhibited C5a-induced IL-10 production in M2 macrophages (see FIG. 11)

In conclusion, MAB #1 efficiently inhibited C5a-induced production of anti-inflammatory IL-10 by M2 macrophages and restored the production of pro-inflammatory IL-12 by M1 macrophages thereby demonstrating the mode of action of MAB #1 in vitro.
Pharmacokinetics Example 18: Pharmacokinetics The pharmacokinetic profile of MAB #1 was assessed in male Han-Wistar rats (n=3 animals) after a single intravenous (i.v.) administration of 10 mg/kg IgG.
Methods
Plasma samples were collected from each animal via retro-orbital sinus or mandibular vein puncture at the following time-points: Predose, 0.083, 1, 3, 8, 24, 48, 72, 96, 168, 240, 336 and 504 hours post administration.

Free, bioactive MAB #1 concentrations in rat plasma were determined using a MSD-based ligand-binding assay. Briefly, a biotinylated N-terminal human C5aR peptide was coated on the surface of a 96-well Streptavidin-MSD plate. The bound analyte was detected using a drug-specific anti-idiotypic ECL-labelled antibody. Pharmacokinetic properties of MAB #1 were evaluated using non-compartmental data analysis (NCA) based on free drug concentrations in plasma.

Results

Figure 9:
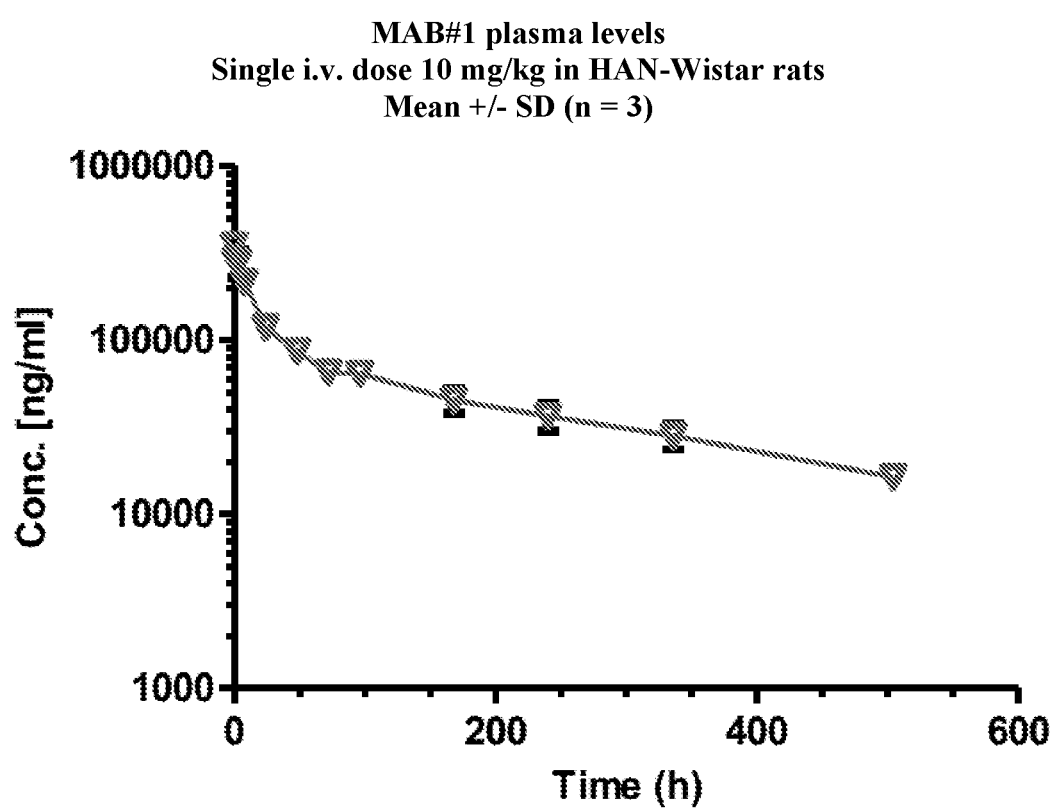
FIG. 9: Group mean pharmacokinetic profile of MAB #1 in Han Wistar rats following a single intravenous administration of 10 mg/kg IgG. Data are provided as mean values (IgG concentration over time)±standard deviation (S) (n=3).

The mean plasma concentrations over time is depicted in FIG. 9. The mean maximum plasma concentrations of MAB #1 after a single i.v. administration were observed at 5 minutes (i.e. 0.083 hours) after administration ($T_{max}$) in all three animals (i.e. first sampling time point post administration). The mean volume of distribution (Vz) of 106 mL/kg was between plasma volume and extracellular volume (Davies et al., 1993). The mean terminal elimination half-life following i.v. administration was determined at 9.0 days, the mean total clearance was determined at 0.341 mL/h/kg.

Overall, MAB #1 demonstrated a typical pharmacokinetic profile of a human IgG1 antibody in rat plasma with no cross-reactivity to the rodent C5aR. No signs of anti-drug-antibody (ADA)-mediated clearance could be detected.

We claim:

1. An isolated antibody or antigen-binding fragment thereof specific for human Complement C5a Receptor (C5aR), comprising:
a heavy chain complementarity determining region 1 (HCDR1) comprising the amino acid sequence of SEQ ID NO: 27, an HCDR2 comprising the amino acid sequence of SEQ ID NO: 28, an HCDR3 comprising the amino acid sequence of SEQ ID NO: 29, a light chain complementarity determining region 1 (LCDR1) comprising the amino acid sequence of SEQ ID NO: 32, an LCDR2 comprising the amino acid sequence of SEQ ID NO: 33, and an LCDR3 comprising the amino acid sequence of SEQ ID NO: 34.

2. The isolated antibody or antigen-binding fragment of claim 1, comprising:
a variable heavy chain region (VH) comprising an amino acid sequence having at least 80% identity to the amino acid sequence of SEQ ID NO: 35 and a variable light chain region (VL) comprising an amino acid sequence having at least 80% identity to the amino acid sequence of SEQ ID NO: 36.

3. The isolated antibody or antigen-binding fragment thereof of claim 1, comprising:
a VH comprising an amino acid sequence having at least 85% identity to the amino acid sequence of SEQ ID NO: 35 and a VL comprising an amino acid sequence having at least 85% identity to the amino acid sequence of SEQ ID NO: 36.

4. The isolated antibody or antigen-binding fragment thereof of claim 1, comprising:
a VH comprising an amino acid sequence having at least 90% identity to the amino acid sequence of SEQ ID NO: 35 and a VL comprising an amino acid sequence having at least 90% identity to the amino acid sequence of SEQ ID NO: 36.

5. The isolated antibody or antigen-binding fragment thereof of claim 1, comprising:
a VH comprising an amino acid sequence having at least 95% identity to the amino acid sequence of SEQ ID NO: 35 and a VL comprising an amino acid sequence having at least 95% identity to the amino acid sequence of SEQ ID NO: 36.

6. The isolated antibody or antigen-binding fragment thereof of claim 1, comprising:
a VH comprising the amino acid sequence of SEQ ID NO: 35 and a VL comprising the amino acid sequence of SEQ ID NO: 36.

7. The isolated antibody or antigen-binding fragment thereof of claim 1, comprising:
a heavy chain (HC) comprising an amino acid sequence having at least 80% identity to the amino acid sequence of SEQ ID NO: 37 and a light chain (LC) comprising an amino acid sequence having at least 80% identity to the amino acid sequence of SEQ ID NO: 38.

8. The isolated antibody or antigen-binding fragment thereof of claim 1, comprising:
a HC comprising an amino acid sequence having at least 85% identity to the amino acid sequence of SEQ ID NO: 37 and a LC comprising an amino acid sequence having at least 85% identity to the amino acid sequence of SEQ ID NO: 38.

9. The isolated antibody or antigen-binding fragment thereof of claim 1, comprising:
a HC comprising an amino acid sequence having at least 90% identity to the amino acid sequence of SEQ ID NO: 37 and a LC comprising an amino acid sequence having at least 90% identity to the amino acid sequence of SEQ ID NO: 38.

10. The isolated antibody or antigen-binding fragment thereof of claim 1, comprising:
a HC comprising an amino acid sequence having at least 95% identity to the amino acid sequence of SEQ ID NO: 37 and a LC comprising an amino acid sequence having at least 95% identity to the amino acid sequence of SEQ ID NO: 38.

11. The isolated antibody or antigen-binding fragment thereof of claim 1, comprising:
a HC comprising the amino acid sequence of SEQ ID NO: 37 and a LC comprising the amino acid sequence of SEQ ID NO: 38.

12. The isolated antibody or antigen-binding fragment thereof of claim 1, wherein the antibody or antigen-binding fragment thereof consists of:
a HC comprising an amino acid sequence of SEQ ID NO: 37 and a LC comprising an amino acid sequence of SEQ ID NO: 38.

13. The isolated antibody or antigen-binding fragment thereof of claim 1, wherein the antibody or antigen-binding fragment thereof has a human IgG1 isotype.

14. The isolated antibody or antigen-binding fragment thereof of claim 1, comprising a variant Fc region comprising one or more amino acid substitutions selected from the group consisting of L234A, L235E, G237A, A330S, and P331S, wherein amino acid numbering is according to EU index.

15. The isolated antibody or antigen-binding fragment thereof of claim 1, wherein the antibody or antigen-binding fragment thereof does not substantially induce an effector function in vitro.

16. The isolated antibody or antigen-binding fragment thereof of claim 1, wherein the antibody or antigen-binding fragment thereof is specific for human C5aR and cynomolgus monkey C5aR.

17. The isolated antibody or antigen-binding fragment thereof of claim 1, wherein the antibody or antigen-binding fragment thereof is monoclonal.

18. The isolated antibody or antigen-binding fragment thereof of claim 1, wherein the antibody or antigen-binding fragment thereof is human, humanized, or chimeric.

19. A pharmaceutical composition comprising the isolated antibody or antigen-binding fragment thereof of claim 1 and a pharmaceutically acceptable carrier.

20. The isolated antibody or antigen-binding fragment thereof of claim 1, comprising a VH consisting of the amino acid sequence of SEQ ID NO: 35 and a VL consisting of the amino acid sequence of SEQ ID NO: 36.

21. The isolated antibody or antigen-binding fragment thereof of claim 1, comprising a variant Fc region comprising amino acid substitutions L234A, L235E, G237A, A330S, and P331S, wherein amino acid numbering is according to EU index.

22. A pharmaceutical composition comprising the isolated antibody or antigen-binding fragment thereof of claim 2 and a pharmaceutically acceptable carrier.

23. A pharmaceutical composition comprising the isolated antibody or antigen-binding fragment thereof of claim 3 and a pharmaceutically acceptable carrier.

24. A pharmaceutical composition comprising the isolated antibody or antigen-binding fragment thereof of claim 4 and a pharmaceutically acceptable carrier.

25. A pharmaceutical composition comprising the isolated antibody or antigen-binding fragment thereof of claim 5 and a pharmaceutically acceptable carrier.

26. A pharmaceutical composition comprising the isolated antibody or antigen-binding fragment thereof of claim 6 and a pharmaceutically acceptable carrier.

27. A pharmaceutical composition comprising the isolated antibody or antigen-binding fragment thereof of claim 7 and a pharmaceutically acceptable carrier.

28. A pharmaceutical composition comprising the isolated antibody or antigen-binding fragment thereof of claim 8 and a pharmaceutically acceptable carrier.

29. A pharmaceutical composition comprising the isolated antibody or antigen-binding fragment thereof of claim 9 and a pharmaceutically acceptable carrier.

30. A pharmaceutical composition comprising the isolated antibody or antigen-binding fragment thereof of claim 20 and a pharmaceutically acceptable carrier.

* * * * *

```
                              SEQUENCE LISTING

Sequence total quantity: 96
SEQ ID NO: 1            moltype = AA  length = 350
FEATURE                 Location/Qualifiers
source                  1..350
                        mol_type = protein
                        organism = Homo sapiens
SEQUENCE: 1
MDSFNYTTPD YGHYDDKDTL DLNTPVDKTS NTLRVPDILA LVIFAVVFLV GVLGNALVVW   60
VTAFEAKRTI NAIWFLNLAV ADFLSCLALP ILFTSIVQHH HWPFGGAACS ILPSLILLNM  120
YASILLLATI SADRFLLVFK PIWCQNFRGA GLAWIACAVA WGLALLLTIP SFLYRVVREE  180
YFPPKVLCGV DYSHDKRRER AVAIVRLVLG FLWPLLTLTI CYTFILLRTW SRRATRSTKT  240
LKVVVAVVAS FFIFWLPYQV TGIMMSFLEP SSPTFLLLKK LDSLCVSFAY INCCINPIIY  300
VVAGQGFQGR LRKSLPSLLR NVLTEESVVR ESKSFTRSTV DTMAQKTQAV            350

SEQ ID NO: 2            moltype = AA  length = 350
FEATURE                 Location/Qualifiers
source                  1..350
                        mol_type = protein
                        organism = Homo sapiens
SEQUENCE: 2
MNSFNYTTPD YGHYDDKDTL DLNTPVDKTS NTLRVPDILA LVIFAVVFLV GVLGNALVVW   60
VTAFEAKRTI NAIWFLNLAV ADFLSCLALP ILFTSIVQHH HWPFGGAACS ILPSLILLNM  120
YASILLLATI SADRFLLVFK PIWCQNFRGA GLAWIACAVA WGLALLLTIP SFLYRVVREE  180
YFPPKVLCGV DYSHDKRRER AVAIVRLVLG FLWPLLTLTI CYTFILLRTW SRRATRSTKT  240
LKVVVAVVAS FFIFWLPYQV TGIMMSFLEP SSPTFLLLNK LDSLCVSFAY INCCINPIIY  300
VVAGQGFQGR LRKSLPSLLR NVLTEESVVR ESKSFTRSTV DTMAQKTQAV            350

SEQ ID NO: 3            moltype = AA  length = 350
FEATURE                 Location/Qualifiers
source                  1..350
                        mol_type = protein
                        organism = Macaca fascicularis
SEQUENCE: 3
MDPFSSTTLD YEHYDGKNVL DSDTPVDKTS NTLRVPDILA LVVFAVVFLV GVLGNALVVW   60
VTAFEVKRTI NAIWFLNLAV ADFLSCLALP ILFTSIVQHH HWPFGGTACR ILPSLILLNM  120
YASILLLATI SADRFLLVFN PIWCQNFRGA GLAWIACAVA WGLALLLTIP SFLYRAVRQE  180
EYSPKVLCGV DYNNDTRRER AVAIVRLVLG FLWPLLTLMI CYTFILLRTW SRRATRSTKT  240
LKVVVAVVAS FFIFWLPYQV TGTMMSFLRP SSPTYLQLKK LDSLSISFAY INCCINPVIY  300
VVAGQGFQGR LRKSLPSLLR NVLTEESVVR ESKSFTRSTV DTMTEKTQAV            350

SEQ ID NO: 4            moltype = AA  length = 351
FEATURE                 Location/Qualifiers
source                  1..351
                        mol_type = protein
                        organism = Mus musculus
SEQUENCE: 4
MDPIDNSSFE INYDHYGTMA PNIPADGIHL PKRQPGDVAA LIIYSVVFLV GVPGNALVVW   60
VTAFEARRAV NAIWFLNLAV ADLLSCLALP VLFTTVLNHN YWYFDATACI VLPSLILLNM  120
YASILLLATI SADRFLLVFK PIWCQKVRGT GLAWMACGVA WVLALLLTIP SFVYREAYKD  180
FYSEHTVCGI NYGGGSFPKE KAVAILRLMV GFVLPLLTLN ICYTFLLLRT WSRKATRSTK  240
TLKVVMAVVI CFFIFWLPYQ VTGVMIAWLP SSPTLKRVE  KLNSLCVSLA YINCCVNPII  300
YVMAGQGFHG RLLRSLPSII RNALSEDSVG RDSKTFTPST TDTSTRKSQA V          351

SEQ ID NO: 5            moltype = AA  length = 352
FEATURE                 Location/Qualifiers
source                  1..352
                        mol_type = protein
                        organism = Rattus norvegicus
SEQUENCE: 5
MDPISNDSSE ITYDYSDGTP NPDMPADGVY IPKMEPGDIA ALIIYLAVFL VGVTGNALVV   60
WVTAFEAKRT VNAIWFLNLA VADLLSCLAL PILFTSIVKN NHWPFGDQAC IVLPSLILLN  120
MYSSILLLAT ISADRFLLVF KPIWCQKFRR PGLAWMACGV TWVLALLLTI PSFVFRRIHK  180
```

```
DPYSDSILCN IDYSKGPFFI EKAIAILRLM VGFVLPLLTL NICYTFLLIR TWSRKATRST    240
KTLKVVMAVV TCFFVFWLPY QVTGVILAWL PRSSSTFQSV ERLNSLCVSL AYINCCVNPI    300
IYVMAGQGFH GRLRRSLPSI IRNVLSEDSL GRDSKSFTRS TMDTSTQKSQ AV            352

SEQ ID NO: 6              moltype = AA   length = 74
FEATURE                   Location/Qualifiers
source                    1..74
                          mol_type = protein
                          organism = Homo sapiens
SEQUENCE: 6
TLQKKIEEIA AKYKHSVVKK CCYDGACVNN DETCEQRAAR ISLGPRCIKA FTECCVVASQ     60
LRANISHKDM QLGR                                                       74

SEQ ID NO: 7              moltype = AA   length = 337
FEATURE                   Location/Qualifiers
source                    1..337
                          mol_type = protein
                          organism = Homo sapiens
SEQUENCE: 7
MGNDSVSYEY GDYSDLSDRP VDCLDGACLA IDPLRVAPLP LYAAIFLVGV PGNAMVAWVA     60
GKVARRRVGA TWLLHLAVAD LLCCLSLPIL AVPIARGGHW PYGAVGCRAL PSIILLTMYA    120
SVLLLAALSA DLCFLALGPA WWSTVQRACG VQVACGAAWT LALLLTVPSA IYRRLHQEHF    180
PARLQCVVDY GGSSSTENAV TAIRFLFGFL GPLVAVASCH SALLCWAARR CRPLGTAIVV    240
GFFVCWAPYH LLGLVLTVAA PNSALLARAL RAEPLIVGLA LAHSCLNPML FLYFGRAQLR    300
RSLPAACHWA LRESQGQDES VDSKKSTSHD LVSEMEV                             337

SEQ ID NO: 8              moltype = AA   length = 482
FEATURE                   Location/Qualifiers
source                    1..482
                          mol_type = protein
                          organism = Homo sapiens
SEQUENCE: 8
MASFSAETNS TDLLSQPWNE PPVILSMVIL SLTFLLGLPG NGLVLWVAGL KMQRTVNTIW     60
FLHLTLADLL CCLSLPFSLA HLALQGQWPY GRFLCKLIPS IIVLNMFASV FLLTAISLDR    120
CLVVFKPIWC QNHRNVGMAC SICGCIWVVA CVMCIPVFVY REIFTTDNHN RCGYKFGLSS    180
SLDYPDFYGD PLENRSLENI VQPPGEMNDR LDPSSFQTND HPWTVPTVFQ PQTFQRPSAD    240
SLPRGSARLT SQNLYSNVFK PADVVSPKIP SGFPIEDHET SPLDNSDAFL STHLKLFPSA    300
SSNSFYESEL PQGFQDYYNL GQFTDDDQVP TPLVAITITR LVVGFLLPSV IMIACYSFIV    360
FRMQRGRFAK SQSKTFRVAV VVVAVFLVCW TPYHIFGVLS LLTDPETPLG KTLMSWDHVC    420
IALASANSCF NPFLYALLGK DFRKKARQSI QGILEAAFSE ELTRSTHCPS NNVISERNST    480
TV                                                                  482

SEQ ID NO: 9              moltype = AA   length = 350
FEATURE                   Location/Qualifiers
source                    1..350
                          mol_type = protein
                          organism = Homo sapiens
SEQUENCE: 9
METNSSLPTN ISGGTPAVSA GYLFLDIITY LVFAVTFVLG VLGNGLVIWV AGFRMTHTVT     60
TISYLNLAVA DFCFTSTLPF FMVRKAMGGH WPFGWFLCKF LFTIVDINLF GSVFLIALIA    120
LDRCVCVLHP VWTQNHRTVS LAKKVIIGPW VMALLLTPV IIRVTTVPGK TGTVACTFNF    180
SPWTNDPKER INVAVAMLTV RGIIRFIIGF SAPMSIVAVS YGLIATKIHK QGLIKSSPPL    240
RVLSFVAAAF FLCWSPYQVV ALIATVRIRE LLQGMYKEIG IAVDVTSALA FFNSCLNPML    300
YVFMGQDFRE RLIHALPASL ERALTEDSTQ TSDTATNSTL PSAEVALQAK               350

SEQ ID NO: 10             moltype = AA   length = 373
FEATURE                   Location/Qualifiers
source                    1..373
                          mol_type = protein
                          organism = Homo sapiens
SEQUENCE: 10
MRMEDEDYNT SISYGDEYPD YLDSIVVLED LSPLEARVTR IFLVVVYSIV CFLGILGNGL     60
VIIATFKMK KTVNMVWFLN LAVADFLFNV FLPIHITYAA MDYHWVFGTA MCKISNFLLI    120
HNMFTSVFLL TIISSDRCIS VLLPVWSQNH RSVRLAYMAC MVIWVLAFFL SSPSLVFRDT    180
ANLHGKISCF NNFSLSTPGS SSWPTHSQMD PVGYSRHMVV TVTRFLCGFL VPVLIITACY    240
LTIVCKLHRN RLAKTKKPFK IIVTIIITFF LCWCPYHTLN LLELHHTAMP GSVFSLGLPL    300
ATALAIANSC MNPILYVFMG QDFKKFKVAL FSRLVNALSE DTGHSSYPSH RSFTKMSSMN    360
ERTSMNERET GML                                                       373

SEQ ID NO: 11             moltype = AA   length = 216
FEATURE                   Location/Qualifiers
source                    1..216
                          mol_type = protein
                          organism = Homo sapiens
SEQUENCE: 11
PELLGGPSVF LFPPKPKDTL MISRTPEVTC VVVDVSHEDP EVKFNWYVDG VEVHNAKTKP     60
REEQYNSTYR VVSVLTVLHQ DWLNGKEYKC KVSNKALPAP IEKTISKAKG QPREPQVYTL    120
PPSREEMTKN QVSLTCLVKG FYPSDIAVEW ESNGQPENNY KTTPPVLDSD GSFFLYSKLT    180
VDKSRWQQGN VFSCSVMHEA LHNHYTQKSL SLSPGK                              216
```

```
SEQ ID NO: 12            moltype = AA  length = 31
FEATURE                  Location/Qualifiers
source                   1..31
                         mol_type = protein
                         organism = Homo sapiens
SEQUENCE: 12
MDSFNYTTPD YGHYDDKDTL DLNTPVDKTS N                                    31

SEQ ID NO: 13            moltype = AA  length = 37
FEATURE                  Location/Qualifiers
source                   1..37
                         mol_type = protein
                         organism = Homo sapiens
SEQUENCE: 13
MDSFNYTTPD YGHYDDKDTL DLNTPVDKTS NTLRVPD                              37

SEQ ID NO: 14            moltype = AA  length = 37
FEATURE                  Location/Qualifiers
source                   1..37
                         mol_type = protein
                         organism = Macaca fascicularis
SEQUENCE: 14
MDPFSSTTLD YEHYDGKNVL DSDTPVDKTS NTLRVPD                              37

SEQ ID NO: 15            moltype = AA  length = 398
FEATURE                  Location/Qualifiers
source                   1..398
                         mol_type = protein
                         organism = synthetic construct
SEQUENCE: 15
AESHLSLLYH LTAVSSPAPG TPAFWVSGWL GPQQYLSYNS LRGEAEPCGA WVWENQVSWY     60
WEKETTDLRI KEKLFLEAFK ALGGKGPYTL QGLLGCELGP DNTSVPTAKF ALNGEEFMNF    120
DLKQGTWGGD WPEALAISQR WQQQKDAANK ELTFLLFSCP HRLREHLERG RGNLEWKEPP    180
SMRLKARPSS PGFSVLTCSA FSFYPPELQL RPLRNGLAAG TGQGDFGPNS DGSFHASSSL    240
TVKSGDEHHY CCIVQHAGLA QPLRVELESP AKSSVNSRGL NDIFEAQKIE WHEHHHHHHI    300
QRTPKIQVYS RHPAENGKSN FLNCYVSGFH PSDIEVDLLK NGERIEKVEH SDLSFSKDWS    360
FYLLYYTEFT PTEKDEYACR VNHVTLSQPK IVKWDRDM                            398

SEQ ID NO: 16            moltype = AA  length = 398
FEATURE                  Location/Qualifiers
source                   1..398
                         mol_type = protein
                         organism = synthetic construct
SEQUENCE: 16
AESHLSLLYH LTAVSSPAPG TPAFWVSGWL GPQQYLSYDS LRGQAEPCGA WVWENQVSWY     60
WEKETTDLRI KEKLFLEAFK ALGGKGPYTL QGLLGCELSP DNTSVPTAKF ALNGEEFM      120
DLKQGTWGGD WPEALAISQR WQQQKAANK ELTFLLFSCP HRLREHLERG RGNLEWKEPP     180
SMRLKARPGN PGFSVLTCSA FSFYPPELQL RPLRNGMAAG TGQGDFGPNS DGSFHASSSL    240
TVKSGDEHHY CCIVQHAGLA QPLRVELETP AKSSVNSRGL NDIFEAQKIE WHEHHHHHHI    300
QRTPKIQVYS RHPPENGKPN FLNCYVSGFH PSDIEVDLLK NGEKMGKVEH SDLSFSKDWS    360
FYLLYYTEFT PNEKDEYACR VNHVTLSGPR TVKWDRDM                            398

SEQ ID NO: 17            moltype = AA  length = 400
FEATURE                  Location/Qualifiers
source                   1..400
                         mol_type = protein
                         organism = synthetic construct
SEQUENCE: 17
SETRPPLMYH LTAVSNPSTG LPSFWATGWL GPQQYLTYNS LRQEADPCGA WMWENQVSWY     60
WEKETTDLKS KEQLFLEALK TLEKILNGTY TLQGLLGCEL ASDNSSVPTA VFALNGEEFM    120
KFNPRIGNWT GEWPETEIVA NLWMKQPDAA RKESEFLLNS CPERLLGHLE RGRRNLEWKE    180
PPSMRLKARP GNSGSSVLTC AAFSYPPEL KFRFLRNGLA SGSGNCSTGP NGDGSFHAWS    240
LLEVKRGDEH HYQCQVEHEG LAQPLTVDLD SSARSSVNSR GLNDIFEAQK IEWHEHHHHH    300
HIQKTPQIQV YSRHPPENGK PNILNCYVTG FHPPHIEIQM LKNGKKIPKV EMSDMSFSKD    360
WSFYILAHTE FTPTETDTYA CRVKHDSMAE PKTVYWDRDM                          400

SEQ ID NO: 18            moltype = AA  length = 274
FEATURE                  Location/Qualifiers
source                   1..274
                         mol_type = protein
                         organism = synthetic construct
SEQUENCE: 18
QVDTTKAVIT LQPPWVSVFQ EETVTLHCEV LHLPGSSSTQ WFLNGTATQT STPSYRITSA     60
SVNDSGEYRC QRGLSGRSDP IQLEIHRGWL LLQVSSRVFT EGEPLALRCH AWKDKLVYNV    120
LYYRNGKAFK FFHWNSNLTI LKTNISHNGT YHCSGMGKHR YTSAGISVTV KELFPAPVLN    180
ASVTSPLLEG NLVTLSCETK LLLQRPGLQL YFSFYMGSKT LRGRNTSSEY QILTARREDS    240
GLYWCEAATE DGNVLKRSPE LELQVNSRHH HHH                                 274
```

-continued

```
SEQ ID NO: 19              moltype = AA   length = 186
FEATURE                    Location/Qualifiers
source                     1..186
                           mol_type = protein
                           organism = synthetic construct
SEQUENCE: 19
QAAAPPKAVL KLEPPWINVL QEDSVTLTCQ GARSPESDSI QWFHNGNLIP THTQPSYRFK   60
ANNNDSGEYT CQTGQTSLSD PVHLTVLSEW LVLQTPHLEF QEGETIMLRC HSWKDKPLVK  120
VTFFQNGKSQ KFSHLDPTFS IPQANHSHSG DYHCTGNIGY TLFSSKPVTI TVQVPSVNSR  180
HHHHHH                                                             186

SEQ ID NO: 20              moltype = AA   length = 186
FEATURE                    Location/Qualifiers
source                     1..186
                           mol_type = protein
                           organism = synthetic construct
SEQUENCE: 20
QAAAPPKAVL KLEPPWINVL QEDSVTLTCQ GARSPESDSI QWFHNGNLIP THTQPSYRFK   60
ANNNDSGEYT CQTGQTSLSD PVHLTVLSEW LVLQTPHLEF QEGETIMLRC HSWKDKPLVK  120
VTFFQNGKSQ KFSRLDPTFS IPQANHSHSG DYHCTGNIGY TLFSSKPVTI TVQVPSVNSR  180
HHHHHH                                                             186

SEQ ID NO: 21              moltype = AA   length = 187
FEATURE                    Location/Qualifiers
source                     1..187
                           mol_type = protein
                           organism = synthetic construct
SEQUENCE: 21
GMRTEDLPKA VVFLEPQWYR VLEKDSVTLK CQGAYSPEDN STQWFHNESL ISSQASSYFI   60
DAATVDDSGE YRCQTNLSTL SDPVQLEVHI GWLLLQAPRW VFKEEDPIHL RCHSWKNTAL  120
HKVTYLQNGK GRKYFHHNSD FYIPKATLKD SGSYFCRGLF GSKNVSSETV NITITQGVNS  180
RHHHHHH                                                            187

SEQ ID NO: 22              moltype = AA   length = 187
FEATURE                    Location/Qualifiers
source                     1..187
                           mol_type = protein
                           organism = synthetic construct
SEQUENCE: 22
GMRTEDLPKA VVFLEPQWYR VLEKDSVTLK CQGAYSPEDN STQWFHNESL ISSQASSYFI   60
DAATVDDSGE YRCQTNLSTL SDPVQLEVHI GWLLLQAPRW VFKEEDPIHL RCHSWKNTAL  120
HKVTYLQNGK GRKYFHHNSD FYIPKATLKD SGSYFCRGLV GSKNVSSETV NITITQGVNS  180
RHHHHHH                                                            187

SEQ ID NO: 23              moltype = AA   length = 186
FEATURE                    Location/Qualifiers
source                     1..186
                           mol_type = protein
                           organism = synthetic construct
SEQUENCE: 23
TPAAPPKAVL KLEPQWINVL QEDSVTLTCR GTHSPESDSI QWFHNGNLIP THTQPSYRFK   60
ANNNDSGEYT CQTGQTSLSD PVHLTVLSEW LVLQTPHLEF QEGETIVLRC HSWKDKPLVK  120
VTFFQNGKSK KFSRSDPNFS IPQANHSHSG DYHCTGNIGY TLYSSKPVTI TVQAPSDNSR  180
HHHHHH                                                             186

SEQ ID NO: 24              moltype = AA   length = 907
FEATURE                    Location/Qualifiers
source                     1..907
                           mol_type = protein
                           organism = synthetic construct
SEQUENCE: 24
DGSHHHHHHG TMDSFNYTTP DYGHYDDKDT LDLNTPVDKT SNTLRVPDIL ALVIFAVVFL   60
VGVLGNALVV WVTAFEAKRT INAIWFLNLA VADFLSCLAL PILFTSIVQH HHWPFGGAVL  120
SILPSLILLN MYASILLLAT ISADRFLLVF KPIWCQNFRG AGLAWIACAV AWGLALLLTI  180
PSFLYRVVRE EYFPPKVLCG VDYSHDKRRE RAVAIVRLVL GFLWPLLTLT ICYTFILLRT  240
WSRRATRSTK TLKVVAVVA SFFIFWLPYQ VTGIMMSFLE PSSPTFLLLK KLDSLCVSFA  300
YINCCINPII YVVAGQGFQG RLRKSLPSLL RNVLTEESVV RESKSFTRST VDTMAQKTQA  360
VDIDYKDDDD KIEGRMDGAR ASVLSGGELD RWEKIRLRPG GKKKYKLKHI VWASRELERF  420
AVNPGLLETS EGCRQILGQL QPSLQTGSEE LRSLYNTVAT LYCVHQRIEI KDTKEALDKI  480
EEEQNKSKKK AQQAAADTGH SSQVSQNYPI VQNIQGQMVH QAISPRTLNA WVKVVEEKAF  540
SPEVIPMFSA LSEGATPQDL NTMLNTVGGH QAAMQMLKET INEEAAEWDR VHPVHAGPIA  600
PGQMREPRGS DIAGTTSTLQ EQIGWMTNNP PIPVGEIYKR WIILGLNKIV RMYSPTSILD  660
IRQGPKEPFR DYVDRFYKTL RAEQASQEVK NWMTETLLVQ NANPDCKTIL KALGPAATLE  720
EMMTACQGVG GPGHKARVLA EAMSQVTNTA TIMMQRGNFR NQRKMVKCFN CGKEGHTARN  780
CRAPRKKGCW KCGKEGHQMK DCTERQANFL GKIWPSYKGR PGNFLQSRPE PTAPPFLQSR  840
PEPTAPPEES FRSGVETTTP PQKQEPIDKE LYPLTSLRSL FGNDPSSQVN SRGLNDIFEA  900
QKIEWHE                                                            907

SEQ ID NO: 25              moltype = AA   length = 874
```

```
FEATURE                 Location/Qualifiers
source                  1..874
                        mol_type = protein
                        organism = synthetic construct
SEQUENCE: 25
DGSHHHHHHG TMNSFNYTTP DYGHYDDKDT LDLNTPVDKT SNTLRVPDIL ALVIFAVVFL    60
VGVLGNALVV WVTAFEAKRT INAIWFLNLA VADFLSCLAL PILFTSIVQH HHWPFGGAAC   120
SILPSLILLN MYASILLLAT ISADRFLLVF KPIWCQNFRG AGLAWIACAV AWGLALLLTI   180
PSFLYRVVRE EYFPPKVLCG VDYSHDKRRE RAVAIVRLVL GFLWPLLTLT ICYTFILLRT   240
WSRRATRSTK TLKVVAVVA SFFIFWLPYQ VTGIMMSFLE PSSPTFLLLN KLDSLCVSFA   300
YINCCINPII YVVAGQGFQG RLRKSLPSLL RNVLTEESVV RESKSFTRST VDTMAQKTQA   360
VDIGARASVL SGGELDRWEK IRLRPGGKKK YKLKHIVWAS RELERFAVNP GLLETSEGCR   420
QILGQLQPSL QTGSEELRSL YNTVATLYCV HQRIEIKDTK EALDKIEEEQ NKSKKKAQQA   480
AADTGHSSQV SQNYPIVQNI QGQMVHQAIS PRTLNAWVKV VEEKAFSPEV IPMFSALSEG   540
ATPQDLNTML NTVGGHQAAM QMLKETINEE AAEWDRVHPV HAGPIAPGQM REPRGSDIAG   600
TTSTLQEQIG WMTNNPPIPV GEIYKRWIIL GLNKIVRMYS PTSILDIRQG PKEPFRDYVD   660
RFYKTLRAEQ ASQEVKNWMT ETLLVQNANP DCKTILKALG PAATLEEMMT ACQGVGGPGH   720
KARVLAEAMS QVTNTATIMM QRGNFRNQRK MVKCFNCGKE GHTARNCRAP RKKGCWKCGK   780
EGHQMKDCTE RQANFLGKIW PSYKGRPGNF LQSRPEPTAP PFLQSRPEPT APPEESFRSG   840
VETTTPPQKQ EPIDKELYPL TSLRSLFGND PSSQ                              874

SEQ ID NO: 26           moltype = AA  length = 908
FEATURE                 Location/Qualifiers
source                  1..908
                        mol_type = protein
                        organism = synthetic construct
SEQUENCE: 26
DGSHHHHHHG TMDPIDNSSF EINYDHYGTM APNIPADGIH LPKRQPGDVA ALIIYSVVFL    60
VGVPGNALVV WVTAFEARRA VNAIWFLNLA VADLLSCLAL PVLFTTVLNH NYWYFDATAC   120
IVLPSLILLN MYASILLLAT ISADRFLLVF KPIWCQVRG TGLAWMACGV AWVLALLLTI   180
PSFVYREAYK DFYSEHTVCG INYGGGSFPK EKAVAILRLM VGFVLPLLTL NICYTFLLLR   240
TWSRKATRST KTLKVVMAVV ICFFIFWLPY QVTGVMIAWL PPSSPTLKRV EKLNSLCVSL   300
AYINCCVNPI IYVMAGQGFH GRLLRSLPSI IRNALSEDSV GRDSKTFTPS TTDTSTRKSQ   360
AVDIDYKDDD DKIEGRMDGA RASVLSGGEL DRWEKIRLRP GGKKKYKLKH IWWASRELER   420
FAVNPGLLET SEGCRQILGQ LQPSLQTGSE ELRSLYNTVA TLYCVHQRIE IKDTKEALDK   480
IEEEQNKSKK KAQQAAADTG HSSQVSQNYP IVQNIQGQMV HQAISPRTLN AWVKVVEEKA   540
FSPEVIPMFS ALSEGATPQD LNTMLNTVGG HQAAMQMLKE TINEEAAEWD RVHPVHAGPI   600
APGQMREPRG SDIAGTTSTL QEQIGWMTNN PPIPVGEIYK RWIILGLNKI VRMYSPTSIL   660
DIRQGKEPF RDYVDRFYKT LRAEQASQEV KNWMTETLLV QNANPDCKTI LKALGPAATL   720
EEMMTACQGV GGPGHKARVL AEAMSQVTNT ATIMMQRGNF RNQRKMVKCF NCGKEGHTAR   780
NCRAPRKKGC WKCGKEGHQM KDCTERQANF LGKIWPSYKG RPGNFLQSRP EPTAPPFLQS   840
RPEPTAPPEE SFRSGVETTT PPQKQEPIDK ELYPLTSLRS LFGNDPSSQV NSRGLNDIFE   900
AQKIEWHE                                                          908

SEQ ID NO: 27           moltype = AA  length = 5
FEATURE                 Location/Qualifiers
source                  1..5
                        mol_type = protein
                        organism = synthetic construct
SEQUENCE: 27
SYAMH                                                                5

SEQ ID NO: 28           moltype = AA  length = 19
FEATURE                 Location/Qualifiers
source                  1..19
                        mol_type = protein
                        organism = synthetic construct
SEQUENCE: 28
RIKSKAQGGT TDYAAHVKG                                                19

SEQ ID NO: 29           moltype = AA  length = 8
FEATURE                 Location/Qualifiers
source                  1..8
                        mol_type = protein
                        organism = synthetic construct
SEQUENCE: 29
VSFSTFDV                                                             8

SEQ ID NO: 30           moltype = AA  length = 7
FEATURE                 Location/Qualifiers
source                  1..7
                        mol_type = protein
                        organism = synthetic construct
SEQUENCE: 30
GFTFSSY                                                              7

SEQ ID NO: 31           moltype = AA  length = 8
FEATURE                 Location/Qualifiers
source                  1..8
```

```
                        mol_type = protein
                        organism = synthetic construct
SEQUENCE: 31
KSKAQGGT                                                                 8

SEQ ID NO: 32           moltype = AA   length = 13
FEATURE                 Location/Qualifiers
source                  1..13
                        mol_type = protein
                        organism = synthetic construct
SEQUENCE: 32
SGSSSNIGSY YVS                                                          13

SEQ ID NO: 33           moltype = AA   length = 7
FEATURE                 Location/Qualifiers
source                  1..7
                        mol_type = protein
                        organism = synthetic construct
SEQUENCE: 33
RNNQRPS                                                                  7

SEQ ID NO: 34           moltype = AA   length = 10
FEATURE                 Location/Qualifiers
source                  1..10
                        mol_type = protein
                        organism = synthetic construct
SEQUENCE: 34
DSWDHSSMNV                                                              10

SEQ ID NO: 35           moltype = AA   length = 119
FEATURE                 Location/Qualifiers
source                  1..119
                        mol_type = protein
                        organism = synthetic construct
SEQUENCE: 35
EVQLVESGGG LVKPGGSLRL SCAASGFTFS SYAMHWVRQA PGKGLEWVGR IKSKAQGGTT        60
DYAAHVKGRF TISRDDSKNT LYLQMNSLKT EDTAVYYCAR VSFSTFDVWG QGTLVTVSS        119

SEQ ID NO: 36           moltype = AA   length = 111
FEATURE                 Location/Qualifiers
source                  1..111
                        mol_type = protein
                        organism = synthetic construct
SEQUENCE: 36
QSVLTQPPSV SGAPGQRVTI SCSGSSSNIG SYYVSWYQQL PGTAPKVLIY RNNQRPSGVP        60
DRFSGSKSGT SASLAITGLQ AEDEADYYCD SWDHSSMNVF GGGTKLTVLG Q                111

SEQ ID NO: 37           moltype = AA   length = 449
FEATURE                 Location/Qualifiers
source                  1..449
                        mol_type = protein
                        organism = synthetic construct
SEQUENCE: 37
EVQLVESGGG LVKPGGSLRL SCAASGFTFS SYAMHWVRQA PGKGLEWVGR IKSKAQGGTT        60
DYAAHVKGRF TISRDDSKNT LYLQMNSLKT EDTAVYYCAR VSFSTFDVWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKRVEPK SCDKTHTCPP CPAPEAEGAP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PSSIEKTISK AKGQPREPQV YTLPPSREEM       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                        449

SEQ ID NO: 38           moltype = AA   length = 215
FEATURE                 Location/Qualifiers
source                  1..215
                        mol_type = protein
                        organism = synthetic construct
SEQUENCE: 38
QSVLTQPPSV SGAPGQRVTI SCSGSSSNIG SYYVSWYQQL PGTAPKVLIY RNNQRPSGVP        60
DRFSGSKSGT SASLAITGLQ AEDEADYYCD SWDHSSMNVF GGGTKLTVLG QPKAAPSVTL       120
FPPSSEELQA NKATLVCLIS DFYPGAVTVA WKADSSPVKA GVETTTPSKQ SNNKYAASSY       180
LSLTPEQWKS HRSYSCQVTH EGSTVEKTVA PTECS                                 215

SEQ ID NO: 39           moltype = AA   length = 19
FEATURE                 Location/Qualifiers
source                  1..19
                        mol_type = protein
                        organism = synthetic construct
SEQUENCE: 39
```

```
RIKSVAQGGT TDYAAHVKG                                                     19

SEQ ID NO: 40              moltype = AA  length = 8
FEATURE                    Location/Qualifiers
source                     1..8
                           mol_type = protein
                           organism = synthetic construct
SEQUENCE: 40
VSHSTFDV                                                                  8

SEQ ID NO: 41              moltype = AA  length = 8
FEATURE                    Location/Qualifiers
source                     1..8
                           mol_type = protein
                           organism = synthetic construct
SEQUENCE: 41
KSVAQGGT                                                                  8

SEQ ID NO: 42              moltype = AA  length = 119
FEATURE                    Location/Qualifiers
source                     1..119
                           mol_type = protein
                           organism = synthetic construct
SEQUENCE: 42
EVQLVESGGG LVKPGGSLRL SCAASGFTFS SYAMHWVRQA PGKGLEWVGR IKSVAQGGTT          60
DYAAHVKGRF TISRDDSKNT LYLQMNSLKT EDTAVYYCAR VSHSTFDVWG QGTLVTVSS          119

SEQ ID NO: 43              moltype = AA  length = 111
FEATURE                    Location/Qualifiers
source                     1..111
                           mol_type = protein
                           organism = synthetic construct
SEQUENCE: 43
QSVLTQPPSV SGAPGQRVTI SCSGSSSNIG SYYVSWYQQL PGTAPKVLIY RNNQRPSGVP          60
DRFSGSKSGT SASLAITGLQ AEDEADYYCD SWDHSSMNVF GGGTKLTVLG Q                  111

SEQ ID NO: 44              moltype = AA  length = 449
FEATURE                    Location/Qualifiers
source                     1..449
                           mol_type = protein
                           organism = synthetic construct
SEQUENCE: 44
EVQLVESGGG LVKPGGSLRL SCAASGFTFS SYAMHWVRQA PGKGLEWVGR IKSVAQGGTT          60
DYAAHVKGRF TISRDDSKNT LYLQMNSLKT EDTAVYYCAR VSHSTFDVWG QGTLVTVSSA         120
STKGPSVFPL APSSKSTSGG TAALGCLVKD YFPEPVTVSW NSGALTSGVH TFPAVLQSSG         180
LYSLSSVVTV PSSSLGTQTY ICNVNHKPSN TKVDKRVEPK SCDKTHTCPP CPAPEAEGAP         240
SVFLFPPKPK DTLMISRTPE VTCVVVDVSH EDPEVKFNWY VDGVEVHNAK TKPREEQYNS         300
TYRVVSVLTV LHQDWLNGKE YKCKVSNKAL PSSIEKTISK AKGQPREPQV YTLPPSREEM         360
TKNQVSLTCL VKGFYPSDIA VEWESNGQPE NNYKTTPPVL DSDGSFFLYS KLTVDKSRWQ         420
QGNVFSCSVM HEALHNHYTQ KSLSLSPGK                                          449

SEQ ID NO: 45              moltype = AA  length = 215
FEATURE                    Location/Qualifiers
source                     1..215
                           mol_type = protein
                           organism = synthetic construct
SEQUENCE: 45
QSVLTQPPSV SGAPGQRVTI SCSGSSSNIG SYYVSWYQQL PGTAPKVLIY RNNQRPSGVP          60
DRFSGSKSGT SASLAITGLQ AEDEADYYCD SWDHSSMNVF GGGTKLTVLG QPKAAPSVTL         120
FPPSSEELQA NKATLVCLIS DFYPGAVTVA WKADSSPVKA GVETTTPSKQ SNNKYAASSY         180
LSLTPEQWKS HRSYSCQVTH EGSTVEKTVA PTECS                                   215

SEQ ID NO: 46              moltype = DNA  length = 15
FEATURE                    Location/Qualifiers
source                     1..15
                           mol_type = other DNA
                           organism = synthetic construct
SEQUENCE: 46
agctatgcga tgcac                                                         15

SEQ ID NO: 47              moltype = DNA  length = 57
FEATURE                    Location/Qualifiers
source                     1..57
                           mol_type = other DNA
                           organism = synthetic construct
SEQUENCE: 47
cgtatcaaat ccaaagccca gggcggtacg accgactacg cggcgcacgt gaaaggc           57

SEQ ID NO: 48              moltype = DNA  length = 24
```

-continued

```
FEATURE                 Location/Qualifiers
source                  1..24
                        mol_type = other DNA
                        organism = synthetic construct
SEQUENCE: 48
gtttctttct ccactttcga tgtt                                              24

SEQ ID NO: 49           moltype = DNA   length = 21
FEATURE                 Location/Qualifiers
source                  1..21
                        mol_type = other DNA
                        organism = synthetic construct
SEQUENCE: 49
ggatttacct tcagcagcta t                                                 21

SEQ ID NO: 50           moltype = DNA   length = 24
FEATURE                 Location/Qualifiers
source                  1..24
                        mol_type = other DNA
                        organism = synthetic construct
SEQUENCE: 50
aaatccaaag cccaggcgg tacg                                               24

SEQ ID NO: 51           moltype = DNA   length = 39
FEATURE                 Location/Qualifiers
source                  1..39
                        mol_type = other DNA
                        organism = synthetic construct
SEQUENCE: 51
agcggcagct cctccaatat tggtagctat tacgtgagc                              39

SEQ ID NO: 52           moltype = DNA   length = 21
FEATURE                 Location/Qualifiers
source                  1..21
                        mol_type = other DNA
                        organism = synthetic construct
SEQUENCE: 52
cgtaataatc aacgtcctag c                                                 21

SEQ ID NO: 53           moltype = DNA   length = 30
FEATURE                 Location/Qualifiers
source                  1..30
                        mol_type = other DNA
                        organism = synthetic construct
SEQUENCE: 53
gacagctggg atcacagctc catgaatgtt                                        30

SEQ ID NO: 54           moltype = DNA   length = 357
FEATURE                 Location/Qualifiers
source                  1..357
                        mol_type = other DNA
                        organism = synthetic construct
SEQUENCE: 54
gaggtgcaat tggtggaaag cggcggtggc ctggtgaaac caggcggcag cctgcgcctg       60
agctgcgccg cctccggatt taccttcagc agctatgcga tgcactgggt gcgccaggcc      120
ccgggcaaag gtctcgaatg ggtgggtcgt atcaaatcca agcccaggg cggtacgacc       180
gactacgcgg cgcacgtgaa aggccgcttt accattagcc gcgatgattc gaaaaacacc      240
ctgtatctgc aaatgaacag cctgaaaacc gaagatacgg ccgtgtatta ttgcgcgcgt      300
gtttctttct ccactttcga tgtttgggc caaggcaccc tggtgactgt ctcgagc          357

SEQ ID NO: 55           moltype = DNA   length = 333
FEATURE                 Location/Qualifiers
source                  1..333
                        mol_type = other DNA
                        organism = synthetic construct
SEQUENCE: 55
cagagcgtgc tgacccagcc tcctagcgtg agcggtgcac cgggccagcg cgtgaccatt       60
agctgtagcg gcagctcctc caatattggt agctattacg tgagctggta tcagcagctg      120
ccgggcaaag cgccgaaagt tctgatctat cgtaataatc aacgtcctag cggcgtgccg      180
gatcgcttta cgggatccaa aagcggcacc agcgccagcc tggcgattac cggcctgcaa      240
gcagaagatg aagcggatta ttactgcgac agctgggatc acagctccat gaatgttttt      300
ggcggcggta ccaagctgac cgtgctgggc cag                                   333

SEQ ID NO: 56           moltype = DNA   length = 1347
FEATURE                 Location/Qualifiers
source                  1..1347
                        mol_type = other DNA
                        organism = synthetic construct
SEQUENCE: 56
```

-continued

```
gaggtgcaat tggtggaaag cggcggtggc ctggtgaaac caggcggcag cctgcgcctg    60
agctgcgccg cctccggatt taccttcagc agctatgcga tgcactgggt gcgccaggcc   120
ccgggcaaag gtctcgaatg ggtgggtcgt atcaaatcca aagcccaggg cggtacgacc   180
gactacgcgc gcacgtgaa aggccgcttt accattagcc gcgatgattc gaaaaacacc    240
ctgtatctgc aaatgaacag cctgaaaacc gaagatgacc ccgtgtatta ttgcgcgcgt   300
gtttctttct ccactttcga tgtttggggc caaggcaccc tggtgactgt ctcgagcgcg   360
tcgaccaaag gcccagcgt gttccctctg gccccagca gcaagagcac ctctggcgga    420
acagccgccc tgggctgcct ggtcaaggac tacttccccg agcccgtgac cgtgtcctgg   480
aactctggcg cccctgaccag cggcgtgcac acctttccag ccgtgctcca gagcagcggc   540
ctgtacagcc tgagcagcgt cgtgaccgtg cccagcagca gcctgggcac ccagacctac   600
atctgcaacg tgaaccacaa gcccagcaac acaaaggtgg acaagcgggt ggaacccaag   660
agctgcgaca gacccacac ctgtcccccc tgccctgccc ctgaagcgga gggagccccc    720
tccgtgttcc tgttcccccc aaagcctaag gacaccctga tgatcagccg gaccccgaa    780
gtgacctgcg tggtggtgga cgtgtcccac gaggaccctg aagtgaagtt taattggtac   840
gtggacggcg tggaagtgca caacgccaag accaagccca gagaggaaca gtacaacagc   900
acctaccggg tggtgtccgt gctgaccgtg ctgcaccagg actggctgaa cggcaaagag   960
tacaagtgca aggtgtccaa caaggccctg ccttcctcca tcgagaaaac catcagcaag  1020
gccaaaggcc agcccgcga gccccaggtg tacacactgc ccctagccg ggaagagatg    1080
accaagaacc aggtgtccct gacctgcctc gtgaagggct tctaccccag cgacattgcc  1140
gtggaatggg agagcaacgg ccagcccgag aacaactaca agaccacccc cctgtgctg   1200
gacagcgacg gctcattctt cctgtacagc aagctgaccg tggacaagag ccggtggcag  1260
cagggcaacg tgttcagctg ctccgtgatg cacgaggccc tgcacaacca ctacacccag  1320
aagtccctga gcctgagccc cggcaag                                      1347

SEQ ID NO: 57            moltype = DNA   length = 645
FEATURE                  Location/Qualifiers
source                   1..645
                         mol_type = other DNA
                         organism = synthetic construct
SEQUENCE: 57
cagagcgtgc tgacccagcc tcctagcgtg agcggtgcac cgggccagcg cgtgaccatt    60
agctgtagcg gcagctcctc caatattggt agctattacg tgagctggta tcagcagctg   120
ccgggcacgg cgccgaaagt tctgatctat cgtaataatc aacgtcctag cggcgtgccg   180
gatcgcttta gcggatccaa gcgggcacc agcgccagcc tggcgattac cggcctgcaa   240
gcagaagatg aagcggatta ttactgcgac agctgggatc acagctccat gaatgtttat   300
ggcggcggta ccaagctgac cgtgctgggc cagcccaaag ccgccccag cgtgaccctg   360
ttccccccct cgagtgagga actccaggcc aacaaggcca ccctcgtgtg cctgatcagc  420
gacttctacc ctggcgccgt gaccgtggcc tggaaggccg atagcagccc tgtgaaggcc  480
ggcgtgaga ccaccacccc cagcaagcag agcaacaaca atacgccgc cagcagctac    540
ctgagcctga ccccagca gtggaagtcc cacagatcct acagctgcca ggtcacacac    600
gagggcagca ccgtggaaaa gaccgtggcc cccaccgagt gcagc                  645

SEQ ID NO: 58            moltype = DNA   length = 15
FEATURE                  Location/Qualifiers
source                   1..15
                         mol_type = other DNA
                         organism = synthetic construct
SEQUENCE: 58
agctatgcga tgcac                                                    15

SEQ ID NO: 59            moltype = DNA   length = 57
FEATURE                  Location/Qualifiers
source                   1..57
                         mol_type = other DNA
                         organism = synthetic construct
SEQUENCE: 59
cgtatcaaat ccgtggccca gggcggtacg accgactacg cggcgcacgt gaaaggc      57

SEQ ID NO: 60            moltype = DNA   length = 24
FEATURE                  Location/Qualifiers
source                   1..24
                         mol_type = other DNA
                         organism = synthetic construct
SEQUENCE: 60
gtttctcatt ccactttcga tgtt                                          24

SEQ ID NO: 61            moltype = DNA   length = 21
FEATURE                  Location/Qualifiers
source                   1..21
                         mol_type = other DNA
                         organism = synthetic construct
SEQUENCE: 61
ggatttacct tcagcagcta t                                             21

SEQ ID NO: 62            moltype = DNA   length = 24
FEATURE                  Location/Qualifiers
source                   1..24
                         mol_type = other DNA
                         organism = synthetic construct
```

```
SEQUENCE: 62
aaatccgtgg cccagggcgg tacg                                          24

SEQ ID NO: 63           moltype = DNA   length = 39
FEATURE                 Location/Qualifiers
source                  1..39
                        mol_type = other DNA
                        organism = synthetic construct
SEQUENCE: 63
agcggcagct cctccaatat tggtagctat tacgtgagc                           39

SEQ ID NO: 64           moltype = DNA   length = 21
FEATURE                 Location/Qualifiers
source                  1..21
                        mol_type = other DNA
                        organism = synthetic construct
SEQUENCE: 64
cgtaataatc aacgtcctag c                                             21

SEQ ID NO: 65           moltype = DNA   length = 30
FEATURE                 Location/Qualifiers
source                  1..30
                        mol_type = other DNA
                        organism = synthetic construct
SEQUENCE: 65
gacagctggg atcacagctc catgaatgtt                                    30

SEQ ID NO: 66           moltype = DNA   length = 357
FEATURE                 Location/Qualifiers
source                  1..357
                        mol_type = other DNA
                        organism = synthetic construct
SEQUENCE: 66
gaggtgcaat tggtggaaag cggcggtggc ctggtgaaac caggcggcag cctgcgcctg    60
agctgcgccg cctccggatt taccttcagc agctatgcga tgcactgggt gcgccaggcc   120
ccgggcaaag gtctcgaatg ggtgggtcgt atcaaatccg tggcccaggg cggtacgacc   180
gactacgcgg cgcacgtgaa aggccgcttt accattagcc gcgatgattc gaaaaacacc   240
ctgtatctgc aaatgaacag cctgaaaacc gaagatacgg ccgtgtatta ttgcgcgcgt   300
gtttctcatt ccactttcga tgtttgggc caaggcaccc tggtgactgt ctcgagc      357

SEQ ID NO: 67           moltype = DNA   length = 333
FEATURE                 Location/Qualifiers
source                  1..333
                        mol_type = other DNA
                        organism = synthetic construct
SEQUENCE: 67
cagagcgtgc tgacccagcc tcctagcgtg agcggtgcac cgggccagcg cgtgaccatt    60
agctgtagcg gcagctcctc caatattggt agctattacg tgagctggta tcagcagctg   120
ccgggcacgg cgccgaaagt tctgatctat cgtaataatc aacgtcctag cggcgtgccg   180
gatcgcttta gcggatccaa aagcggcacc agcgccagcc tggcgattac cggcctgcaa   240
gcagaagatg aagcggatta ttactgcgac agctgggatc acagctccat gaatgttttt   300
ggcggcggta ccaagctgac cgtgctgggc cag                                333

SEQ ID NO: 68           moltype = DNA   length = 1347
FEATURE                 Location/Qualifiers
source                  1..1347
                        mol_type = other DNA
                        organism = synthetic construct
SEQUENCE: 68
gaggtgcaat tggtggaaag cggcggtggc ctggtgaaac caggcggcag cctgcgcctg    60
agctgcgccg cctccggatt taccttcagc agctatgcga tgcactgggt gcgccaggcc   120
ccgggcaaag gtctcgaatg ggtgggtcgt atcaaatccg tggcccaggg cggtacgacc   180
gactacgcgg cgcacgtgaa aggccgcttt accattagcc gcgatgattc gaaaaacacc   240
ctgtatctgc aaatgaacag cctgaaaacc gaagatacgg ccgtgtatta ttgcgcgcgt   300
gtttctcatt ccactttcga tgtttgggc caaggcaccc tggtgactgt ctcgagcgcg   360
tcgaccaaag gcccagcgt gttccctctg gccccagca gcaagagcac ctctggcgga   420
acagccgccc tgggctgcct ggtcaaggac tacttcccg agcccgtgac cgtgtcctgc   480
aactctggcc ccctgaccag cggcgtgcac acctttccag ccgtgctcca gagcagcggc   540
ctgtacagcg tgagcagcgt cgtgaccgtg cccagcagca gcctgggcac ccagacctac   600
atctgcaacg tgaaccacaa gcccagcaac acaaaggtgg acaagcgggt ggaacccaag   660
agctgcgaca gacccacac ctgtcccccc tgccctgccc ctgaagcgga gggagccccc   720
tccgtgttcc tgttcccccc aaagcctaag gacaccctga tgatcagccg gacccccgaa   780
gtgacctgcg tggtggtgga cgtgtcccac gaggaccctg aagtgaagtt taattggtac   840
gtggacggcg tggaagtgca caacgccaag accaagccca gagaggaaca gtacaacagc   900
acctaccggg tggtgtccgt gctgaccgtg ctgcaccagg actggctgaa cggcaaagag   960
tacaagtgca aggtgtccaa caaggccctg ccttcctcca tcgagaaaac catcagcaag  1020
gccaaaggc agccccgcga gccccaggtg tacacactgc ccctagccg ggaagagatg   1080
accaagaacc aggtgtccct gacctgctc gtgaagggct ctaccccag cgacattgcc   1140
gtggaatggg agagcaacgg ccagcccgag aacaactaca agaccacccc cctgtgctg   1200
```

```
gacagcgacg gctcattctt cctgtacagc aagctgaccg tggacaagag ccggtggcag   1260
cagggcaacg tgttcagctg ctccgtgatg cacgaggccc tgcacaacca ctacacccag   1320
aagtccctga gcctgagccc cggcaag                                       1347

SEQ ID NO: 69          moltype = DNA   length = 645
FEATURE                Location/Qualifiers
source                 1..645
                       mol_type = other DNA
                       organism = synthetic construct
SEQUENCE: 69
cagagcgtgc tgacccagcc tcctagcgtg agcggtgcac cgggccagcg cgtgaccatt   60
agctgtagcg gcagctcctc caatattggt agctattacg tgagctggta tcagcagctg   120
ccgggcacgg cgccgaaagt tctgatctat cgtaataatc aacgtcctag cggcgtgccg   180
gatcgcttta gcggatccaa aagcggcacc agcgccagcc tggcgattac cggcctgcaa   240
gcagaagatg aagcggatta ttactgcgca agctgggatc acagctccat gaatgttttt   300
ggcggcggta ccaagctgac cgtgctgggc cagcccaaag ccgccctag cgtgaccctg   360
ttcccccct cgagtgagga actccaggcc aacaaggcca ccctcgtgtg cctgatcagc   420
gacttctacc ctggcgccgt gaccgtgtgg aaggacaaca tagcagccc tgtgaaggcc   480
ggcgtggaaa ccaccacccc cagcaagcag agcaacaaca atacgccgc cagcagctac   540
ctgagcctga ccccgagca gtggaagtcc cacagatcct acagctgcca ggtcacacac   600
gagggcagca ccgtggaaaa gaccgtggcc cccaccgagt gcagc                   645

SEQ ID NO: 70          moltype = DNA   length = 15
FEATURE                Location/Qualifiers
source                 1..15
                       mol_type = other DNA
                       organism = synthetic construct
SEQUENCE: 70
agctacgcta tgcac                                                    15

SEQ ID NO: 71          moltype = DNA   length = 57
FEATURE                Location/Qualifiers
source                 1..57
                       mol_type = other DNA
                       organism = synthetic construct
SEQUENCE: 71
cggatcaaga gcaaggctca aggcggcacc accgattacg ccgctcatgt gaagggc      57

SEQ ID NO: 72          moltype = DNA   length = 24
FEATURE                Location/Qualifiers
source                 1..24
                       mol_type = other DNA
                       organism = synthetic construct
SEQUENCE: 72
gtgtccttct ccaccttcga tgtg                                          24

SEQ ID NO: 73          moltype = DNA   length = 21
FEATURE                Location/Qualifiers
source                 1..21
                       mol_type = other DNA
                       organism = synthetic construct
SEQUENCE: 73
ggcttcacct tctccagcta c                                             21

SEQ ID NO: 74          moltype = DNA   length = 24
FEATURE                Location/Qualifiers
source                 1..24
                       mol_type = other DNA
                       organism = synthetic construct
SEQUENCE: 74
aagagcaagg ctcaaggcgg cacc                                          24

SEQ ID NO: 75          moltype = DNA   length = 39
FEATURE                Location/Qualifiers
source                 1..39
                       mol_type = other DNA
                       organism = synthetic construct
SEQUENCE: 75
tccggctcct cctccaacat cggctcctac tacgtgtcc                          39

SEQ ID NO: 76          moltype = DNA   length = 21
FEATURE                Location/Qualifiers
source                 1..21
                       mol_type = other DNA
                       organism = synthetic construct
SEQUENCE: 76
cggaacaacc agcggccttc t                                             21

SEQ ID NO: 77          moltype = DNA   length = 30
```

```
FEATURE                 Location/Qualifiers
source                  1..30
                        mol_type = other DNA
                        organism = synthetic construct
SEQUENCE: 77
gactcttggg accactcctc catgaacgtg                                            30

SEQ ID NO: 78           moltype = DNA   length = 357
FEATURE                 Location/Qualifiers
source                  1..357
                        mol_type = other DNA
                        organism = synthetic construct
SEQUENCE: 78
gaagtgcagc tggtggaatc tggcggcgga cttgtgaaac ctggcggctc tctgagactg           60
tcttgtgccg cttccggctt caccttctcc agctacgcta tgcactgggt ccgacaggcc          120
cctggcaaag gattggagtg ggtcggacgg atcaagagca aggctcaagg cggcaccacc          180
gattacgccg ctcatgtgaa gggcagattc accatctctc gggacgactc caagaacacc          240
ctgtacctgc agatgaactc cctgaaaacc gaggacaccg ccgtgtacta ctgcgccaga          300
gtgtccttct ccaccttcga tgtgtgggggc cagggcacac tggttacagt ctcgagc            357

SEQ ID NO: 79           moltype = DNA   length = 333
FEATURE                 Location/Qualifiers
source                  1..333
                        mol_type = other DNA
                        organism = synthetic construct
SEQUENCE: 79
cagtccgtgc tgacccagcc tccttctgtt tctggtgctc ctggccagag agtgaccatc           60
tcttgctccg gctcctcctc caacatcggc tcctactacg tgtcctggta tcagcagctg          120
cctggcaccc tcctaaggt gctgatctac cggaacaacc agcggccttc tggcgtgccc           180
gatagattct ccggctctaa gtctggcacc tctgccagcc tggctatcac tggactgcag          240
gctgaggacg aggccgacta ctactgcgac tcttgggacc actcctccat gaacgtgttc          300
ggcggaggta ccaagctgac cgtgctggga cag                                       333

SEQ ID NO: 80           moltype = DNA   length = 1347
FEATURE                 Location/Qualifiers
source                  1..1347
                        mol_type = other DNA
                        organism = synthetic construct
SEQUENCE: 80
gaagtgcagc tggtggaatc tggcggcgga cttgtgaaac ctggcggctc tctgagactg           60
tcttgtgccg cttccggctt caccttctcc agctacgcta tgcactgggt ccgacaggcc          120
cctggcaaag gattggagtg ggtcggacgg atcaagagca aggctcaagg cggcaccacc          180
gattacgccg ctcatgtgaa gggcagattc accatctctc gggacgactc caagaacacc          240
ctgtacctgc agatgaactc cctgaaaacc gaggacaccg ccgtgtacta ctgcgccaga          300
gtgtccttct ccaccttcga tgtgtgggggc cagggcacac tggttacagt ctcgagcgcc         360
tccaccaaag gaccctctgt gtttcctctg gctccctcca gcaagtctac ctctggtgga          420
acagctgccc tgggctgcct ggtcaaggat tactttccag agcctgtgac cgtgtcctgg          480
aactctggcg ctctgacatc tggcgtgcac acctttccag ctgtgctgca gtcctctggc          540
ctgtacagcc tgtcctctgt cgtgaccgtg ccttctagct ctctgggcac ccagacctac          600
atctgcaatg tgaaccacaa gccttccaac accaaggtgg acaagagagt ggaacccaag          660
tcctgcgaca agacccacac ctgtcctcca tgtcctgcc cagaagctga gggcgctcct          720
tccgtgttcc tgtttcctcc aaagcctaag gacaccctga tgatctctcg gacccctgaa          780
gtgacctgcg tggtggtgga tgtgtctcac gaggacccag aagtgaagtt caattggtac          840
gtggacggcg tggaagtgca caacgccaag accaagccta gaggaacaa gtacaactcc          900
acctacagag tggtgtccgt gctgaccgtg ctgcaccagg attggctgaa cggcaaagag          960
tacaagtgca aggtgtccaa caaggccctg ccttccagca tcgaaaagac catctccaag         1020
gccaagggcc agcctaggga accccaggtt tacaccctgc ctccaagccg ggaagagatg         1080
accaagaacc aggtgtccct gacctgcctc gtgaagggct ctaccccttc cgatatcgcc         1140
gtggaatggg agagcaatgg ccagcctgag aacaactaca agaacaaccc tcctgtgctg         1200
gactccgacg gctcattctt cctgtactcc aagctgacag tggacaagtc cagatggcag         1260
cagggcaacg tgttctcctg ctccgtgatg cacgaggccc tgcacaatca ctacacacag         1320
aagtccctgt ctctgtcccc tggcaag                                             1347

SEQ ID NO: 81           moltype = DNA   length = 645
FEATURE                 Location/Qualifiers
source                  1..645
                        mol_type = other DNA
                        organism = synthetic construct
SEQUENCE: 81
cagtccgtgc tgacccagcc tccttctgtt tctggtgctc ctggccagag agtgaccatc           60
tcttgctccg gctcctcctc caacatcggc tcctactacg tgtcctggta tcagcagctg          120
cctggcaccc tcctaaggt gctgatctac cggaacaacc agcggccttc tggcgtgccc           180
gatagattct ccggctctaa gtctggcacc tctgccagcc tggctatcac tggactgcag          240
gctgaggacg aggccgacta ctactgcgac tcttgggacc actcctccat gaacgtgttc          300
ggcggaggta ccaagctgac cgtgctggga cagcctaagg ctgcccttc cgtgactg            360
ttccctccat cctctgagga actgcaggcc aacaaggcta cccgtgtg cctgatctcc            420
gactttacc ctgcgctgt gaccgtggcc tggaaggctg atagttctcc tgtgaaggcc            480
ggcgtggaaa ccaccacacc ttccaagcag tccaacaaca aatacgccgc ctcctcctac          540
ctgtctctga ccccctgaaca gtggaagtcc caccggtcct cagctgcca gtgacccat            600
```

```
gagggctcca ccgtggaaaa gaccgtggct cctaccgagt gctct              645
```

SEQ ID NO: 82           moltype = DNA   length = 15
FEATURE                 Location/Qualifiers
source                  1..15
                        mol_type = other DNA
                        organism = synthetic construct
SEQUENCE: 82
```
agctacgcta tgcac                                                15
```

SEQ ID NO: 83           moltype = DNA   length = 57
FEATURE                 Location/Qualifiers
source                  1..57
                        mol_type = other DNA
                        organism = synthetic construct
SEQUENCE: 83
```
cggatcaaga gcgttgccca aggcggcacc accgattacg ctgctcatgt gaagggc   57
```

SEQ ID NO: 84           moltype = DNA   length = 24
FEATURE                 Location/Qualifiers
source                  1..24
                        mol_type = other DNA
                        organism = synthetic construct
SEQUENCE: 84
```
gtgtcccact ctaccttcga tgtg                                      24
```

SEQ ID NO: 85           moltype = DNA   length = 21
FEATURE                 Location/Qualifiers
source                  1..21
                        mol_type = other DNA
                        organism = synthetic construct
SEQUENCE: 85
```
ggcttcacct tctccagcta c                                         21
```

SEQ ID NO: 86           moltype = DNA   length = 24
FEATURE                 Location/Qualifiers
source                  1..24
                        mol_type = other DNA
                        organism = synthetic construct
SEQUENCE: 86
```
aagagcgttg cccaaggcgg cacc                                      24
```

SEQ ID NO: 87           moltype = DNA   length = 39
FEATURE                 Location/Qualifiers
source                  1..39
                        mol_type = other DNA
                        organism = synthetic construct
SEQUENCE: 87
```
tccggctcct cctccaacat cggctcctac tacgtgtcc                      39
```

SEQ ID NO: 88           moltype = DNA   length = 21
FEATURE                 Location/Qualifiers
source                  1..21
                        mol_type = other DNA
                        organism = synthetic construct
SEQUENCE: 88
```
cggaacaacc agcggccttc t                                         21
```

SEQ ID NO: 89           moltype = DNA   length = 30
FEATURE                 Location/Qualifiers
source                  1..30
                        mol_type = other DNA
                        organism = synthetic construct
SEQUENCE: 89
```
gactcttggg accactcctc catgaacgtg                                30
```

SEQ ID NO: 90           moltype = DNA   length = 357
FEATURE                 Location/Qualifiers
source                  1..357
                        mol_type = other DNA
                        organism = synthetic construct
SEQUENCE: 90
```
gaagtgcagc tggtggaatc tggcggcgga cttgtgaaac ctggcggctc tctgagactg   60
tcttgtgccg cttccggctt caccttctcc agctacgcta tgcactgggt ccgacaggcc  120
cctggcaaag gattggagtg ggtcggacgg atcaagagcg ttgcccaagg cggcaccacc  180
gattacgctg ctcatgtgaa gggcagattc accatcagcc gggacgactc caagaacacc  240
ctgtacctgc agatgaactc cctgaaaacc gaggacaccg ccgtgtacta ctgcgccaga  300
gtgtcccact ctaccttcga tgtgtggggc cagggcacac tggttacagt ctcgagc     357
```

```
SEQ ID NO: 91             moltype = DNA   length = 333
FEATURE                   Location/Qualifiers
source                    1..333
                          mol_type = other DNA
                          organism = synthetic construct
SEQUENCE: 91
cagtccgtgc tgacccagcc tccttctgtt tctggtgctc ctggccagag agtgaccatc   60
tcttgctccg gctcctcctc caacatcggc tcctactacg tgtcctggta tcagcagctg  120
cctggcaccg ctcctaaggt gctgatctac cggaacaagc gcggccttc tggcgtgccc   180
gatagattct ccggctctaa gtctggcacc tctgccagcc tggctatcac tggactgcag  240
gctgaggacg aggccgacta ctactgcgac tcttgggacc actcctccat gaacgtgttc  300
ggcggaggta ccaagctgac cgtgctggga cag                               333

SEQ ID NO: 92             moltype = DNA   length = 1347
FEATURE                   Location/Qualifiers
source                    1..1347
                          mol_type = other DNA
                          organism = synthetic construct
SEQUENCE: 92
gaagtgcagc tggtggaatc tggcggcgga cttgtgaaac tggcggctc tctgagactg   60
tcttgtgccg cttccggctt caccttctcc agctacgcta tgcactgggt ccgacaggcc  120
cctggcaaag gattggagtg ggtcggacg atcaagacg ttgccaagg cggcaccaac   180
gattacgctg tcatgtgaa gggcagattc accatcagcc gggacgactc caagaacacc  240
ctgtacctgc agatgaactc cctgaaaacc gaggacaccg ccgtgtacta ctgcgccaga  300
gtgtcccact ctaccttcga tgtgtgggc agggcacac tggttacagt ctcgagcgcc   360
tccaccaaag gaccctctgt gtttcctctg gctccctccg caagtctac tctggtgga   420
acagctgccc tgggctgcct ggtcaaggat tactttcctg agcctgtgac cgtgtcctgg  480
aactctggcg ctctgacatc tggcgtgcac accttccag ctgtgctgca gtcctctggc   540
ctgtacagcc tgtcctctgt cgtgaccgtg ccttctagct ctctgggcac ccagacctac  600
atctgcaaca tgaaccacaa gccttccaac accaaggtgg acaagagagt ggaacccaag  660
tcctgcgaca gacccacac ctgtcctcca tgtcctgctc cagaagctga gggcgctcct  720
tccgtgttcc tgtttcctcc aaagcctaag gacaccctga tgatctctcg accctgaa   780
gtgacctgcg tggtggtgga tgtgtctcac gaggacccag aagtgaagtt caattggtac   840
gtggacggcg tggaagtgca caacgccaag accaagcta gagaggaaca gtacaactcc   900
acctggtgtc cgt gctgaccgtg ctgcaccagg attggctgaa cggcaaagag   960
tacaagtgca aggtgtccaa caaggccctg ccttccagca tcgaaaagac catctccaag  1020
gccaagggcc agcctaggga accccaggtt tacaccctgc ctccaagccg ggaagagatg  1080
accaagaacc aggtgtccct gacctgcctc gtgaaggct ctaccccttc cgatatcgcc  1140
gtggaatggg agagcaatgg ccagcctgag aacaactaca agacaacccc tcctgtgctg  1200
gactccgacg gctcattctt cctgtactcc aagctgacag tggacaagtc cagatgcag  1260
cagggcaacg tgttctcctg ctccgtgatg cacgaggccc tgcacaatca ctacacacag  1320
aagtccctgt ctctgtcccc tggcaag                                     1347

SEQ ID NO: 93             moltype = DNA   length = 645
FEATURE                   Location/Qualifiers
source                    1..645
                          mol_type = other DNA
                          organism = synthetic construct
SEQUENCE: 93
cagtccgtgc tgacccagcc tccttctgtt tctggtgctc ctggccagag agtgaccatc   60
tcttgctccg gctcctcctc caacatcggc tcctactacg tgtcctggta tcagcagctg  120
cctggcaccg ctcctaaggt gctgatctac cggaacaacc agcggccttc tggcgtgccc  180
gatagattct ccggctctaa gtctggcacc tctgccagcc tggctatcac tggactgcag  240
gctgaggacg aggccgacta ctactgcgac tcttgggacc actcctccat gaacgtgttc  300
ggcggaggta ccaagctgac cgtgctggga cagcctaagg ctgcccctc cgtgacactg  360
ttccctccat cctctgagga actgcaggcc aacaaggcta ccctcgtgtg cctgatctct  420
gacttttacc ctggcgctgt gaccgtggcc tggaaggctg atagttctcc tgtgaaggcc  480
ggcgtggaaa ccaccacacc ttccaagcag tccaacaaca aatacgccgc ctcctcctac  540
ctgtctctga cccctgaaca gtggaagtcc accggtcct acagctgcca agtgaccat  600
gagggctcca ccgtggaaaa gaccgtggct cctaccgagt gctct                645

SEQ ID NO: 94             moltype = AA    length = 454
FEATURE                   Location/Qualifiers
source                    1..454
                          mol_type = protein
                          organism = synthetic construct
SEQUENCE: 94
EVQLVESGGG LVQPGGSLRL SCAASGFTFS SYAMHWVRQA TGKGLEWVSA IDTGGGTYYA   60
DSVKGRFTIS RENAKNSLYL QMNSLRAGDT AVYYCARDYY YYASGSYYKA FDIWGQGTMV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCDKT HTCPPCPAPE  240
AEGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPSSIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 95             moltype = AA    length = 214
FEATURE                   Location/Qualifiers
source                    1..214
```

```
                        mol_type = protein
                        organism = synthetic construct
SEQUENCE: 95
EIVLTQSPGT  LSLSPGERAT  LSCRASQSVS  SRYLAWYQQK  PGQAPRLLIY  GASSRATGIP   60
DRFSGSGSGT  DFTLTISRLE  PEDFAVYYCQ  QYGSPLTFGQ  GTKLEIKRTV  AAPSVFIFPP  120
SDEQLKSGTA  SVVCLLNNFY  PREAKVQWKV  DNALQSGNSQ  ESVTEQDSKD  STYSLSSTLT  180
LSKADYEKHK  VYACEVTHQG  LSSPVTKSFN  RGEC                                214

SEQ ID NO: 96           moltype = AA   length = 400
FEATURE                 Location/Qualifiers
source                  1..400
                        mol_type = protein
                        organism = synthetic construct
SEQUENCE: 96
AEPRLPLMYH  LAAVSDLSTG  LPSFWATGWL  GAQQYLTYNN  LRQEADPCGA  WIWENQVSWY   60
WEKETTDLKS  KEQLFLEAIR  TLENQINGTF  TLQGLLGCEL  APDNSSLPTA  VFALNGEEFM  120
RFNPRTGNWS  GEWPETDIVG  NLWMKQPEAA  RKESEFLLTS  CPERLLGHLE  RGRQNLEWKE  180
PPSMRLKARP  GNSGSSVLTC  AAFSFYPPEL  KFRFLRNGLA  SGSGNCSTGP  NGDGSFHAWS  240
LLEVKRGDEH  HYQCQVEHEG  LAQPLTVDLD  SPARSSVNSR  GLNDIFEAQK  IEWHEHHHHH  300
HIQKTPQIQV  YSRHPPENGK  PNFLNCYVSQ  FHPPQIEIEL  LKNGKKIPNI  EMSDLSFSKD  360
WSFYILAHTE  FTPTETDVYA  CRVKHVTLKE  PKTVTWDRDM                          400
```